(12) United States Patent
Behar et al.

(10) Patent No.: US 11,266,639 B2
(45) Date of Patent: *Mar. 8, 2022

(54) USE OF HEXOKINASE 2/MITOCHONDRIA-DETACHING COMPOUNDS FOR TREATING HEXOKINASE-2 (HK2)-EXPRESSING CANCERS

(71) Applicant: Vidac Pharma Ltd., Jerusalem (IL)

(72) Inventors: Vered Behar, Bet Zayit (IL); Oren Menahem Becker, Mevasseret Zion (IL); Hadas Tamar Pahima, Moshav Ahuzam (IL); Reut Yosef Hamo, Ramot Meir (IL)

(73) Assignee: VIDAC PHARMA LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/576,825

(22) PCT Filed: Nov. 7, 2017

(86) PCT No.: PCT/IL2017/051214
§ 371 (c)(1),
(2) Date: Nov. 26, 2017

(87) PCT Pub. No.: WO2018/083705
PCT Pub. Date: May 11, 2018

(65) Prior Publication Data
US 2018/0303820 A1      Oct. 25, 2018

Related U.S. Application Data

(60) Provisional application No. 62/577,256, filed on Oct. 26, 2017, provisional application No. 62/443,745, filed on Jan. 8, 2017, provisional application No. 62/443,744, filed on Jan. 8, 2017, provisional application No. 62/418,323, filed on Nov. 7, 2016.

(51) Int. Cl.

| | | |
|---|---|---|
| *A61K 31/47* | (2006.01) |
| *A61K 31/496* | (2006.01) |
| *A61P 35/00* | (2006.01) |
| *A61P 35/02* | (2006.01) |
| *A61K 45/06* | (2006.01) |
| *A61K 9/00* | (2006.01) |
| *A61K 9/06* | (2006.01) |
| *A61K 51/04* | (2006.01) |
| *C12Q 1/6886* | (2018.01) |
| *A61K 31/506* | (2006.01) |
| *A61K 39/395* | (2006.01) |

(52) U.S. Cl.
CPC .......... *A61K 31/47* (2013.01); *A61K 9/0014* (2013.01); *A61K 9/0019* (2013.01); *A61K 9/0029* (2013.01); *A61K 9/0053* (2013.01); *A61K 9/06* (2013.01); *A61K 31/496* (2013.01); *A61K 31/506* (2013.01); *A61K 39/39558* (2013.01); *A61K 45/06* (2013.01); *A61K 51/0491* (2013.01); *A61P 35/00* (2018.01); *A61P 35/02* (2018.01); *C12Q 1/6886* (2013.01)

(58) Field of Classification Search
CPC .... A61K 31/47; A61K 9/0014; A61K 9/0019; A61K 9/0029; A61K 9/0053; A61K 9/06; A61K 31/496; A61K 31/506; A61K 39/39558; A61K 45/06; A61K 51/0491; A61P 35/02; A61P 35/00; C12Q 1/6886
See application file for complete search history.

(56) References Cited

U.S. PATENT DOCUMENTS

| | | | |
|---|---|---|---|
| 9,284,252 B2 | 3/2016 | Herzberg | |
| 9,284,274 B2* | 3/2016 | Kashman | ............ C07D 215/32 |
| 2004/0097734 A1 | 5/2004 | Gerlach et al. | |
| 2013/0089615 A1* | 4/2013 | Fehr Pereira Lopes | ..................... A61K 31/19 424/493 |
| 2013/0203689 A1* | 8/2013 | Ksshman | ............ C07D 215/32 514/25 |
| 2015/0080430 A1 | 3/2015 | Herzberg et al. | |
| 2015/0307564 A1* | 10/2015 | Young | ................. C12N 5/0636 424/134.1 |

FOREIGN PATENT DOCUMENTS

| | | | |
|---|---|---|---|
| WO | WO 2005/054172 A2 | 6/2005 | |
| WO | WO 2007/066336 A2 | 6/2007 | |
| WO | WO 2007/066337 A2 | 6/2007 | |
| WO | WO 2008/111088 A2 | 9/2008 | |
| WO | WO-2010143180 A1 * | 12/2010 | ........... A61K 31/215 |

(Continued)

OTHER PUBLICATIONS

Saad et al. "Guidelines for the management of castrate-resistant prostate cancer," Can Urol Assoc J. Dec. 2010; 4(6): 380-384 (Year: 2010).*

Definition of Immunocompromised, Cancer.gov website (https://www.cancer.gov/publications/dictionaries/cancer-terms/def/immunocompromised), accessed 2019. (Year: 2019).*

(Continued)

*Primary Examiner* — Jeffrey S Lundgren
*Assistant Examiner* — William Y Lee
(74) *Attorney, Agent, or Firm* — Mark S. Cohen; Pearl Cohen Zedek Latzer Baratz LLP

(57) ABSTRACT

The present invention provides methods of use of hexokinase 2 (HK2)/mitochondria-detaching compounds, including jasmonate derivatives and piperazine derivatives and pharmaceutical compositions including such compounds for treating, inhibiting, or suppressing a hexokinase-2 (HK2)-expressing cancer.

52 Claims, 15 Drawing Sheets

(56) References Cited

FOREIGN PATENT DOCUMENTS

| WO | WO 2014/143180 A1 | 9/2014 |
|---|---|---|
| WO | WO-2017/168416 | 10/2017 |
| WO | WO 2018/033918 A1 | 2/2018 |
| WO | WO 2018/083705 A1 | 5/2018 |
| WO | WO-2010/143180 | 12/2020 |

OTHER PUBLICATIONS

Arbel et al. "Mediation of the antiapoptotic activity of Bcl-xL protein upon interaction with VDAC1 protein" Journal of Biological Chemistry, 2012, 287.27: 23152-23161.
Batlevi et al. CAS: 167: 174048, 2015.
Behar, Vered, et al. A Hexokinase 2 Modulator for Field-Directed Treatment of Experimental Actinic Keratoses. Journal of Investigative Dermatology, 2018, 138.12: 2635-2643.
Berge et al. "Pharmaceutical salts" Journal of pharmaceutical sciences. Jan. 1, 1977;66(1):1-9.
Buchwald et al. "Long-term, continuous intravenous heparin administration by an implantable infusion pump in ambulatory patients with recurrent venous thrombosis" Surgery. Oct. 1, 1980;88(4):507-16.
Chaqour et al. "Chronic UVB-and all-trans retinoic-acid-induced qualitative and quantitative chances in hairless mouse skin" ournal of Photochemistry and Photobiology B: biology, 1995, 28.2: 125-135.
Cozzi et al. "Ingenol mebutate field-directed treatment of UVB-damaged skin reduces lesion formation and removes mutant p53 patches" Journal of Investigative Dermatology, 2012, 132.4: 1263-1271.
Dinkova-Kostova et al. "A dicyanotriterpenoid induces cytoprotective enzymes and reduces multiplicity of skin tumors in UV-irradiated mice" Biochemical and biophysical research communications 2008, 367.4: 859-865.
Fiebig et al. "Combined in vitro/in vivo test procedure with human tumor xenografts for anticancer drug development" Strahlentherapie und Onkologie: Organ der Deutschen Rontgengesellschaft . . . [et al]. Jul. 1989;165(7):522.
Fiebig et al. "CGP 6809—A new nitrosoureido-sugar derivative with activity in human tumor xenografts" Cancer chemotherapy and pharmacology. Jun. 1, 1989;23(6):337-40.
Fukunaga et al. "Evaluation of esophageal cancers using fluorine-18-fluorodeoxyglucose PET" The Journal of Nuclear Medicine. Jun. 1, 1998;39(6):1002.
Goldin et al. "Methyl jasmonate binds to and detaches mitochondria-bound hexokinase" Oncogene, 2008, 27.34: 4636.
Gottlob et al. "Inhibition of early apoptotic events by Akt/PKB is dependent on the first committed step of glycolysis and mitochondrial hexokinase" Genes & development, 2001, 15.11: 1406-1418.
Hampton et al. "NAGging Hexokinase PEPs up NLRP3" Cell host & microbe. Aug. 10, 2016;20(2):130-2.
Harvima et al. "Mast cells as regulators of skin inflammation and immunity" Acta dermato-venereologica, 2011, 91.6: 640-649.
Hay, Nissim. Reprogramming glucose metabolism in cancer: can it be exploited for cancer therapy?. Nature Reviews Cancer, 2016, 16.10: 635.
International Search Report for PCT Application No. PCT/IL2017/051214 dated Feb. 11, 2018.
John et al. "Subcellular localization of hexokinases I and II directs the metabolic fate of glucose" PloS one, 2011, 6.3: e17674.
Kim et al. "mTOR-targeted therapy: differential perturbation to mitochondrial membrane potential and permeability transition pore plays a role in therapeutic response" Biochemical and biophysical research communications. Apr. 25, 2014;447(1):184-91.
Kligman et al. "Histogenesis and progression of ultraviolet light-induced tumors in hairless mice" Journal of the National Cancer Institute, 1981, 67.6: 1289-1297.
Kolho et al. "antibodies in dialysis patients and patients with leukemia" Journal of medical virology. Aug. 1993;40(4):318-21.
Krasnov et al. "Targeting VDAC-bound hexokinase II: a promising approach for concomitant anti-cancer therapy" Expert opinion on therapeutic targets, 2013, 17.10: 1221-1233.
Kvansakul et al. "The Bcl-2 family: structures, interactions and targets for drug discovery" Apoptosis, 2015, 20.2: 136-150.
LEE et ai. CAS: 158:205499, 2013.
Li et al. "Deguelin inhibits non-small cell lung cancer via down-regulating Hexokinases II-mediated glycolysis" Oncotarget, 2017, 8.20: 32586.
Li et al. "Benserazide, a dopadecarboxylase inhibitor, suppresses tumor growth by targeting hexokinase 2" Journal of Experimental & Clinical Cancer Research, 2017, 36.1: 58.
Lin, Hong, et al. Discovery of a novel 2, 6-disubstituted glucosamine series of potent and selective hexokinase 2 inhibitors. ACS medicinal chemistry letters, 2016, 7.3: 217-222.
Lis et al. "The HK2 dependent "Warburg effect" and mitochondrial oxidative phosphorylation in cancer: targets for effective therapy with 3-bromopyruvate" Molecules. 2016;21(12):1730.
Lunt et al. "Aerobic glycolysis: meeting the metabolic requirements of cell proliferation" Annual review of cell and developmental biology, 2011, 27: 441-464.
Madan et al. "Non-melanoma skin cancer" The lancet. Feb. 20, 2010;375(9715):673-85.
Majewski et al. "Hexokinase-mitochondria interaction mediated by Akt is required to inhibit apoptosis in the presence or absence of Bax and Bak" Molecular cell. Dec. 3, 2004;16(5):819-30.
Mathupala et al. "Hexokinase-2 bound to mitochondria: cancer's stygian link to the "Warburg Effect" and a pivotal target for effective therapy" In Seminars in cancer biology Feb. 1, 2009 (vol. 19, No. 1, pp. 17-24). Academic Press.
Mishra et al. CAS: 140: 74883, 2003.
Oppel et al. "Actinic keratosis: the key event in the evolution from photoaged skin to squamous cell carcinoma" Skin pharmacology and physiology. 2004;17(2):67-76.
O'Sullivan et al. "When hexokinase gets that NAG-ing feeling . . . " Cell metabolism. Aug. 9, 2016;24(2):198-200.
Oyama et al. "Increased number of mast cells in the dermis in actinic keratosis lesions effectively treated with imiquimod" The Journal of dermatology. Aug. 2017;44(8):944-9.
Pastorino et al. "Regulation of hexokinase binding to VDAC" Journal of bioenergetics and biomembranes. Jun. 1, 2008;40(3):171-82.
Pastorino et al. "Mitochondrial binding of hexokinase II inhibits Bax-induced cytochrome c release and apoptosis" Journal of Biological Chemistry. Mar. 1, 2002;277(9):7610-8.
Patra et al. "Hexokinase 2 is required for tumor initiation and maintenance and its systemic deletion is therapeutic in mouse models of cancer. Cancer cell" Aug. 12, 2013;24(2):213-28.
Pedersen et al. "Mitochondrial bound type II hexokinase: a key player in the growth and survival of many cancers and an ideal prospect for therapeutic intervention" Biochimica et Biophysica Acta (BBA)-Bioenergetics. Sep. 10, 2002;1555(1-3):14-20.
Pedley et al. "Direct observation of hexokinase translocation in stimulated macrophages" Biochemical Journal. Apr. 15, 1993;291(2):515-22.
Peng et al. "Aberrant expression of the glycolytic enzymes aldolase B and type II hexokinase in hepatocellular carcinoma are predictive markers for advanced stage, early recurrence and poor prognosis" Oncology reports. Apr. 1, 2008;19(4):1045-53.
Phillips et al. "Curcumin inhibits UV radiation-induced skin cancer in SKH-1 mice" Otolaryngology—Head and Neck Surgery, May 2013;148(5):797-803.
Rebel et al. "Early p53-positive foci as indicators of tumor risk in ultraviolet-exposed hairless mice: kinetics of induction, effects of DNA repair deficiency, and p53 heterozygosity" Cancer Research. Feb. 2, 2001;61(3):977-83.
Rho et al. "Expression of type 2 hexokinase and mitochondria-related genes in gastric carcinoma tissues and cell lines" Anticancer research. Jan. 1, 2007;27(1A):251-8.
Röwert-Huber et al. "Actinic keratosis is an early in situ squamous cell carcinoma: a proposal for reclassification" British Journal of Dermatology. May 2007;156:8-12.

(56) References Cited

OTHER PUBLICATIONS

Sadelain et al. "The basic principles of chimeric antigen receptor design" Cancer Discov 3 (4): 388-398.
Saudek et al. "A preliminary trial of the programmable implantable medication system for insulin delivery" New England Journal of Medicine. Aug. 31, 1989;321(9):574-9.
Seton-Rogers S. "Tumour immunology: An exhausting metabolic competition" Nature Reviews Cancer. Sep. 24, 2015;15(10):573.
Shoshan-Barmatz et al. "The mitochondrial voltage-dependent anion channel 1 in tumor cells" Biochimica et Biophysica Acta (BBA)-Biomembranes. Oct. 1, 2015;1848(10):2547-75.
Shoshan-Barmatz et al. "VDAC1 : from structure to cancer therapy. Frontiers in oncology" Nov. 29, 2012;2:164.
Smith TA. "Mammalian hexokinases and their abnormal expression in cancer" British journal of biomedical science. Apr. 1, 2000;57(2):170.
Ting et al. "Reactivity of autolymphocytotoxic antibodies from dialysis patients with lymphocytes from chronic lymphocytic leukemia (CLL) patients" Transplantation. Jan. 1978;25(1):31-3.
"Vidac Pharma Initiates Phase I Clinical Trial with its Novel VDAC/HK2 Modulator", Feb. 25, 2016 (retrieved from: http://www.vidacpharma.com/news/64-vidac-pharma-initiates-phase-i-clinical-trial-with-its-novel-vdac-hk2-modulator) Feb. 25, 2016.
Wilson JE. "Isozymes of mammalian hexokinase: structure, subcellular localization and metabolic function" Journal of Experimental Biology. Jun. 15, 2003;206(12):2049-57.
Wolf et al. "Hexokinase is an innate immune receptor for the detection of bacterial peptidoglycan" Cell. Jul. 28, 2016;166(3):624-36.
Zalaudek et al. "Morphologic grading and treatment of facial actinic keratosis" Clinics in dermatology. Jan. 1, 2014;32(1):80-7.
Krasnov. G. S., Dmitriev, A. A., Lakunina, V. A., Kirpiy, A. A., & Kudryavtseva, A. V. 2013). Targeting VDAC-bound hexokinase II: a promising approach for concomitant anti-cancer therapy. *Expert opinion on therapeutic targets*, 17(10), 1221-1233.
Brickman et al. "VDA-1102, a first-in-class VDAC/HK modulator entering phase 1/2 drug development, for treatment of actinic keratosis and cutaneous squamous cell carcinoma: 3134" Journal of the American Academy of Dermatology. May 2016;74(5).
Supplementary European Search Report for European Application No. 17867282.0 dated Nov. 11, 2020.

\* cited by examiner

HK1 catalytic activity

HK2 catalytic activity

| | Minipig | Rat | Mouse | Additional Toxicology Studies | |
|---|---|---|---|---|---|
| | | | | Test | Outcome |
| Duration | 28 days | 28 days | 50 days | Dermal Sensitization (guinea pig) | ✓ |
| Treatment | Dermal Application (10% of body surface) | Oral Application | Dermal Application | Phototoxicity | ✓ |
| Adverse Events | No deaths, no serious adverse effects, no systemic side effects | No deaths, no serious adverse effects outside of GI tract | No deaths, no serious adverse effects, no side effects | Genotoxicity | ✓ |
| | | | | ✓ Passed | |

Efficacy Studies | Side Effect Profile | Toxicology Studies

Figure 8

USE OF HEXOKINASE 2/MITOCHONDRIA-DETACHING COMPOUNDS FOR TREATING HEXOKINASE-2 (HK2)-EXPRESSING CANCERS

CROSS-REFERENCE TO RELATED APPLICATIONS

This application is a National Phase Application of PCT International Application No. PCT/IL2017/051214 filed Nov. 7, 2017, which claims priority to U.S. Provisional Application No. 62/418,323, filed Nov. 7, 2016, U.S. Provisional Application No. 62/443,744, filed Jan. 8, 2017, U.S. Provisional Application No. 62/443,745, filed Jan. 8, 2017, and U.S. Provisional Application No. 62/577,256, filed Oct. 26, 2017, which are hereby incorporated by reference in their entirety.

FIELD OF THE INVENTION

The present invention provides methods of use of hexokinase 2 (HK2)/mitochondria-detaching compounds, including jasmonate derivatives and piperazine derivatives and pharmaceutical compositions including such compounds for treating, inhibiting, or suppressing a hexokinase-2 (HK2)-expressing cancer.

BACKGROUND OF THE INVENTION

Cancer is the leading cause of death worldwide, accounting for 8.2 million deaths in 2012, according to the World Health Organization. It is predicted that one out of two men and one out of three women will die of cancer by the end of the 21st century. The search for an effective anticancer drug continues.

It is well established that cancer cells differ from most somatic adult cells by their high rate of aerobic glycolysis. This distinct property of cancer cells, known as the Warburg effect, is often used for tumor imaging in vivo following the administration of the labeled glucose analog, fluoro deoxy glucose (FDG). Glucose metabolism increases in malignant tumors, and in the glycolytic pathway, hexokinase activity correlates with tumor proliferative activity. Fluorine-18-FDG is phosphorylated by hexokinase within the cells and accumulates intracellularly as $^{18}$F-FDG-6-P0$_4$, since it is not a substrate of phosphohexose isomerase (the enzyme involved in the next step of the glycolytic pathway). The high uptake of the labeled FDG in cancer cells can then be detected by positron emission tomography (PET).

In addition to using the high rate of glucose metabolism in cancer cells to distinguish cancer cells from normal cells, glucose metabolism may be exploited to selectively target cancer cells for destruction. However, a major challenge in targeting glucose metabolism for cancer therapy is to identify a strategy that selectively targets cancer cells while sparing normal cells, and that does not dramatically impair systemic metabolic homeostasis.

SUMMARY OF THE INVENTION

In one embodiment, the present invention provides a compound that promotes the detachment of Hexokinase 2 (HK2) from the mitochondria for use in treating, inhibiting or suppressing a hexokinase-2 (HK2)-expressing cancer or tumor in a subject.

In another embodiment, the present invention provides a compound that promotes the detachment of Hexokinase 2 (HK2) from the mitochondria for use in inhibiting the proliferation of hexokinase-2 (HK2)-expressing cells in a subject.

In another embodiment, the present invention provides a compound that promotes the detachment of Hexokinase 2 (HK2) from the mitochondria for use in potentiating the immune response to a hexokinase-2 (HK2)-expressing cancer or tumor in a subject.

In another embodiment, the present invention provides a compound that promotes the detachment of Hexokinase 2 (HK2) from the mitochondria for use in treating, suppressing, or inhibiting a hexokinase-2 (HK2)-expressing precancerous condition or a benign hyperproliferative disorder in a subject.

In another embodiment, the present invention provides a method of evaluating the efficacy of a cancer therapy with a compound that promotes the detachment of Hexokinase 2 (HK2) from the mitochondria in a subject with a tumor comprising the steps of: (a) performing a fluorodeoxyglucose (FDG)-PET scan on said subject; and (b) identifying an HK2-expressing tumor in said subject on said FDG-PET scan; wherein treatment with said compound is administered to said subject if said subject comprises a HK2-expressing tumor.

In another embodiment, the present invention provides a method of evaluating the efficacy of a cancer therapy with a compound that promotes the detachment of Hexokinase 2 (HK2) from the mitochondria in a subject with a tumor comprising the steps of: (a) performing a first evaluation of HK2 levels in said tumor in said subject prior to treatment of said subject with a compound that promotes the detachment of Hexokinase 2 (HK2) from the mitochondria; and (b) performing a second evaluation of HK2 levels in said tumor in said subject after treatment with said compound, wherein if said tumor comprises decreased levels of HK2 in said second evaluation compared to said first evaluation, then said cancer therapy was efficacious in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 8. Toxicology Profile of Formula C. Toxicology studies in mouse, rat, and minipig, using various modes of administration, showed minimal toxicity which reflects the inherent selectivity of this treatment.

DETAILED DESCRIPTION OF THE PRESENT INVENTION

Figure 1:
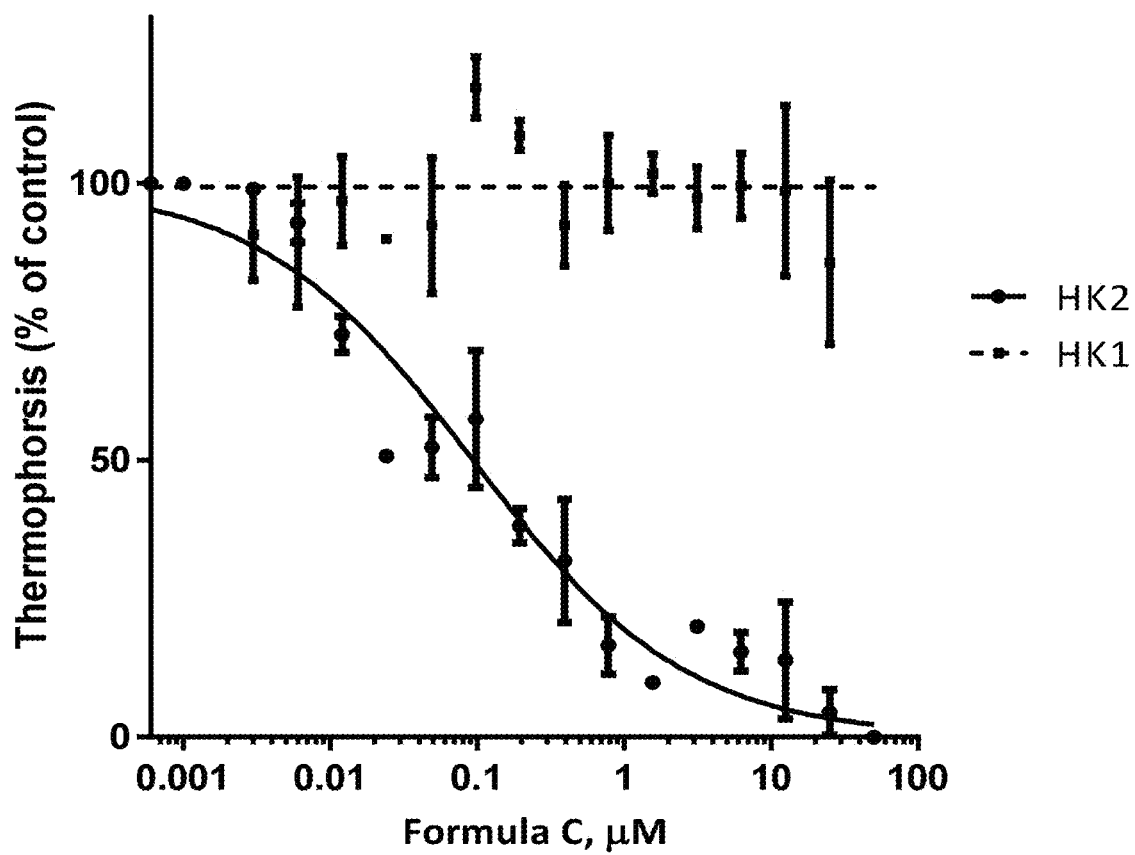
FIG. 1. In vitro activity of Formula C. Dissociation of voltage dependent anion channel (VDAC)/Hexokinase (HK) complexes by Formula C, Microscale Thermophoresis (MST) assay. Mean±SEM, n=3 independent studies.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides a method for treating, inhibiting or suppressing a hexokinase-2 (HK2)-expressing cancer or tumor in a subject comprising contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a compound that promotes the detachment of Hexokinase 2 (HK2) from the mitochondria for use in inhibiting the proliferation of hexokinase-2 (HK2)-expressing cells in a subject. In one embodiment, the compound is a jasmonate derivative, as described herein. In another embodiment, the compound is a piperazine derivative, as described herein.

In another embodiment, the present invention provides a compound that promotes the detachment of Hexokinase 2 (HK2) from the mitochondria for use in treating, suppressing, or inhibiting a hexokinase-2 (HK2)-expressing precancerous condition or a benign hyperproliferative disorder in a subject. In one embodiment, the compound is a jasmonate derivative, as described herein. In another embodiment, the compound is a piperazine derivative, as described herein.

HK2/Mitochondria-Detaching Compounds

In one embodiment, compounds for use in the methods of the present invention comprise compounds that promote the detachment of HK2 from the mitochondria. In another embodiment, compounds for use in the methods of the present invention comprise compounds that promote the detachment of HK2 from the voltage-dependent anion channel (VDAC). In another embodiment, compounds for use in the methods of the present invention comprise compounds that disrupt the physical contact between HK2 and the mitochondria in general or specifically between HK2 and VDAC.

In one embodiment, compounds that disrupt HK2/mitochondria attachment are known in the art. In another embodiment, compounds may be easily evaluated for such function by a skilled artisan. In one embodiment, disruption of HK2/mitochondria attachment may be assayed in a cell-free environment, using a technology such as microscale thermophoresis (MST), or others evaluating protein-protein interaction modulators (as described in U.S. Provisional Patent Application No. 62/577,256, which is incorporated by reference herein in its entirety). In another embodiment, disruption of HK2/mitochondria attachment may be assayed in a cell-based assay using various methods including, inter alia, Western blot, wherein the mitochondrial fraction is examined. Such methods are well known in the art.

In one embodiment, administration of a HK2/mitochondria detaching compound as described herein leads to dissociation of HK2 from VDAC. In another embodiment, administration of the HK2/mitochondria detaching compound triggers apoptosis, which in one embodiment, leads to the death of cancer cells. In another embodiment, administration of the HK2/mitochondria detaching compound triggers apoptosis in cancer cells. In another embodiment, administration of the HK2/mitochondria detaching compound reduces glycolysis. In another embodiment, administration of the HK2/mitochondria detaching compound increases lactate production. In another embodiment, administration of the HK2/mitochondria detaching compound activates caspase 3.

In one embodiment, the compound comprises methyl jasmonate. In another embodiment, the compound comprises a methyl jasmonate derivative.

In one embodiment, the compound comprises a piperazine derivative.

Jasmonate Derivatives

In one embodiment, a jasmonate derivative as described herein comprises a compound represented by the structure of Formula (VII):

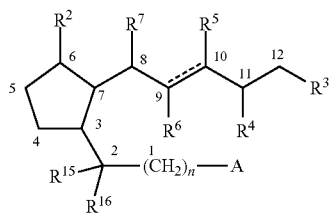

In one embodiment, A comprises $COR^1$; $R^1$ comprises an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof.

In another embodiment, A comprises $COR^1$; $R^1$ is quinolinyloxy; $R^2$ is oxo; $R^3$, $R^4$, $R^5$, $R^6$ and $R^7$ are each hydrogen, wherein the bond between $C_9$ and $C_{10}$ can be a single or double bond; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof.

In another embodiment, the compound is represented by the structure of formula C:

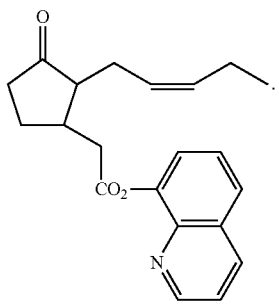

In one embodiment, the structure of formula C decouples HK2 from Voltage-dependent anion channel (VDAC) in cancer cells.

In one embodiment, an ester derivative of Jasmonic Acid may be used in the methods of the present invention. In another embodiment, other jasmonate derivatives may be used in the methods of the present invention. In one embodiment, halogenated jasmonate derivatives and related pharmaceutical compositions, as described in International Patent Application WO 2005/054172, which is incorporated by reference herein in its entirety, may be used in the methods of the present invention.

In another embodiment, jasmonate derivatives such as those described in International Patent Applications WO 2007/066336, WO 2010/143180, and WO 2007/066337, which are incorporated by reference herein in their entirety may be used in the methods of the present invention. In another embodiment, dermal compositions comprising jasmonate derivatives may be used in the methods of the present invention. Methods for preparing the jasmonate derivatives for use in the present invention are described, for example, in WO 2007/066336 and WO 2010/143180.

In one embodiment, stereoisomers of the jasmonate ester derivatives are contemplated either in admixture or in pure or substantially pure form. The jasmonate derivatives can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R, S, D or d or L or l or d,l or D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.*, 66: 1-19, 1977. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is also contemplated.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. "Hydrate" comprises a solvate wherein the solvent molecule comprises water.

The present invention also includes polymorphs of the compounds of the present invention and salts thereof. The term "polymorph" refers to a particular crystalline state of a substance, which can be characterized by particular physical properties such as X-ray diffraction, IR or Raman spectra, melting point, and the like.

In one embodiment, administration of a jasmonate derivative as described herein leads to dissociation of HK2 from VDAC. In another embodiment, administration of a jasmonate derivative leads to activation of an inflammasome, which, in one embodiment, leads to an immune response directed to cancer cells. In another embodiment, administration of a jasmonate derivative leads to apoptosis, which in one embodiment, leads to the death of cancer cells. In another embodiment, administration of a jasmonate derivative leads to reduced glycolysis.

Piperazine Derivatives

In another embodiment, the compound for use in the present invention comprises piperazine derivatives, which in one embodiment, comprise the compounds described in PCT Application No. PCT/IL2017/050909, which is incorporated herein by reference in its entirety. According to this aspect and in one embodiment, the present invention provides the use of a compound represented by the structure of Formula (II):

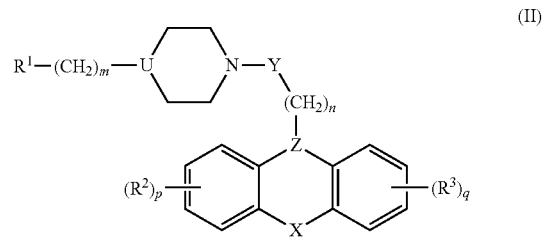

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2; and
p and q are each independently selected from 0, 1, 2, 3, and 4;
or a pharmaceutically acceptable salt thereof, with the proviso that when Z is CH, X is NH, S, or a bond.

In another embodiment, the following compound is excluded: a compound of Formula (II) wherein X is NH, Z is CH, Y is C=O, n is 0, m is 0, $R^1$ is a phenyl substituted by one or more alkoxy, and p and q are each 0.

In some embodiments, in the compound of Formula (II), m and n are each 0.

In some embodiments, in the compound of Formula (II), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (II), p is 0. In some embodiments, q is 0. In other embodiments, p is 0 and q is 0.

In some embodiments, in the compound of Formula (II), U is N.

In some embodiments, the compound for use in the invention is represented by a compound of Formula (III):

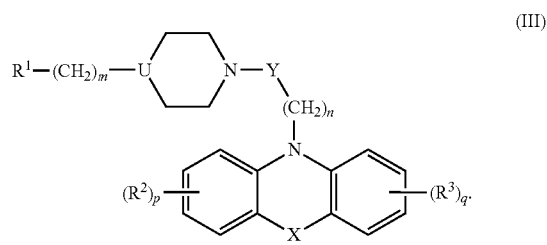

(III)

wherein X, U, $R^1$, $R^2$, $R^3$, m, n, p, and q are defined as anywhere herein.

In some embodiments, in the compound of Formula (III), X is O, NH, or a bond. In some embodiments, X is O. In other embodiments, X is a bond. In certain embodiments, X is NH.

In some embodiments, in the compound of Formula (III), m and n are each 0.

In some embodiments, in the compound of Formula (III), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (III), p is 0. In some embodiments, q is 0. In other embodiments, p is 0 and q is 0.

In some embodiments, in the compound of Formula (III), U is N.

In some embodiments, the compound for use in the present invention is represented by a compound of Formula (IV)

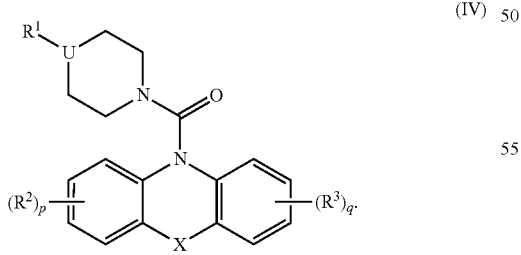

(IV)

wherein X, U, $R^1$, $R^2$, $R^3$, m, n, p, and q are defined as anywhere herein.

In some embodiments, in the compound of Formula (IV), X is O. In other embodiments, X is S. In certain embodiments, X is NH.

In some embodiments, in the compound of Formula (IV), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (IV), p is 0. In some embodiments, q is 0. In other embodiments, p is 0 and q is 0.

In some embodiments, in the compound of Formula (IV), U is N.

In some embodiments, the compound for use in the present invention is:

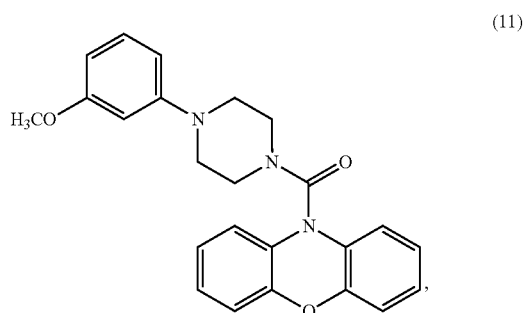

(11)

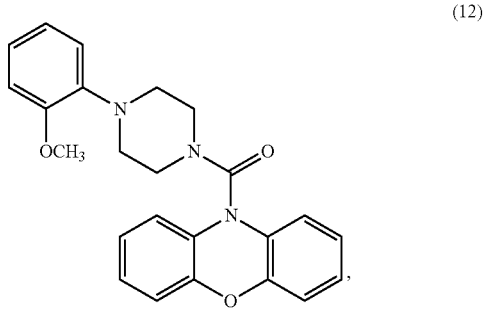 [SMILES: O=C(C1c2ccccc2Sc2ccccc21)N1CCN(c2ccccc2)CC1 ; "."]

(12)

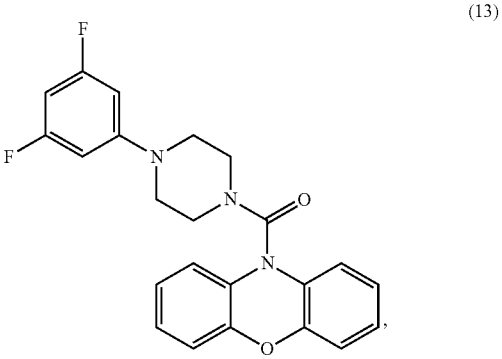

(13)

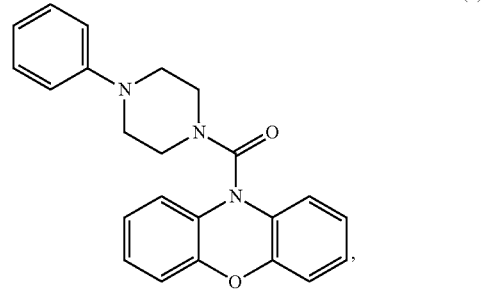

(1)

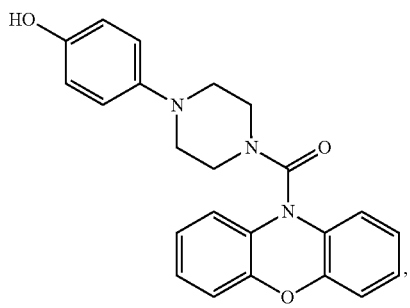
(14)

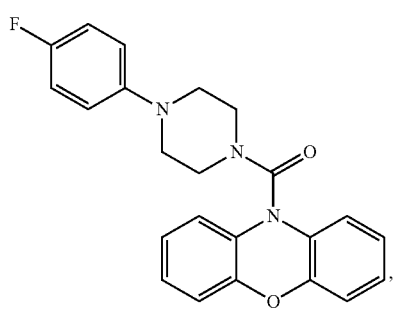
(15)

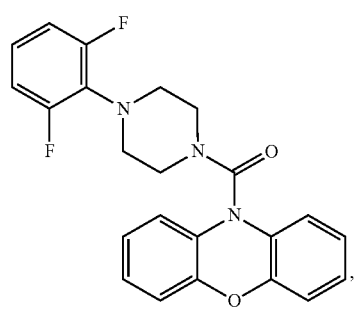
(5)

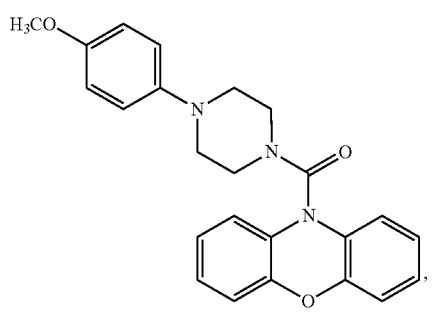
(4)

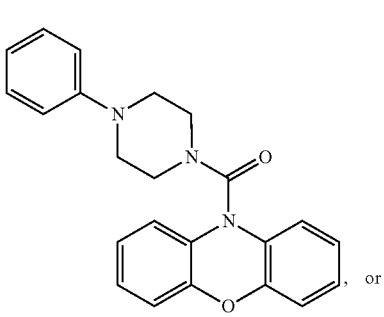
(16), or

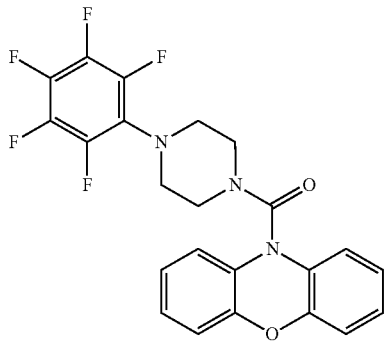
(2)

including salts, hydrates, solvates, polymorphs, optical isomers, geometrical isomers, enantiomers, diastereomers, and mixtures thereof.

In some embodiments, the compound for use in the invention is represented by a compound of Formula (V):

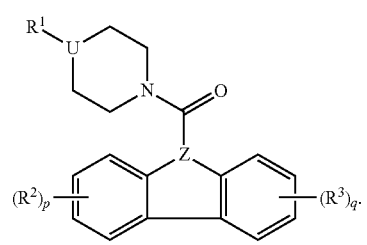
(V)

wherein X, U, $R^1$, $R^2$, $R^3$, m, n, p, and q are defined as anywhere herein.

In some embodiments, in the compound of Formula (V), Z is N. In other embodiments, Z is CH.

In some embodiments, in the compound of Formula (V), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (V), p is 0. In some embodiments, q is 0. In other embodiments, p is 0 and q is 0.

In some embodiments, in the compound of Formula (V), U is N.

In some embodiments, the compound for use in the present invention is:

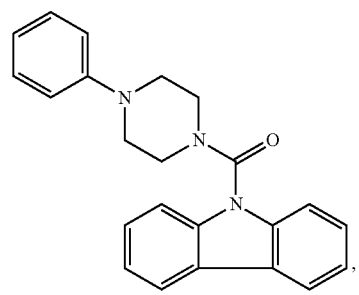
(20)

(21)

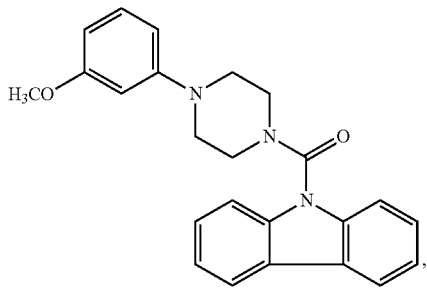

, (22)

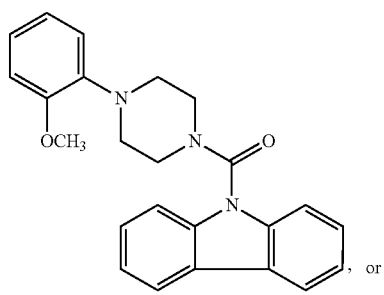

, or (23)

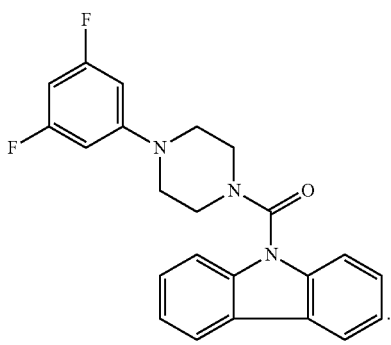

.

In some embodiments, the compound for use in the present invention comprises a di-meta-OMe analog, which in one embodiment is:

(24)

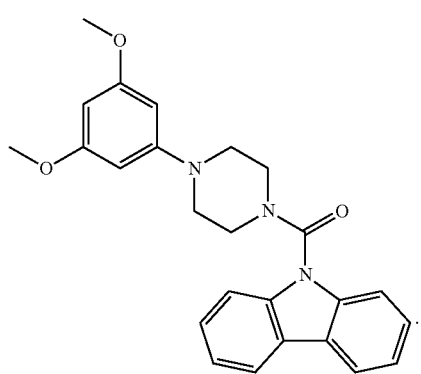

.

In some embodiments, the compound for use in the present invention is represented by a compound of Formula (VI):

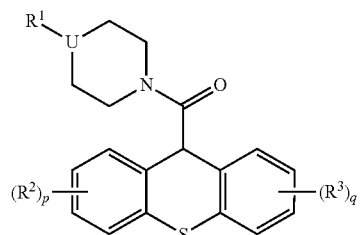

(VI)

wherein U, $R^1$, $R^2$, $R^3$, p, and q are defined as anywhere herein.

In some embodiments, in the compound of Formula (VI), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (VI), p is 0. In some embodiments, q is 0. In other embodiments, p is 0 and q is 0.

In some embodiments, in the compound of Formula (VI), U is N.

In some embodiments, the compound for use in the present invention is:

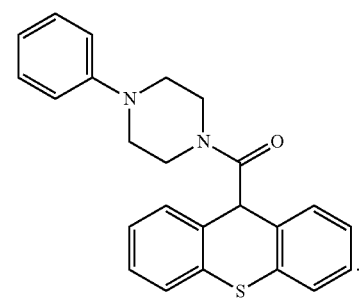

(3)

.

In another embodiment, $R^1$ is selected from the group consisting of phenyl, quinolinyl and isoquinolinyl, each of which may independently be unsubstituted or substituted with one or more halogen, $OR^a$ or $NR^aR^b$ wherein $R^a$ and $R^b$ are each independently selected from the group consisting of H or a $C_1$-$C_4$ alkyl.

In another embodiment, $R^1$ is C(=O)—$OR^a$ wherein $R^a$ is a $C_1$-$C_4$ alkyl. In other embodiments, $R^1$ is selected from the group consisting of:

a) phenyl;
b) fluorophenyl;
c) difluorophenyl;
d) pentafluorophenyl;

e) methoxyphenyl;
f; and

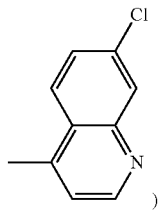

g) C(=O)—OCH$_2$CH$_3$.

Each possibility represents a separate embodiment of the present invention.

In some embodiments, in the compound of Formula (II) or in the compound of Formula (IV), X is S. In one embodiment, when X is S, Z is CH. In an alternative embodiment, the following compound is excluded: a compound of Formula (II) wherein X is S, Z is N, Y is C=O, n is 0, m is 0, R1 is an unsubstituted or substituted phenyl and p and q are each 0. In another embodiment, the following compound is excluded: a compound of formula (II) wherein X is S, Z is N, Y is C=O, n is 0, m is 0, R$^1$ is pyridinyl and p and q are each 0.

In some embodiments wherein X is S, R$^1$ is aryl, optionally substituted with one or more alkyl, arylalkyl, halogen, NO$_2$, CN, OR$^4$, and NR$^{5a}$R$^{5b}$, or a combination thereof. In some embodiments wherein X is S, R$^1$ is aryl substituted with one or more alkyl, arylalkyl, halogen, NO$_2$, CN, OR$^4$, and NR$^{5a}$R$^{5b}$, or a combination thereof. In some embodiments wherein X is S, R$^1$ is aryl substituted with one or more alkyl, arylalkyl, halogen, NO$_2$, and NR$^{5a}$R$^{5b}$, or a combination thereof. In some embodiments wherein X is S, R$^1$ is phenyl substituted with one or more alkyl, arylalkyl, halogen, NO$_2$, and NR$^{5a}$R$^{5b}$, or a combination thereof. In some embodiments wherein X is S, R$^1$ is aryl, optionally substituted with one or more halogen and C$_1$-C$_4$ alkyl, or a combination thereof. In some embodiments wherein X is S, R$^1$ is phenyl, optionally substituted with one or more halogen and C$_1$-C$_4$ alkyl, or a combination thereof.

In some embodiments wherein X is S, R$^1$ is heteroaryl, optionally substituted with one or more alkyl, arylalkyl, halogen, NO$_2$, CN, OR$^4$, and NR$^{5a}$R$^{5b}$, or a combination thereof. In some embodiments wherein X is S, R$^1$ is not pyridinyl. In some embodiments wherein X is S, R$^1$ is heteroaryl substituted with one or more alkyl, arylalkyl, halogen, NO$_2$, CN, OR$^4$, and NR$^{5a}$R$^{5b}$, or a combination thereof. In some embodiments wherein X is S, R$^1$ is heteroaryl substituted with one or more alkyl, arylalkyl, halogen, NO$_2$, and NR$^{5a}$R$^{5b}$, or a combination thereof. In some embodiments wherein X is S, R$^1$ is quinolinyl, or isoquinolinyl. In some embodiments wherein X is S, R$^1$ is quinolinyl or isoquinolinyl, optionally substituted with one or more alkyl, arylalkyl, halogen, NO$_2$, CN, OR$^4$, and NR$^{5a}$R$^{5b}$, or a combination thereof. In some embodiments wherein X is S, R$^1$ is quinolinyl or isoquinolinyl, optionally substituted with one or more halogen and C$_1$-C$_4$ alkyl, or a combination thereof. In certain embodiments wherein X is S, R$^1$ is C(=O)—OR$^a$, wherein R$^a$ is C$_1$-C$_4$ alkyl.

In one embodiment, the compound represented by the structure of Formula (II) as described herein is as described but having the proviso that:
(1) when Z is CH, X is NH, S, or a bond;
(2) when X is S, Z is CH; and
(3) the following compound: a compound of Formula (II) wherein X is NH, Z is CH, Y is C=O, n is 0, m is 0, R$^1$ is a phenyl substituted by one or more alkoxy, and p and q are each 0, is excluded.

In another embodiment, the compound represented by the structure of Formula (II) as described herein is as described but having the proviso that:
(1) when Z is CH, X is NH, S, or a bond and (2) the following compounds are excluded:
(i) a compound of Formula (II) wherein X is NH, Z is CH, Y is C=O, n is 0, m is 0, R1 is a phenyl substituted by one or more alkoxy, and p and q are each 0; and
(ii) a compound of Formula (II) wherein X is S, Z is N, Y is C=O, n is 0, m is 0, R1 is an unsubstituted or substituted phenyl and p and q are each 0.

In another embodiment, the compound represented by the structure of Formula (II) as described herein is as described but having the proviso that:
(1) when Z is CH, X is NH, S, or a bond;
(2) the following compounds are excluded:
(i) a compound of formula (II) wherein X is NH, Z is CH, Y is C=O, n is 0, m is 0, R$^1$ is a phenyl substituted by one or more alkoxy, and p and q are each 0; and
(ii) a compound of formula (II) wherein X is S, Z is N, Y is C=O, n is 0, m is 0, R$^1$ is pyridinyl and p and q are each 0.

In one embodiment, the compound is represented by Formula (II), wherein n is 0. According to this aspect and in one embodiment, the compound is represented by the structure of Formula (II-a):

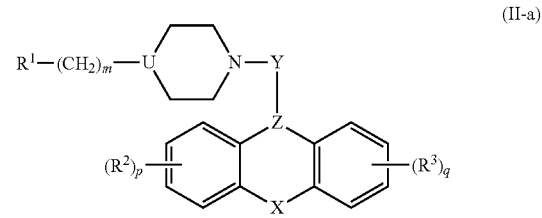

In another embodiment, the compound is represented by Formula (II) wherein X is O, Z is N, Y is C=O, n is 0, m is 0, R$^1$ is phenyl or methoxyphenyl and p and q are each 0.

In yet another embodiment, the compound is represented by Formula (II) wherein X is S, Z is CH, Y is C=O, n is 0, m is 0, R$^1$ is phenyl and p and q are each 0.

In one embodiment, the compound is represented by Formula (II) wherein X is O, Z is N, Y is C=O, n is 0, m is 0, R$^1$ is methoxyphenyl and p and q are each 0. In another embodiment, the compound is represented by Formula (II), wherein X is O, Z is N, Y is C=O, n is 0, m is 0, R$^1$ is difluorophenyl or pentafluorophenyl and p and q are each 0.

In another embodiment the compound is represented by Formula (II), wherein p and q are each 0 (i.e., R$^2$ and R$^3$ do not exist).

As demonstrated herein, said compound has unexpectedly been found to be a highly potent and selective cytotoxic agent, exhibiting selective cytotoxicity towards cancer as well as pre-cancerous cells and benign hyperproliferative disorders, while having little effect on normal cells.

As used herein, in some embodiments, an "alkyl" group refers to any saturated aliphatic hydrocarbon, including straight-chain and branched-chain alkyl groups. In one embodiment, the alkyl group has 1-4 carbons designated here as $C_1$-$C_4$-alkyl. In some embodiments, the alkyl group has 1-7 carbons designated here as $C_1$-$C_7$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl contains 5 or more ring atoms. In some embodiments, the heteroaryl group contains 5-10 ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, quinolyl (e.g. 1-quinolinyl, 2-quinolinyl, 3-quinolinyl, 4-quinolinyl, 5-quinolinyl, 6-quinolinyl, 7-quinolinyl and 8-quinolinyl), isoquinolinyl (e.g., 1-isoquinolinyl, 2-isoquinolinyl, 3-isoquinolinyl, 4-isoquinolinyl, 5-isoquinolinyl, 6-isoquinolinyl, 7-isoquinolinyl and 8-isoquinolinyl); naphthyridinyl (e.g., 1-naphthyridinyl, 2-naphthyridinyl), quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The term "halogen" or "halo" as used herein alone or as part of another group refers to chlorine, bromine, fluorine, and iodine.

The term "hydroxy" refers to an OH group. The terms "alkoxy" refers to the group $OR^a$ wherein $R^a$ is a $C_1$-$C_4$ alkyl as defined above. Nonlimiting examples of an alkoxy group is methoxy, ethoxy, n-propoxy, isopropoxy, n-butoxy, t-butoxy and like groups.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. The present invention intends to encompass all structural and geometrical isomers including cis, trans, E and Z isomers.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counter-ions for the anion of a salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylene diammonium, and like cations. See, for example, "Pharmaceutical Salts," Berge et al., J. Pharm. Sci., 66:1-19 (1977), which is incorporated herein by reference.

The present invention also includes the use of solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes use of polymorphs of the compounds of the present invention and salts thereof. The term "polymorph" refers to a particular crystalline state of a substance, which can be characterized by particular physical properties such as X-ray diffraction, IR spectra, melting point, and the like.

Other Compounds

In another embodiment, the compound for use in the present invention comprises 2-deoxyglucose (2-DG). In one embodiment, the compound comprises a peptide derived from the N-terminus of HK2, which in one embodiment, is HKVBD. Such peptides derived from the N-terminus of HK2 are known in the art and described, for example, in Wolf et al. 2016 (Cell. 2016 Jul. 28; 166(3):624-636) and Pastorino et al 2002 (JBC 277:7610-8), which are incorporated by reference herein in their entirety. In another embodiment, the compound comprises a peptidoglycan, which in one embodiment, is a bacterial peptidoglycan. In another embodiment, the compound comprises N-acetylglucosamine. In another embodiment, the compound comprises glucose-6-phosphate (G6P). In another embodiment, the compound comprises Lonidamine. In another embodiment, the compound comprises 3-bromopyruvate. In another embodiment, the compound comprises clotrimazole. In another embodiment, the compound comprises shRNA, which in one embodiment, comprises VDAC shRNA and, in another embodiment, comprises HK2 shRNA.

Cancer and Tumors

In one embodiment, the present invention provides a method for treating, inhibiting or suppressing a hexokinase-2 (HK2)-expressing cancer in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for treating, inhibiting or suppressing a hexokinase-2 (HK2)-expressing tumor in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for treating, inhibiting or suppressing a hexokinase-2 (HK2)-expressing hyperproliferative disorder in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein. In one embodiment, the hyperproliferative disorder comprises a cancer, a tumor, a pre-cancerous condition, or a benign hyperproliferative disorder.

In another embodiment, the present invention provides a method for treating a hexokinase-2 (HK2)-expressing cancer or tumor in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for inhibiting a hexokinase-2 (HK2)-expressing cancer or tumor in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for suppressing a hexokinase-2 (HK2)-expressing cancer or tumor in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for inhibiting the proliferation of hexokinase-2 (HK2)-expressing cells in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein. In one embodiment, the HK2-expressing cells are cancer cells. In another embodiment, the HK2-expressing cells are tumor cells.

In another embodiment, the present invention provides a method of potentiating the immune response to a hexokinase-2 (HK2)-expressing cancer or tumor in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method of treating a hexokinase-2 (HK2)-expressing pre-cancerous condition or a benign hyperproliferative disorder in a subject comprising the step of contacting one or more cells of said subject with a therapeutically effective amount of a compound that promotes the detachment of Hexokinase 2 (HK2) from the mitochondria.

In one embodiment, the compound is a jasmonate derivative, as described herein. In another embodiment, the compound is a piperazine derivative, as described herein.

In another embodiment, the present invention provides a method of suppressing a hexokinase-2 (HK2)-expressing pre-cancerous condition or a benign hyperproliferative disorder in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method of inhibiting a hexokinase-2 (HK2)-expressing pre-cancerous condition or a benign hyperproliferative disorder in a subject comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In another embodiment, the present invention provides a method for treating an HK2-expressing cancer comprising administering to a subject a composition comprising a compound as described herein, thereby promoting the detachment of HK2 from the mitochondria. In one embodiment, the compound is a jasmonate derivative, as described herein. In another embodiment, the compound is a piperazine derivative, as described herein.

In another embodiment, the present invention provides a method of decoupling HK2 from mitochondria comprising administering to one or more cells a composition comprising a compound as described herein. In one embodiment, the compound is a jasmonate derivative, as described herein.

In another embodiment, the compound is a piperazine derivative, as described herein.

In another embodiment, the present invention provides a method of selectively decoupling HK2 from mitochondria comprising administering to one or more cells a composition comprising a compound as described herein. In another embodiment, the present invention provides a method of decoupling HK2 and not HK1 from mitochondria comprising administering to one or more cells a composition comprising a compound as described herein. In one embodiment, the compound is a jasmonate derivative, as described herein.

In another embodiment, the compound is a piperazine derivative, as described herein.

In another embodiment, the present invention provides a method of promoting the detachment of HK2 from mitochondria comprising administering to one or more cells a composition comprising a compound as described herein. In one embodiment, the compound is a jasmonate derivative, as described herein. In another embodiment, the compound is a piperazine derivative, as described herein.

In another embodiment, the present invention provides a method of reducing cellular ATP levels in a cancer cell comprising administering to one or more cells a composition comprising a compound that promotes the detachment of HK2 from mitochondria. In one embodiment, such a method is demonstrated herein and in FIG. 2C.

Figure 3A:
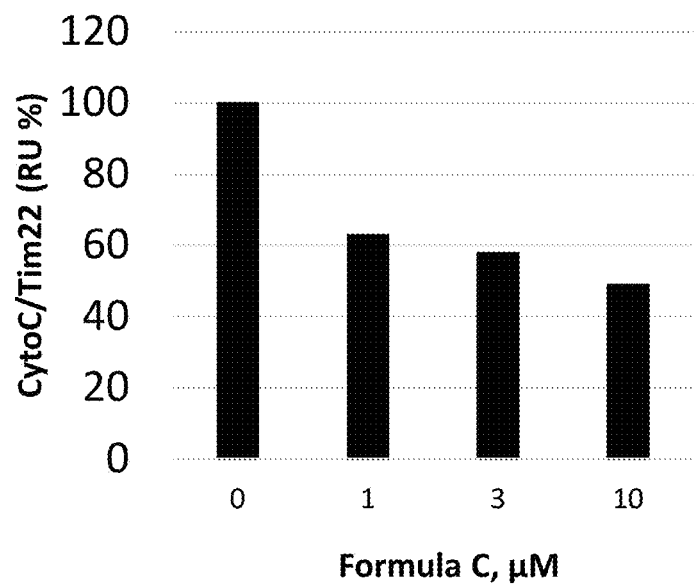
FIG. 3A. Apoptosis induction by Formula C in vitro activity. Semi-quantification of cytochrome C in Western Blot of the mitochondrial fraction following 2 hr treatment.

In another embodiment, the present invention provides a method of inducing apoptosis in a cancer cell comprising administering to one or more cells a composition comprising a compound that promotes the detachment of HK2 from mitochondria. In one embodiment, such a method is demonstrated herein and in FIG. 3.

In another embodiment, the present invention provides a method for the reduction of cytochrome C levels in a cancer cell comprising administering to one or more cells a composition comprising a compound that promotes the detachment of HK2 from mitochondria. In one embodiment, such a method is demonstrated herein and in FIG. 3A.

In another embodiment, the present invention provides a method for increasing cellular levels of cleaved caspase-3 in a cancer cell comprising administering to one or more cells a composition comprising a compound that promotes the detachment of HK2 from mitochondria. In one embodiment, such a method is demonstrated herein and in FIG. 3B.

In another embodiment, the present invention provides a method for reducing proliferation of cancer cells in a cancer cell comprising administering to one or more cells a composition comprising a compound that promotes the detachment of HK2 from mitochondria. In one embodiment, such a method is demonstrated herein and in FIG. 3C.

In another embodiment, the present invention provides a method for method of reducing mitotic index in a cancer cell comprising administering to one or more cells a composition comprising a compound that promotes the detachment of HK2 from mitochondria. In one embodiment, such a method is demonstrated herein and in FIG. 6A.

In another embodiment, the present invention provides a method of determining the efficacy of a cancer therapy in a subject with an HK2-expressing tumor comprising the step of contacting one or more cells of said subject with a therapeutically effective amount of a compound that promotes the detachment of Hexokinase 2 (HK2) from the mitochondria. In one embodiment, the compound is a jasmonate derivative, as described herein. In another embodiment, the compound is a piperazine derivative, as described herein.

In one embodiment, the term "hexokinase-2 (HK2)-expressing" as used herein may be replaced with the term "PET-positive" or "FDG-PET-positive." For example, the present invention also provides methods of treating, inhibiting or suppressing an FDG-PET-positive cancer or tumor in a subject comprising the step of contacting one or more cells of said subject with a therapeutically effective amount of a compound as described herein.

In another embodiment, an HK2-expressing cancer or tumor may be detected by evaluating HK2 mRNA levels, HK2 protein levels, or HK2 activity in a tissue sample from a subject.

In one embodiment, a subject as described herein has cancer. In one embodiment, the term "cancer" in the context of the present invention includes all types of neoplasm whether in the form of solid or non-solid tumors, and includes both malignant and premalignant conditions as well as their metastasis.

In one embodiment, a subject as described herein has a pre-cancerous condition. In another embodiment, a subject as described herein has a benign hyperproliferative disorder. In another embodiment, said subject has cancer.

In one embodiment, the term "pre-cancer" or "pre-malignant" as used herein interchangeably refers to diseases, syndromes or other conditions associated with an increased risk of cancer. Pre-cancer conditions in the context of the present invention include, but are not limited to: breast calcifications, vaginal intra-epithelial neoplasia, Barrett's esophagus, atrophic gastritis, dyskeratosis congenital, sideropenic dysphagia, lichen planus, oral submucous fibrosis, actinic keratosis, solar elastosis, cervical dysplasia, leukoplakia and erythroplakia.

In one embodiment, the term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting example of benign hyperproliferative disorder are psoriasis and benign prostatic hyperplasia (BPH).

In one embodiment, the cancer comprises a carcinoma, sarcoma, myeloma, leukemia, or lymphoma.

In one embodiment, the cancer comprises a cancer of epithelial origin. In one embodiment, the carcinoma comprises an adenocarcinoma. In another embodiment, the carcinoma comprises a squamous cell carcinoma. In another embodiment, the carcinoma comprises a lung carcinoma. In one embodiment, the lung carcinoma comprises small cell lung carcinoma, non-small cell lung carcinoma, or large cell lung carcinoma. In another embodiment, the carcinoma comprises squamous cell carcinoma, basal cell carcinoma, or a combination thereof.

In one embodiment, the cancer comprises a sarcoma. In one embodiment, the sarcoma comprises osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); and Mesenchymous or mixed mesodermal tumor (mixed connective tissue types).

In one embodiment, the subject has a myeloma, which, in one embodiment, is cancer that originates in the plasma cells of bone marrow. The plasma cells produce some of the proteins found in blood.

In one embodiment, the cancer comprises a hematological malignancy. In one embodiment, the hematological malignancy comprises leukemia.

In one embodiment, leukemia (or "non-solid tumor" or "blood cancer" or "liquid tumor") comprises a cancer of the bone marrow, which in one embodiment, comprises the site of blood cell production. In one embodiment, leukemia comprises myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); and Polycythemia vera or erythremia (malignancy of various blood cell products, but with red cells predominating). In one embodiment, the leukemia comprises lymphoblastic leukemia.

In another embodiment, the subject has a lymphoma. In one embodiment, lymphomas develop in the glands or nodes of the lymphatic system, a network of vessels, nodes, and organs (in one embodiment, the spleen, tonsils, and thymus) that purify bodily fluids and produce lymphocytes, which, in one embodiment, comprise infection-fighting white blood cells. In one embodiment, lymphomas are "solid cancers." In another embodiment, a lymphoma may occur in a specific organ such as the stomach, breast or brain. In one embodiment such a lymphoma is an extranodal lymphoma.

In one embodiment, a lymphoma described herein may comprise a Hodgkin lymphoma or a Non-Hodgkin lymphoma. In one embodiment, the presence of Reed-Sternberg cells in Hodgkin lymphoma diagnostically distinguishes Hodgkin lymphoma from Non-Hodgkin lymphoma.

In one embodiment, a subject as described herein comprises a Mixed Type cancer. In one embodiment, a mixed type cancer comprises several types of cells. In one embodiment, the type components may be within one category or from different categories. In one embodiment a Mixed Type cancer comprises adenosquamous carcinoma, mixed mesodermal tumor, carcinosarcoma, teratocarcinoma, or a combination thereof.

As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, lung cancer, bone cancer, liver cancer, stomach cancer, bladder cancer, colon cancer, colorectal cancer, pancreatic cancer, cancer of the thyroid, head and neck cancer, cancer of the central nervous system, brain cancer, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, Leiomyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

In one embodiment, the cancer comprises a prostate cancer. In one embodiment, the prostate cancer comprises castration-resistant prostate cancer. In another embodiment, the prostate cancer comprises acinar adenocarcinoma, which in one embodiment develops in the gland cells that line the prostate gland and in one embodiment, is the most common type of prostate cancer. In another embodiment, the prostate cancer comprises In another embodiment, the prostate cancer comprises In another embodiment, the prostate cancer comprises In another embodiment, the prostate cancer comprises In another embodiment, the prostate cancer comprises In another embodiment, the prostate cancer comprises Ductal adenocarcinoma, Transitional cell (or urothelial) cancer, Squamous cell cancer, Small cell prostate cancer, prostate carcinoid, or prostate sarcoma.

In another embodiment, the cancer is an adenocarcinoma of the stomach or gastroesophageal junction, Dermatofibrosarcoma protuberans, Endocrine/neuroendocrine tumors, Gastrointestinal stromal tumor, Giant cell tumor of the bone, Kaposi sarcoma, Myelodysplastic/myeloproliferative disorders, Ovarian epithelial/fallopian tube/primary peritoneal cancers, Soft tissue sarcoma, Systemic mastocytosis, Germ cell tumor, or a combination thereof.

Cutaneous T-Cell Lymphoma (CTCL)

In one embodiment, the present invention provides a method of treating or suppressing cutaneous T-cell lymphoma (CTCL) in a subject; inhibiting the proliferation of CTCL cells in a subject; inducing apoptosis of CTCL cells; potentiating the immune response to CTCL cells; or determining the efficacy of a cancer therapy in a subject with CTCL comprising the step of contacting one or more cells of said subject with a therapeutically effective amount of a jasmonate derivative as described herein.

In one embodiment, a subject as described herein has been diagnosed with a lymphoma. In one embodiment, lymphomas develop in the glands or nodes of the lymphatic system, a network of vessels, nodes, and organs (in one embodiment, the spleen, tonsils, and thymus) that purify bodily fluids and produce lymphocytes, which, in one embodiment, comprise infection-fighting white blood cells. In one embodiment, lymphomas are "solid cancers." In another embodiment, a lymphoma may occur in a specific organ such as the stomach, breast or brain. In one embodiment such a lymphoma comprises an extranodal lymphoma.

In one embodiment, a lymphoma described herein may comprise a Hodgkin lymphoma or a Non-Hodgkin lymphoma. In one embodiment, the presence of Reed-Sternberg cells in Hodgkin lymphoma diagnostically distinguishes Hodgkin lymphoma from Non-Hodgkin lymphoma.

In one embodiment, the lymphoma comprises a cutaneous T-cell lymphoma (CTCL). In one embodiment, CTCL occurs when T cells become cancerous. In one embodiment, CTCL affect the skin, causing different types of skin lesions.

In one embodiment, the CTCL comprises Mycosis fungoides. In one embodiment, Mycosis fungoides or Alibert-Bazin syndrome or granuloma fungoides, is the most common form of cutaneous T-cell lymphoma. It generally affects the skin, but may progress internally over time. In another embodiment, the CTCL comprises Sézary syndrome. In one embodiment, Sézary syndrome is an aggressive form of CTCL.

In one embodiment, the present invention provides a method of treating CTCL in a subject comprising the step of contacting one or more cells of said subject with a therapeutically effective amount of a compound as described herein.

In one embodiment, the present invention provides a method of suppressing CTCL in a subject comprising the step of contacting one or more cells of said subject with a therapeutically effective amount of a compound as described herein.

In one embodiment, the present invention provides a method of inhibiting CTCL in a subject comprising the step of contacting one or more cells of said subject with a therapeutically effective amount of a compound as described herein.

In another embodiment, the present invention provides a method of inhibiting anchorage independent growth of CTCL cells in a subject comprising the step of contacting one or more cells of said subject with a therapeutically effective amount of a compound as described herein.

In another embodiment, the present invention provides a method of inhibiting the proliferation of CTCL cells in a subject comprising the step of contacting one or more cells of said subject with a therapeutically effective amount of a compound as described herein.

In another embodiment, the present invention provides a method of decreasing CTCL cell viability in a subject comprising the step of contacting one or more cells of said subject with a therapeutically effective amount of a compound as described herein.

In another embodiment, the present invention provides a method of inducing apoptosis of CTCL cells in a subject, said method comprising the step of contacting one or more cells of said subject with a therapeutically effective amount of a compound as described herein.

In another embodiment, the present invention provides a method of chemoprevention of CTCL in a subject in need thereof by contacting one or more cells of said subject with a therapeutically effective amount of a compound as described herein.

In another embodiment, the present invention provides a method of potentiating the immune response to CTCL cells in a subject comprising the step of contacting one or more cells of said subject with a therapeutically effective amount of a compound as described herein.

In another embodiment, the present invention provides a method of inducing cell growth arrest of CTCL cells in a subject, said method comprising the step of contacting one or more cells of said subject with a therapeutically effective amount of a compound as described herein.

In another embodiment, the present invention provides a method of inducing terminal differentiation of CTCL cells in a subject comprising the step of contacting one or more cells of said subject with a therapeutically effective amount of a compound as described herein.

In another embodiment, the present invention provides a method of inducing differentiation of CTCL cells in a subject having CTCL, said method comprising the step of contacting one or more cells of said subject with a therapeutically effective amount of a compound as described herein.

In one embodiment, a subject as described herein is afflicted with mixed type cancer, which in one embodiment, comprises several types of cells. In one embodiment, the type components may be within one category or from different categories. In one embodiment a Mixed Type cancer comprises CTCL cells as well as other types of cancer cells.

In one embodiment, CTCL comprises any type of CTCL known in the art as well as metastases thereof.

Other Cancers

Peripheral T-cell lymphomas (PTCL) are a second type of NHL and originate from mature or peripheral (not central or thymic) T-cell lymphocytes as a clonal proliferation from a single T-cell and are usually either predominantly nodal or extranodal tumors. They have T-cell lymphocyte cell-surface markers and clonal arrangements of the T-cell receptor genes.

Thus, in one embodiment, any of the methods of the present invention as described herein may be used for a subject with PTCL or on PTCL cells as described herein comprising the step of contacting one or more cells of said subject with a therapeutically effective amount of a compound as described herein.

In one embodiment, methods described herein comprise, inter alia, treating; suppressing; inhibiting; inhibiting anchorage independent growth of cells; inhibiting the proliferation of cells; inducing apoptosis of cells; chemoprevention; potentiating the immune response to cells; inducing cell growth arrest of cells, decreasing cell viability, etc.

In another embodiment, any of the methods of the present invention as described herein may be used for a subject with squamous cell carcinoma or on squamous cell carcinoma cells as described herein comprising the step of contacting one or more cells of said subject with a therapeutically effective amount of a compound as described herein. In one embodiment, the squamous cell carcinoma is squamous cell lung cancer.

Cancer Stage

In one embodiment, any of the methods of the present invention as described herein may be used for a subject with cancer at any stage. In one embodiment, the cancer is poorly differentiated. In another embodiment, the cancer is moderately differentiated. In another embodiment, the cancer is well differentiated.

Determination of HK2 Levels and Activity

In one embodiment, the present invention provides a method of treating a subject with an HK2-expressing cancer or tumor.

In another embodiment, the present invention provides a method of treating cancer in a subject comprising the steps of: identifying a subject suspected of having cancer; evaluating HK2 levels in the cells of said subject; and, if said cells comprise high levels of HK2, treating said subject with a compound or composition of the present invention, either alone or in combination with other treatments described herein and known in the art, thereby treating said subject with cancer.

In another embodiment, the present invention provides a method of treating a subject with CTCL comprising the steps of: performing an assay on a subject suspected of having CTCL to detect HK2 levels in the subject and, if HK2 levels are high, treating said subject with a compound or composition of the present invention, either alone or in combination with other treatments described herein and known in the art, thereby treating said subject with said HK2-expressing cancer or tumor.

In another embodiment, the present invention provides a method of inhibiting tumor growth or cancer spread in a subject comprising the steps of: identifying a subject suspected of having cancer; evaluating HK2 levels in the cells of said subject; and, if said cells comprise high levels of HK2, treating said subject with a compound or composition of the present invention, either alone or in combination with other treatments described herein and known in the art, thereby inhibiting tumor growth or cancer spread in said subject.

In another embodiment, the present invention provides a method of suppressing tumor growth or cancer spread in a subject comprising the steps of: identifying a subject suspected of having cancer; evaluating HK2 levels in the cells of said subject; and, if said cells comprise high levels of HK2, treating said subject with a compound or composition of the present invention, either alone or in combination with other treatments described herein and known in the art, thereby suppressing tumor growth or cancer spread in said subject.

In another embodiment, any of the methods of the present invention further comprise the step of determining the HK2 levels in a subject. In one embodiment, HK2 levels are determined in a sample from the subject. In one embodiment, the sample comprises a tissue biopsy. In one embodiment, HK2 levels in a tumor are determined. In another embodiment, HK2 levels in a specific tissue are determined. In one embodiment, HK2 levels are determined by biopsy. In one embodiment, the biopsy comprises a major surgical biopsy, which in one embodiment, is an excisional or open biopsy. In another embodiment, HK2 levels are determined by fine needle aspiration (FNA), or fine-needle aspiration cytology (FNAC). In one embodiment, FNA is performed with a thin (in one embodiment, 23-25 gauge), hollow needle. In one embodiment, the biopsy or aspirate is subjected to a cytological exam. In another embodiment, the biopsy or aspirate is subjected to a histological exam.

The first committed step in glucose metabolism is the ATP-dependent conversion of glucose to glucose-6-phosphate (G6P), which is catalyzed by hexokinases (HKs). In mammals, there are four hexokinase isoforms, HK1, HK2, HK3, and HK4 (also known as glucokinase), encoded by separate genes. While HK1, HK2, and HK3 have high affinity for glucose, HK4 has low affinity for glucose and its expression is restricted to the pancreas and liver. HK3 is usually expressed at low levels and is inhibited in physiological concentrations of glucose. HK1 and HK2 are unique in their ability to bind the outer mitochondrial membrane (OMM). They are structurally and functionally similar to one another and both are inhibited by their catalytic product glucose-6-phosphate (G6P).

Both HK1 and HK2 are highly expressed in embryonic tissues. HK1 is ubiquitously expressed in the majority of adult tissues, while HK2 is expressed at relatively high levels only in adipose tissues, skeletal muscles, and heart. Despite its absence or low expression in the majority of adult normal cells, HK2 is expressed at high levels in many cancer cells, such as lung, breast, and colon cancer. In contrast, HK2 expression in normal lung and mammary gland is undetectable. Thus, HK2 expression distinguishes cancer cells from normal cells.

HK2 gene expression can be induced by factors such as insulin, hypoxia, cold temperatures, and exercise, indicating HK2's adaptive role in metabolic responses to changes in the cellular environment.

HK2 is highly elevated in rapidly growing cancers and is required for oncogenic transformation and for tumor initiation in some cancer models. Furthermore, inhibition of HK2 improves the efficacy of anticancer drugs.

HK2 phosphorylates glucose and effectively prevents glucose from leaving the cell and thus commits glucose to metabolism. Moreover, the localization and attachment of HK2 to the OMM promotes the coupling of glycolysis to mitochondrial oxidative phosphorylation, which enhances ATP production, while rapidly producing biomass for growth and proliferation, thereby meeting the cell's energy and growth demands. Specifically, HK2 binds to mitochondrial voltage dependent anion channels (VDAC). When bound to VDAC, HK2 is not inhibited by its product, i.e., G6P, and consequently, glycolysis is elevated.

In one embodiment, HK2 levels are detected in the subject by evaluating the activity of HK2, which in one embodiment, comprises evaluating the rate of glucose metabolism in the subject.

In one embodiment, the rate of glucose metabolism is determined using radiolabeled glucose. In one embodiment, the tracer used in the PET scan is fluorodeoxyglucose (FDG), which in one embodiment is an analogue of glucose that is labeled with fluorine-18. It has been demonstrated that tissue uptake of FDG as detected by PET is well correlated with hexokinase activity (Fukunaga et al., J Nucl Med. 1998 June; 39(6): 1002-7, which is incorporated herein by reference in its entirety). In another embodiment, the tracer is rubidium-82. In another embodiment, other radionuclides known in the art may be used.

Upon entering cancer cells, FDG, a radiolabeled glucose analog, is phosphorylated by mitochondrial bound HK2. This yields FDG-6-phosphate that is not further metabolized and thus accumulates in much higher levels than in normal cells. FDG is labeled with the 18-fluorine radioisotope that decays, emitting a positron. This then annihilates with an electron giving two gamma-photons that are detected by a detector.

Thus, in one embodiment, a positive FDG-PET scan of tumors in vivo is an indication of high HK2 expression in tumor cells because while glucose (or FDG) entry through glucose transporters is generally reversible, intracellular retention of glucose or FDG is dependent on phosphorylation of glucose transporters by HK2.

In one embodiment, the present invention provides a method as described herein comprising the step of performing a fluorodeoxyglucose (FDG)-PET scan on a subject suspected of having an HK2-expressing cancer; identifying a HK2-expressing cancer or tumor in said subject on said FDG-PET scan, wherein said steps are performed prior to the step as described herein comprising contacting one or more cells of said subject with a therapeutically effective amount of a compound that promotes the detachment of HK2 from the mitochondria. In one embodiment, the HK2-expressing cancer or tumor comprises CTCL. In one embodiment, the compound is a compound represented by the structure of Formula (VII) as described herein. In another embodiment, the compound is a compound represented by the structure of Formula (II) as described herein.

In one embodiment, the present invention provides a method of determining the efficacy of a cancer therapy in a subject with an HK2-expressing cancer or tumor comprising the steps of: (a) performing a first fluorodeoxyglucose (FDG)-PET scan on said subject; (b) identifying said HK2-expressing tumor in said subject on said FDG-PET scan; (c) administering to said subject a therapeutically effective amount of a compound that promotes the detachment of HK2 from the mitochondria. In one embodiment, the HK2-expressing tumor comprises CTCL. In one embodiment, the compound is a compound represented by the structure of Formula (VII) as described herein. In another embodiment, the compound is a compound represented by the structure of Formula (II) as described herein.

In another embodiment, the present invention provides a method of evaluating the efficacy of a cancer therapy with Formula (VII) or Formula (II) in a subject with a tumor comprising the steps of (a) performing a first fluorodeoxyglucose (FDG)-positron emission tomography (PET) scan on said subject; (b) identifying an HK2-expressing tumor in said subject on said FDG-PET scan; (c) administering to said subject a therapeutically effective amount of a compound as described herein; and (d) performing a second FDG-PET scan on said subject, wherein if said HK2-expressing tumor is decreased in said second FDG-PET compared to said first FDG-PET, then said cancer therapy was efficacious in said subject. In one embodiment, the HK2-expressing tumor comprises CTCL.

In one embodiment, about 10 to about 20 mCi, e.g., about 10 mCi, about 11 mCi, about 12 mCi, about 13 mCi, about 14 mCi, about 15 mCi, about 16 mCi, about 17 mCi, about 18 mCi, about 19 mC or about 20 mCi of radiolabeled glucose is administered to the subject. In one embodiment, radiolabeled glucose is administered to the subject via intravenous injection.

In one embodiment, the detector of glucose metabolism rate comprises a PET scan. In one embodiment, the detection of radiolabeled glucose is performed about 75 minutes after administration of the radiolabeled glucose to the subject. In one embodiment, the PET scan conducted on a part of the subject's body. In another embodiment, the PET scan is conducted on the whole body of the subject, which in one embodiment, is from skull base to proximal femurs.

In one embodiment, positron emission tomography (PET) comprises a nuclear medicine imaging technique which produces an image or picture (e.g., in 3 dimensions) of functional processes in the body. The system detects pairs of gamma rays emitted indirectly by a positron-emitting radionuclide (tracer), which is introduced into the body on a biologically active molecule. Images of tracer concentration (e.g., in 3-dimensional space) within the body can be reconstructed by computer analysis.

In one embodiment, a PET scan is used in conjunction with another scan, such as a computed tomography (CT) scan or a magnetic resonance imaging (MRI) scan, as known in the art.

In one embodiment, the additional scan(s) is performed on the patient during the same session, in the same machine.

In one embodiment, CT uses x-rays and a computer to make an image of sections (organs, bones, and tissues) of a subject's body. For a CT scan, the subject will, generally, receive a contrast enhancing agent by intravenous line (IV), which helps produce a clearer image.

A PET/CT is an imaging tool combines two different types of imaging into a single procedure. Typically, a PET image is color coded—different colors show various levels of cell activity. A CT scan shows the exact locations of the body's organs and also can show abnormal growths. When a CT scan is laid over a PET scan, a clinician or doctor can pinpoint the exact location of the PET-detected activity (e.g., tumoral FDG metabolism). They can also see the level and extent of that activity. Even when an abnormal growth is not yet visible on a CT scan, the PET scan can show the abnormal cell activity.

In another embodiment, the present invention provides a method of evaluating the efficacy of therapy with a compound that promotes the detachment of HK2 from the mitochondria in a subject with a tumor comprising the steps of: (a) performing a first evaluation of HK2 levels in said tumor in said subject; (b) administering to said subject a therapeutically effective amount of a compound as described herein; and (c) performing a second evaluation of HK2 levels in said tumor in said subject, wherein if said tumor comprises decreased levels of HK2 in said second evaluation compared to said first evaluation, then said cancer therapy was efficacious in said subject. In one embodiment, the activity levels of HK2 are evaluated. In one embodiment the HK2 activity levels are evaluated via fluorodeoxyglucose (FDG)-positron emission tomography (PET) scan. In another embodiment, gene expression levels of HK2 are evaluated. In one embodiment, HK2 gene expression levels are evaluated via microarrays or RNA-seq. In another embodiment, protein levels of HK2 are evaluated. In one embodiment, the compound that promotes the detachment of HK2 from the mitochondria comprises a compound of Formula (VII). In another embodiment, the compound that promotes the detachment of HK2 from the mitochondria comprises a compound of Formula (II).

In another embodiment, the present invention provides a method of determining the efficacy of a cancer therapy in a subject with an HK2-expressing tumor comprising the steps of: (a) performing a first evaluation of HK2 levels in said HK2-expressing tumor in said subject; (b) administering to said subject a therapeutically effective amount of a compound that promotes the detachment of HK2 from the mitochondria; and (c) performing a second evaluation of HK2 levels in said HK2-expressing tumor in said subject, wherein if said tumor comprises decreased levels of HK2 in said second evaluation compared to said first evaluation, then said cancer therapy was efficacious in said subject. In one embodiment, the compound is a compound represented by the structure of Formula (VII). In another embodiment, the compound is a compound represented by the structure of Formula (II).

In another embodiment, the present invention provides methods relating to personalized medicine. In one embodiment, the present invention provides a method of selecting a subject having a tumor that is likely to benefit from an HK2 detachment treatment comprising the steps of: (a) evaluating HK2 levels in a tumor in a subject; and (b) administering a therapeutically effective amount of a compound that promotes the detachment of HK2 from the mitochondria to said subject if HK2 levels in said tumor are high. In another embodiment, the present invention provides a method of selecting a subject that is likely to benefit from an HK2 detachment treatment comprising the steps of: (a) performing a fluorodeoxyglucose (FDG)-PET scan on said subject; and (b) identifying an HK2-expressing tumor in said subject on said FDG-PET scan; wherein treatment with said compound is administered to said subject if said tumor expresses high levels of HK2.

In one embodiment, HK2 levels are detected using protein detection techniques in a sample from the subject. In one embodiment, such protein detection techniques comprise Western Blots, immunohistochemistry, ELISA, or other methods known in the art.

In another embodiment, HK2 levels are detected using gene expression detection techniques in a sample from the subject. In one embodiment, the gene expression detection technique comprises a hybridization-based technique, such as a microarray, Northern blot analysis, nuclease protection assays (NPA), in situ hybridization, reverse transcription-polymerase chain reaction (RT-PCR), or other methods known in the art. In another embodiment, the gene expression detection technique comprises a sequencing based technique, such as Next Generation RNA sequencing (i.e., RNA-Seq, whole transcriptome shotgun sequencing (WTSS)) or other methods known in the art. In one embodiment, the detection technique comprises a bulk detection technique. In another embodiment, the detection technique comprises a single cell detection technique, such as single-cell RNA-seq (scRNA-seq).

In another embodiment, the present invention provides a method of determining the efficacy of a cancer therapy in a subject with an HK2-expressing tumor comprising the steps of: performing a first evaluation of glucose metabolism in one or more tissues of a subject suspected of comprising a tumor; treating said subject with a cancer therapy; and performing a second evaluation of glucose metabolism time in the same one or more tissues that were evaluated in said first evaluation; wherein increased glucose metabolism is an indicator of an HK2-expressing tumor. In one embodiment, if glucose metabolism is decreased in the second evaluation compared to the first evaluation, then said cancer therapy was efficacious in said subject. In one embodiment, the cancer therapy comprises treatment with a compound as described herein as described herein.

In one embodiment, the second evaluation of glucose metabolism is performed about 7-14 days after the treatment with a compound as described herein. In another embodiment, the second evaluation of glucose metabolism is performed about 7-10 days, 1 day, 2 days, 3 days, 4 days, 5 days, 6 days, 7 days, 8 days, 9 days, 10 days, 11 days, 12 days, 13 days or 14 days after the treatment with a compound as described herein. In another embodiment, the second evaluation of glucose metabolism is performed about 14-60 days, 1-6 months, or 2 months to one year after the treatment with a compound as described herein. In one embodiment, the second evaluation of glucose metabolism is performed prior to the administration of a second dose of the compound as described herein. In one embodiment, the compound is a compound represented by the structure of Formula (VII) as described herein. In another embodiment, the compound is a compound represented by the structure of Formula (II) as described herein.

In one embodiment, HK2 levels that are significantly increased compared to non-diseased tissue are an indication of an HK2-expressing tumor or cancer. In another embodiment, HK2 levels that are significantly increased compared to average HK2 levels in that tissue in healthy patients, as known in the art, are an indication of an HK2-expressing tumor or cancer. In one embodiment, a significant increase in HK2 levels is more than 50% compared to a control, non-diseased tissue. In another embodiment, a significant increase in HK2 levels is more than 75% compared to a control, non-diseased tissue. In another embodiment, a significant increase in HK2 levels is more than 25%, more than 10%, more than 20%, more than 30%, more than 40%, more than 60%, more than 70%, more than 80%, more than 90%, or more than 100%. In another embodiment, a significant increase in HK2 levels is more than approximately 25-75%, 50-75% or 50-100%.

In an embodiment of the invention, a significant change in glucose (e.g., FDG) metabolism is any measurable amount of decrease that would be recognized by a practitioner of ordinary skill in the art, under the circumstances and in view of the particularities of the patient or subject's clinical state, would recognize as significant. In one embodiment of the invention, a significant decrease is between about 15% and about 25% (e.g., about 15-20%, about 15-25%, about 20-25%, about 15%, about 16%, about 17%, about 18%, about 19%, about 20%, about 21%, about 22%, about 23%, about 24%, about 25%).

The magnitude of radioactivity (e.g., when using an FDG marker) in a tumor cell can be converted from PET signal to absolute radiation units (e.g., using methods commonly known in the art) when evaluating whether a decrease of glucose metabolism has occurred. Alternatively, arbitrary units of PET signal are merely compared when determining whether a decrease in glucose metabolism has occurred. In an embodiment of the invention, tumor-to-background ratios of FDG uptake are compared when making a determination as to whether a decrease of glucose metabolism has occurred.

In one embodiment, a decreased tumor comprises decreased tumor size, decreased HK2 expression, or absence of HK2 expression. In another embodiment, efficacy in stopping tumor growth and spread is evaluated as described hereinabove.

In one embodiment, the cancer therapy comprises a compound or composition of the present invention, either alone or in combination with other treatments described herein or known in the art.

Combined Treatments

In another embodiment, any of the methods of the present invention further comprise the step of contacting one or more cells of said subject with an anti-cancer treatment.

As described hereinabove, in one embodiment, methods of the present invention further comprise the step of contacting one or more cells of said subject with a therapeutic agent. In one embodiment, the therapeutic agent is administered prior to administration the compound as described herein. In another embodiment, the therapeutic agent is administered concurrently with the compound represented by the structure as described herein. In another embodiment, the therapeutic agent is administered after administration the compound as described herein. In one embodiment, the compound is the compound represented by the structure of Formula (VII). In another embodiment the compound is the compound represented by the structure of Formula (II), which in one embodiment comprises the compounds of Formula (20-24).

In one embodiment, the anti-cancer treatment is radiotherapy.

In another embodiment, the anti-cancer treatment comprises an anti-cancer drug. In one embodiment, the anti-cancer drug comprises a chemotherapeutic.

In one embodiment, the chemotherapeutic comprises 5-fluorouracil, Bleomycin, capecitabine, cisplatin, Cyclophosphamide, dacarbazine, Doxorubicin, Epirubicin, etoposide, folinic acid, Methotrexate, Mustine, oxaliplatin, prednisolone, procarbazine, vinblastine, vincristine, or a combination thereof.

In another embodiment, the present invention provides a method of treating, inhibiting, or suppressing a cancer or tumor in a subject comprising contacting one or more cells of said subject with a compound as described herein and a targeted therapy. In one embodiment, the compound is a compound represented by the structure of Formula (VII) as described herein. In another embodiment, the compound is a compound represented by the structure of Formula (II) as described herein.

Targeted Therapies

In one embodiment, the present invention provides methods of treating cancer comprising administering a compound as described herein in combination with one or more targeted therapies. In one embodiment, the compound is a compound represented by the structure of Formula (VII) as described herein. In another embodiment, the compound is a compound represented by the structure of Formula (II) as described herein.

In one embodiment, the immunotherapeutic compound is targeted to particular molecules expressed abnormally by cancer cells. In one embodiment, the targeted therapy comprises a hormone therapy, signal transduction inhibitor, gene expression modulator, apoptosis inducer, angiogenesis inhibitor, immunotherapy, or toxin delivery molecules.

In one embodiment, the targeted therapy utilizes small molecules. In another embodiment, the targeted therapy utilizes antibodies, which, in one embodiment, are monoclonal antibodies.

In one embodiment, the immunotherapeutic compound comprises abiraterone acetate (Zytiga®), ado-trastuzumab emtansine (Kadcyla®), afatinib dimaleate (Gilotrif®), alectinib (Alecensa®), alemtuzumab (Campath®), Alitretinoin (Panretin®), anastrozole (Arimidex®), Atezolizumab (Tecentriq™), axitinib (Inlyta®), belinostat (Beleodaq®), Bevacizumab (Avastin®), bexarotene (Targretin®), blinatumomab (Blincyto®), bortezomib (Velcade®), bosutinib (Bosulif®), brentuximab vedotin (Adcetris®), Cabazitaxel (Jevtana®), cabozantinib (Cabometyx™), Cabozantinib (Cometriq®), carfilzomib (Kyprolis®), ceritinib (LDK378/Zykadia™), Cetuximab (Erbitux®), cobimetinib (Cotellic™), crizotinib (Xalkori®), dabrafenib (Tafinlar®), daratumumab (Darzalex™), dasatinib (Sprycel®), denileukin diftitox (Ontak®), Denosumab (Xgeva®), Dinutuximab (Unituxin™), elotuzumab (Empliciti™), enzalutamide (Xtandi®), Erlotinib (Tarceva®), everolimus (Afinitor®), exemestane (Aromasin®), fulvestrant (Faslodex®), gefitinib (Iressa®), Ibritumomab tiuxetan (Zevalin®), ibrutinib (Imbruvica®), idelalisib (Zydelig®), Imatinib mesylate (Gleevec®), Ipilimumab (Yervoy®), ixazomib citrate (Ninlaro®), Lanreotide acetate (Somatuline® Depot), lapatinib (Tykerb®), lenvatinib mesylate (Lenvima®), letrozole (Femara®), necitumumab (Portrazza™), nilotinib (Tasigna®), nivolumab (Opdivo®), obinutuzumab (Gazyva®), ofatumumab (Arzerra®), olaparib (Lynparza™), olaratumab (Lartruvo™), osimertinib (Tagrisso™), palbociclib (Ibrance®), panitumumab (Vectibix®), panobinostat (Farydak®), pazopanib (Votrient®), pembrolizumab (Keytruda®), pertuzumab (Perjeta®), pralatrexate (Folotyn®), radium 223 dichloride (Xofigo®), ramucirumab (Cyramza®), regorafenib (Stivarga®), rituximab (Rituxan®), romidepsin (Istodax®), ruxolitinib phosphate (Jakafi®), siltuximab (Sylvant®), sonidegib (Odomzo®), sorafenib (Nexavar®), sunitinib (Sutent®), tamoxifen (Nolvadex), temsirolimus (Torisel®), toremifene (Fareston®), trametinib (Mekinist®), Trastuzumab (Herceptin®), Tretinoin (Vesanoid®), vandetanib (Caprelsa®), vemurafenib (Zelboraf®), venetoclax (Venclexta™), Vismodegib (Erivedge®), vorinostat (Zolinza®), ziv-aflibercept (Zaltrap®), or a combination thereof.

In another embodiment, methods of the present invention further comprise the step of contacting one or more cells of the subject with an immunotherapeutic compound.

Immunotherapeutic Compounds

In one embodiment, an immunotherapy as described herein comprises a monoclonal antibody that recognizes specific molecules on the surface of cancer cells. In one embodiment, binding of the monoclonal antibody to the target molecule results in the immune destruction of cells that express that target molecule. In another embodiment, the antibody binds to certain immune cells to enhance their actions on cancer cells.

In one embodiment, the immunotherapeutic compound comprises imatinib or trastuzumab.

In one embodiment, the immunotherapeutic compound comprises a checkpoint inhibitor.

In one embodiment, the checkpoint inhibitor comprises a Programmed cell Death protein 1(PD1) inhibitor or a Programmed cell Death Ligand 1 (PD-L1) inhibitor.

In one embodiment, the PD-1 or PD-L1 inhibitor is an antibody.

In one embodiment, the antibody comprises Nivolumab, Pembrolizumab, Pidilizumab, Avelumab, BMS 936559, or MPDL3280A.

Chimeric Antigen Receptor-Expressing T-Cells (CAR T-Cells)

In one embodiment, the immunotherapeutic compound comprises chimeric antigen receptor T cells (CAR T-cells).

In another embodiment, an immunotherapy as described herein comprises adoptive cell transfer (ACT) therapy. In one embodiment, ACT therapy comprises cytotoxic T-cells from a patient or donor that are engineered to express a chimeric antigen receptor (CAR T-cells) targeted to a tumor specific antigen expressed on the surface of the tumor cells. These CAR T-cells are then cytotoxic only to cells expressing the tumor specific antigen.

In one embodiment, chimeric antigen receptors (CARs) are a type of antigen-targeted receptor composed of intracellular T-cell signaling domains fused to extracellular tumor-binding moieties, most commonly single-chain variable fragments (scFvs) from monoclonal antibodies.

CARs directly recognize cell surface antigens, independent of MHC-mediated presentation, permitting the use of a single receptor construct specific for any given antigen in all patients.

In one embodiment, a CAR T-cell comprises an immunoresponsive cell comprising an antigen receptor, which is activated when its receptor binds to its antigen.

In one embodiment, the CAR T-cells used in the compositions and methods as disclosed herein comprise antigen-recognition domains fused to the CD3 activation chain of the T-cell receptor (TCR) complex. In another embodiment, the CAR T-cells used in the compositions and methods as disclosed herein comprise secondary costimulatory signals in tandem with CD3, including, in one embodiment, intracellular domains from CD28 or a variety of TNF receptor family molecules such as CD27, 4-1BB (CD137), OX40 (CD134), or a combination thereof. In another embodiment, the CAR T-cells used in the compositions and methods as disclosed herein comprise two costimulatory signals in addition to CD3ζ. In one embodiment, the two costimulatory signals comprise CD28 and 4-1BB or OX-40, or a combination thereof. In another embodiment, the signaling domain comprises the CD3ζ-chain, CD97, GDI 1a-CD18, CD2, ICOS, CD27, CD154, CDS, OX40, 4-1BB, CD28 signaling domain, or combinations thereof.

In one embodiment, CAR-modified T-cell potency may be further enhanced through the introduction of additional genes, including those encoding proliferative cytokines (ie, IL-12) or costimulatory ligands (ie, 4-1BBL), thus producing "armored" fourth-generation CAR-modified T-cells. In one embodiment, "armored CAR T-cells," are CAR T-cells which are protected from the inhibitory tumor microenvironment. In another embodiment, the "armored" CAR technology incorporates the local secretion of soluble signaling proteins to amplify the immune response within the tumor microenvironment with the goal of minimizing systemic side effects. In one embodiment, the signaling protein signal comprises IL-12, which can stimulate T-cell activation and recruitment. In one embodiment, "armored" CAR technology is especially useful in solid tumor indications, in which microenvironment and potent immunosuppressive mechanisms have the potential to make the establishment of a robust anti-tumor response more challenging.

In one embodiment, CAR T-cells are genetically modified to encode molecules involved in the prevention of apoptosis, the remodeling of the tumor microenvironment, induction of homeostatic proliferation, and chemokine receptors that promote directed T-cell homing.

In one embodiment, the CAR binds to an epitope of an antigen via an antibody or an antibody fragment that is directed to the antigen. In another embodiment, the antibody comprises a monoclonal antibody. In another embodiment, the antibody comprises a polyclonal antibody. In another embodiment, the antibody fragment comprises a single-chain variable fragment (scFv).

In another embodiment, the CAR T-cells of the compositions as disclosed herein bind to a tumor associated antigen (TAA). In another embodiment, said tumor associated antigen comprises: Mucin 1, cell surface associated (MUC1) or polymorphic epithelial mucin (PEM), Arginine-rich, mutated in early stage tumors (Armet), Heat Shock Protein 60 (HSP60), calnexin (CANX), methylenetetrahydrofolate dehydrogenase (NADP+ dependent) 2, methenyltetrahydrofolate cyclohydrolase (MTHFD2), fibroblast activation protein (FAP), matrix metallopeptidase (MMP6), B Melanoma Antigen-1 (BAGE-1), aberrant transcript of N-acetyl glucosaminyl transferase V (GnTV), Q5H943, Carcinoembryonic antigen (CEA), Pmel, Kallikrein-4, Mammaglobin-1, MART-1, GPR143-OA1, prostate specific antigen (PSA), TRP1, Tyrosinase, FGP-5, NEU proto-oncogene, Aft, MMP-2, prostate specific membrane antigen (PSMA), Telomerase-associated protein-2, Prostatic acid phosphatase (PAP), Uroplakin II or Proteinase 3.

In another embodiment, the CAR binds to CD19 or CD20 to target B cells in the case where one would like to destroy B cells as in leukemia. In another embodiment, the CAR binds to ROR1, CD22, or GD2. In another embodiment, the CAR binds to NY-ESO-1. In another embodiment, the CAR binds to MAGE family proteins. In another embodiment, the CAR binds to mesothelin. In another embodiment, the CAR binds to c-erbB2. In another embodiment, the CAR binds to mutational antigens that are tumor specific, such as BRAFV600E mutations and BCR-ABL translocations. In another embodiment, the CAR binds to viral antigens which are tumor-specific, such as EBV in HD, HPV in cervical cancer, and polyomavirus in Merkel cancer. In another embodiment, the CAR T-cell binds to Her2/neu. In another embodiment, the CAR T-cell binds to EGFRvIII.

In one embodiment, the chimeric antigen receptor (CAR) T-cell binds to the CD19 antigen, the CD22 antigen, alpha folate receptor, CAIX, CD20, CD23, CD24, CD30, CD33, CD38, CD44v6, CD44v7/8, CD123, CD171, carcinoembryonic antigen (CEA), EGFRvIII, EGP-2, EGP-40, EphA2, Erb-B2, Erb-B 2,3,4, Erb-B3/4, FBP, fetal acetylcholine receptor, $G_{D2}$, $G_{D3}$, HER2, HMW-MAA, IL-11Ralpha. In another embodiment, the CAR binds to IL-13Ralpha1, KDR, kappa-light chain, Lewis Y, L-cell adhesion molecule, MAGE-A1, mesothelin, CMV infected cells, MUC1, MUC16, NKG2D ligands, NY-ESO-1 (amino acids 157-165), oncofetal antigen (h5T4), PSCA, PSMA, ROR1, TAG-72, VEGF-R2 or other VEGF receptors, B7-H6, CA9, αvβ6 integrin, 8H9, NCAM, or fetal acetylcholine receptor.

In one embodiment the CAR binds to an angiogenic factor, thereby targeting tumor vasculature. In one embodiment, the angiogenic factor comprises VEGFR2. In another embodiment, the angiogenic factor comprises endoglin. In another embodiment, an angiogenic factor disclosed herein comprises Angiogenin, Del-1, Fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), VEGFR, Neuropilin 1 (NRP-1), Tie2, PDGFR, endoglin, TGF-3 receptors, monocyte chemotactic protein-1 (MCP-1), Integrins αVβ3, αVβ5 and α5β1, VE-cadherin and CD31, ephrin, plasminogen activators, plasminogen activator inhibitor-1, Nitric oxide synthase (NOS), COX-2, AC133, or Idl/Id3. In one embodiment, an angiogenic protein for use in the compositions and methods disclosed herein comprises an angiopoietin, which in one embodiment, comprises Angiopoietin 1, Angiopoietin 3, Angiopoietin 4 or Angiopoietin 6. In one embodiment, endoglin is also known as CD105; EDG; HHT1; ORW; or ORW1. In one embodiment, endoglin comprises a TGFbeta co-receptor.

In another embodiment, the CAR T-cells bind to an antigen associated with an infectious agent. In another embodiment, the CAR binds to an antibody. In one embodiment, the CAR T-cell comprises an "antibody-coupled T-cell receptor" (ACTR). According to this embodiment, the CAR T-cell comprises a universal CAR T-cell. In another embodiment, the CAR T-cell having an antibody receptor is administered before, after, or at the same time as the antibody is administered and then binds to the antibody, bringing the T-cell in close proximity to the tumor or cancer. In another embodiment, the antibody is directed against a tumor cell antigen. In another embodiment, the antibody is directed against CD20. In another embodiment, the antibody comprises rituximab.

In another embodiment, the antibody is Trastuzumab (Herceptin; Genentech): humanized IgG1, which is directed against ERBB2. In another embodiment, the antibody comprises Bevacizumab (Avastin; Genentech/Roche): humanized IgG, which is directed against VEGF. In another embodiment, the antibody comprises Cetuximab (Erbitux; Bristol-Myers Squibb): chimeric human-murine IgG1, which is directed against EGFR. In another embodiment, the antibody comprises Panitumumab (Vectibix; Amgen): human IgG2, which is directed against EGFR. In another embodiment, the antibody comprises Ipilimumab (Yervoy; Bristol-Myers Squibb): IgG1, which is directed against CTLA4.

Doses and Routes of Administration

In one embodiment, methods of the present invention comprise the step of contacting one or more cells of said subject with a compound or a composition as described herein. In one embodiment, contacting one or more cells of a subject with a compound described herein comprises the step of administering a composition comprising said compound to said subject.

In one embodiment, the composition is administered topically. In one embodiment, the composition is formulated for topical administration.

In another embodiment, the composition is formulated as an ointment, a cream, a lotion, a foam or a gel.

In another embodiment, the composition is administered parenterally. In another embodiment, the composition is formulated for parenteral administration.

In another embodiment, the composition is administered via intravenous, subcutaneous, or intramuscular administration. In another embodiment, the composition is administered orally. In another embodiment, the composition is formulated for intravenous, subcutaneous, or intramuscular administration. In another embodiment, the composition is formulated for oral administration.

In one embodiment, the jasmonic derivatives as described herein are formulated for subcutaneous injection.

In one embodiment, the piperazine derivatives, as described herein are formulated for oral administration.

In one embodiment, methods of the present invention comprise administering to a subject a composition as described herein in a concentration of 5% by weight of the active compound. In another embodiment, methods of the present invention comprise administering to a subject a composition as described herein in a concentration of 10% by weight of the active compound. In another embodiment, methods of the present invention comprise administering to a subject a composition as described herein in a concentration of 20% by weight of the active compound.

In one embodiment, the composition comprises 5% of the compound as described herein. In another embodiment, the composition comprises 10% of the compound as described herein. In another embodiment, the composition comprises 15% of the compound as described herein. In another embodiment, the composition comprises 20% of the compound as described herein. In another embodiment, the composition comprises 30% of the compound as described herein. In another embodiment, the composition comprises 40% of the compound as described herein. In another embodiment, the composition comprises 50% of the compound as described herein. In one embodiment, the compound is the compound represented by the structure of Formula (VII) or Formula (II).

In a further embodiment, the compound as described herein is formulated as 250 mg of a 5%, 10%, 20%, 30%, 40% or 50% cream, gel, ointment or paste. In one embodiment, the compound is the compound represented by the structure of Formula (VII) or Formula (II).

In another embodiment, the compound as described herein is formulated as 200 mg of a 5%, 10%, 20%, 30%, 40% or 50% cream, gel, ointment or paste. In one embodiment, the compound is the compound represented by the structure of Formula (VII) or Formula (II).

In one embodiment, the compound as described herein is administered once per day. In another embodiment, the compound as described herein is administered twice per day. In another embodiment, the compound as described herein is administered three times per day. In another embodiment, the compound as described herein is administered four times per day. In another embodiment, the compound as described herein is administered once every two days, once every three days, twice a week, once a week, once every 2 weeks, once every 3 weeks. In one embodiment, the compound is the compound represented by the structure of Formula (VII). In another embodiment the compound is the compound represented by the structure of Formula (II), which in one embodiment comprises the compounds of Formula (20-24).

In one embodiment, the compound as described herein is administered for 7 days to 28 days. In another embodiment, the compound as described herein is administered for 7 days to 8 weeks. In another embodiment, the compound as described herein is administered for 7 days to 50 days. In another embodiment, the compound as described herein is administered for 7 days to six months. In another embodiment, the compound as described herein is administered for 7 days to one and half years. In another embodiment, the compound as described herein is administered for 14 days to 12 months. In another embodiment, the compound as described herein is administered for 14 days to 3 years. In another embodiment, the compound as described herein is administered for several years. In another embodiment, the compound as described herein is administered for one month to six months. In one embodiment, the compound is the compound represented by the structure of Formula (VII). In another embodiment the compound is the compound represented by the structure of Formula (II), which in one embodiment comprises the compounds of Formula (20-24).

In one embodiment, the compound as described herein is administered for 7 days. In another embodiment, the compound as described herein is administered for 14 days. In another embodiment, the compound as described herein is administered for 21 days. In another embodiment, the compound as described herein is administered for 28 days. In another embodiment, the compound as described herein is administered for 50 days. In another embodiment, the compound as described herein is administered for 56 days. In another embodiment, the compound as described herein is administered for 84 days. In another embodiment, the compound as described herein is administered for 90 days. In another embodiment, the compound as described herein is administered for 120 days. In one embodiment, the compound is the compound represented by the structure of Formula (VII). In another embodiment the compound is the compound represented by the structure of Formula (II), which in one embodiment comprises the compounds of Formula (20-24).

Pharmaceutical Compositions

Although the HK2-detaching compounds of the present invention, including jasmonate derivatives and piperazine derivatives of the present invention can be administered alone, it is contemplated that these compounds will be administered in a pharmaceutical composition containing the jasmonate derivative or piperazine derivative together with a pharmaceutically acceptable carrier or excipient.

In one embodiment, in the pharmaceutical composition the active ingredient is dissolved in any acceptable lipid carrier (e.g., fatty acids, oils to form, for example, a micelle or a liposome). Further, in one embodiment of the present invention, the composition additionally comprises at least one other chemotherapeutic agent.

In one embodiment, at least one of the excipients is a non-aqueous excipient.

In one embodiment, a compound as described herein which in one embodiment is represented by the structure of Formula (VII) or by the structure of Formula (II), may be mixed with stabilizing excipients useful for topical administration in a formulation which is essentially free of compounds bearing a nucleophilic character like water, alcoholic solvents and carboxylic acids. In some embodiments, the topical pharmaceutical composition of the present invention comprises a therapeutically effective amount of a compound as described herein, which in one embodiment is represented by the structure of Formula (VII) or Formula (II), or a pharmaceutically acceptable salt or solvate thereof, and at least one pharmaceutically acceptable excipient selected from the group consisting of a glycol diester with a saturated or unsaturated fatty acid, a triglyceride, an aprotic organic solvent, and any combination thereof, and optionally an oil and/or a wax.

In one embodiment, the pharmaceutically acceptable excipient comprises a compound represented by the structure of Formula (VIII):

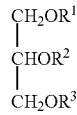

wherein:
$R^1$, $R^2$ and $R^3$ are each selected from the group consisting of H and $R^4$—COO—, wherein at least two of $R^1$, $R^2$ and $R^3$ are $R^4$—COO; and
$R^4$—COO— is the residue of a saturated or unsaturated fatty acid.

In another embodiment, the pharmaceutically acceptable excipient comprises a triglyceride of Formula (VIII) or a combination thereof wherein $R^1$, $R^2$ and $R^3$ are each $R^4$—C(=O)—; and $R^4$—C(=O)O— is the residue of an unsaturated or saturated fatty acid.

In some embodiments, the pharmaceutically acceptable excipient comprises a triglyceride with a medium chain (e.g., $C_8$-$C_{12}$) saturated or unsaturated fatty acid. In one embodiment, the pharmaceutically acceptable excipient is caprylic/capric triglyceride (in one embodiment Labrafac lipophile WL 1349).

In another embodiment, the pharmaceutically acceptable excipient comprises a propylene glycol diester with a saturated or unsaturated fatty acid. In one embodiment, the fatty acid is a medium chain (e.g., $C_8$-$C_{12}$) saturated or unsaturated fatty acid. In one embodiment, the pharmaceutically acceptable excipient is propylene glycol dicaprylate (in one embodiment, Labrafac PG).

In one embodiment, the organic solvent is dimethylsulfoxide (DMSO).

Compositions of the present invention may further comprise optional components such as lipid carriers such as oils or waxes so as to provide a semi-solid consistency as desired. Additional inactive excipients such as preservatives, anti-oxidants, perfumes and the like may also be added.

Oils that can be used as optional components in the compositions of the present invention include, but are not limited to, petrolatum (petroleum jelly), vegetable oil, fruit oil, plant oil, animal oil, mineral oil, coconut oil, olive oil, lanolin, peanut oil, hydrogenated and sulphated oils such as cottonseed oil, soybean oils, almond oil, sesame oil, and the like. In another embodiment, the oil comprises corn oil, peanut oil, coconut oil, grape seed oil, sunflower oil, lemon oil, orange oil, peppermint oil, palm kernel oil, castor oil, hydrogenated cottonseed oil, hydrogenated soy oil, hydrogenated soybean oil, hydrogenated vegetable oil, partially hydrogenated soybean oil, partially hydrogenated palm oil, hydrogenated castor oil, light mineral oil, mineral oil, or a combination thereof.

Waxes that can be used as optional components in the compositions of the present invention include, but are not limited to, paraffin wax, beeswax, carnauba wax, cetyl ester wax, microcrystalline wax, spermaceti wax, and the like.

In some embodiments, the composition of the invention comprises the compound as described herein, propylene glycol dicaprylate (Labrafac PG), caprylic/capric triglyceride (Labrafac lipophile WL 1349), dimethylsulfoxide (DMSO), petrolatum and paraffin wax.

In some embodiments, the composition of the invention comprises a compound as described herein in an amount of from about 5% w/w to about 30% w/w. In some embodiments, the composition of the invention comprises a compound as described herein in an amount of about 5% w/w. In some embodiments, the composition of the invention comprises a compound as described herein in an amount of about 10% w/w. In some embodiments, the composition of the invention comprises a compound as described herein in an amount of about 15% w/w. In some embodiments, the composition of the invention comprises a compound as described herein in an amount of about 20% w/w. In one embodiment, the compound is a compound represented by the structure of Formula (VII) as described herein. In another embodiment, the compound is a compound represented by the structure of Formula (II) as described herein.

In some embodiments, the composition of the invention comprises a compound as described herein in an amount of from about 5% to about 30% w/w; propylene glycol dicaprylate in an amount of from about 1% to about 10% w/w; caprylic/capric triglyceride in an amount of from about 30% to about 50% w/w; dimethyl sulfoxide in an amount of from about 0% to about 10% w/w; petrolatum in an amount of from about 20% to about 50% w/w; and paraffin wax in an amount of from about 0 to about 10% w/w.

In some embodiments, the composition of the invention comprises a compound as described herein in an amount of about 5% w/w; propylene glycol dicaprylate in an amount of about 10% w/w; caprylic/capric triglyceride in an amount of about 50% w/w; dimethyl sulfoxide in an amount of about 1% w/w; petrolatum in an amount of about 30% w/w; and paraffin wax in an amount of about 4% w/w.

In other embodiments, the composition of the invention comprises a compound as described herein in an amount of about 10% w/w; propylene glycol dicaprylate in an amount of about 7.5% w/w; caprylic/capric triglyceride in an amount of about 47.5% w/w; dimethyl sulfoxide in an amount of about 1% w/w; petrolatum in an amount of about 30% w/w; and paraffin wax in an amount of about 4% w/w.

In other embodiments, the composition of the invention comprises: a compound as described herein in an amount of about 15% w/w; propylene glycol dicaprylate in an amount of about 5% w/w; caprylic/capric triglyceride in an amount of about 45% w/w; dimethyl sulfoxide in an amount of about 1% w/w; petrolatum in an amount of about 30% w/w; and paraffin wax in an amount of about 4% w/w.

In certain embodiments, the composition of the invention comprises a compound as described herein in an amount of about 20% w/w; propylene glycol dicaprylate in an amount of about 2.5% w/w; caprylic/capric triglyceride in an amount of about 42.5% w/w; dimethyl sulfoxide in an amount of about 1% w/w; petrolatum in an amount of about 30% w/w; and paraffin wax in an amount of about 4% w/w.

In some embodiments, the composition described above is essentially free of water, alcoholic solvents and carboxylic acids.

The pharmaceutically acceptable excipients according to the principles of the present invention may be a triglyceride, a glycol diester or a combination thereof. In some embodiments, the triglyceride and/or the glycol diester comprise saturated or unsaturated fatty acids. The term "saturated fatty acid" encompasses a carboxylic acid with an elongated aliphatic saturated chain. The term "unsaturated fatty acid" encompasses a carboxylic acid with an elongated aliphatic chain which have one or more double bonds between the carbon atoms. The length of the carbon chain may vary, but may generally be between 4 and 30 carbon atoms ($C_4$-$C_{30}$). In some embodiments, the triglyceride and/or glycol diester comprises medium chain (e.g., $C_8$-$C_{12}$) saturated or unsaturated fatty acids.

The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, or via a suppository. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound for use in the present invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. In one embodiment, water is the carrier when the pharmaceutical composition is administered intravenously. Saline solutions and aqueous dextrose and glycerol solutions can also be employed as liquid carriers, particularly for injectable solutions.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, in one embodiment, orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols. In one embodiment, the composition for topical administration comprises 5% by weight of the active compound. In another embodiment, the composition for topical administration comprises 10% by weight of the active compound. In another embodiment, the composition for topical administration comprises 20% by weight of the active compound.

Alternative formulations include nasal sprays, liposomal formulations, slow-release formulations, controlled-release formulations and the like, as are known in the art.

In one embodiment, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. In one embodiment, administration is localized. In another embodiment, administration is systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In another embodiment, a compound of the invention is administered in combination with a biodegradable, biocompatible polymeric implant, which releases the compound over a controlled period of time at a selected site. Examples of polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions formulated for parenteral administration may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Alternatively, the jasmonate derivatives and piperazine derivatives of the present invention can be used in hemodialysis such as leukophoresis and other related methods, e.g., blood is drawn from the patient by a variety of methods such dialysis through a column/hollow fiber membrane, cartridge etc., is treated with the jasmonate derivatives and piperazine derivatives ex-vivo, and returned to the patient following treatment. Such treatment methods are well known and described in the art. See, e.g., Kolho et al. (J. Med. Virol. 1993, 40(4): 318-21); Ting et al. (Transplantation, 1978, 25(1): 31-3); the contents of which are hereby incorporated by reference in their entirety.

As used herein, the term "administering" refers to bringing in contact with a compound of the present invention. In one embodiment, the compositions are applied locally. In another embodiment, the compositions are applied systemically. Administration can be accomplished to cells or tissue cultures, or to living organisms, for example humans.

A "therapeutic" treatment is a treatment administered to a subject who exhibits signs of pathology for the purpose of diminishing or eliminating those signs.

In one embodiment, compounds and compositions of the present inventions are provided to a subject in a therapeutically effective amount. In one embodiment, a "therapeutically effective amount" of a compound of the invention is that amount of compound which is sufficient to provide a beneficial effect to the subject to which the compound is administered.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

According to any of the methods of the present invention and in one embodiment, the subject is human. In another embodiment, the subject is mammalian. In another embodiment, the subject is a primate, which in one embodiment, is a non-human primate. In another embodiment, the subject is murine, which in one embodiment is a mouse, and, in another embodiment is a rat. In another embodiment, the subject is canine, feline, bovine, equine, caprine, ovine, porcine, simian, ursine, vulpine, or lupine. In one embodiment, the subject is a chicken or fish.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. In one embodiment, the dosage will be within the range of 0.01-1000 mg/kg of body weight, in another embodiment, 0.1 mg/kg to 100 mg/kg, in another embodiment, 1 mg/kg to 10 mg/kg, and, in another embodiment, 100-400 mg/kg. Effective doses may be extrapolated from dose-response curves derived from in vitro or animal model test bioassays or systems.

In one embodiment, the terms "treating or inhibiting a malignant cell proliferative disease or disorder", "treating or inhibiting a non-solid cancer", "treating or inhibiting a tumor" are used herein in the description and in the claims, they are intended to encompass tumor formation, primary tumors, tumor progression or tumor metastasis.

In one embodiment, the methods of the present invention comprise inhibiting proliferation of cancer or tumor cells. In one embodiment, the term "inhibiting proliferation" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in one embodiment, the tumor diminishes or is reduced in size. The term also includes reduction in the number of metastasis, reduction in the number of new metastasis formed, slowing of the progression of cancer from one stage to the other and a decrease in the angiogenesis induced by the cancer. In one embodiment, the tumor is totally eliminated. Additionally included in this term is lengthening of the survival period of the subject undergoing treatment, lengthening the time of diseases progression, tumor regression, and the like. This term also encompasses prevention for prophylactic situations or for those individuals who are susceptible to contracting a tumor. The administration of the compounds of the present invention will reduce the likelihood of the individual contracting the disease. In one embodiment, the individual to whom the compound is administered does not contract the disease.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

In one embodiment, a "therapeutic" treatment comprises a treatment administered to a subject who exhibits signs of pathology for the purpose of diminishing or eliminating those signs. A "therapeutically effective amount" of a compound of the invention comprises that amount of compound which is sufficient to provide a beneficial effect to the subject to which the compound is administered.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

According to any of the methods of the present invention and in one embodiment, the subject is a mammal. In one embodiment, the subject is a primate such as a monkey, chimpanzee or gorilla. In one embodiment, the subject is human. In another embodiment, the subject is murine, which in one embodiment is a mouse, and, in another embodiment is a rat. In another embodiment, the subject is canine, feline, bovine, or porcine.

In one embodiment, the subject is an adult. In another embodiment, the subject is a child. In another embodiment, the subject is elderly. In one embodiment, the subject is male. In another embodiment, the subject is female.

In one embodiment, compounds and compositions of the present inventions are provided to a subject in a therapeutically effective amount. In one embodiment, the compositions are applied locally. In another embodiment, the compositions are applied systemically.

Kits

In another embodiment, the present invention provides a kit for treating, inhibiting or suppressing a hexokinase-2 (HK2)-expressing cancer or tumor in a subject comprising a therapeutically effective amount of a compound that promotes the detachment of HK2 from the mitochondria; and instructions for use for treating, inhibiting or suppressing an HK2-expressing cancer or tumor, as described herein. In one embodiment, the compound is a compound represented by the structure of Formula (VII) as described herein. In another embodiment, the compound is a compound represented by the structure of Formula (II) as described herein. In one embodiment, the HK2-expressing cancer or tumor comprises CTCL.

In another embodiment, the present invention provides a kit for inhibiting the proliferation of hexokinase-2 (HK2)-expressing cells comprising administering a therapeutically effective amount of a compound that promotes the detachment of HK2 from the mitochondria, and instructions for use for inhibiting the proliferation of HK2-expressing cells, as described herein.

In one embodiment, the HK2-expressing cells comprise CTCL cells. In one embodiment, the compound is a compound represented by the structure of Formula (VII) as described herein. In another embodiment, the compound is a compound represented by the structure of Formula (II) as described herein.

In another embodiment, the present invention provides a kit for potentiating the immune response to a hexokinase-2 (HK2)-expressing cancer or tumor in a subject comprising administering a therapeutically effective amount of a compound that promotes the detachment of HK2 from the mitochondria, and instructions for use for potentiating the immune response to a HK2-expressing cancer or tumor in a subject, as described herein. In one embodiment, the HK2-expressing cancer or tumor comprises CTCL. In one embodiment, the compound is a compound represented by the structure of Formula (VII) as described herein. In another embodiment, the compound is a compound represented by the structure of Formula (II) as described herein.

In another embodiment, the present invention provides a kit for treating, suppressing, or inhibiting to a hexokinase-2 (HK2)-expressing pre-cancerous condition or a benign hyperproliferative disorder in a subject comprising administering a therapeutically effective amount of a compound that promotes the detachment of HK2 from the mitochondria for treating, suppressing, or inhibiting a HK2-expressing pre-cancerous condition or a benign hyperproliferative disorder in a subject, as described herein. In one embodiment, the compound is a compound represented by the structure of Formula (VII) as described herein. In another embodiment, the compound is a compound represented by the structure of Formula (II) as described herein.

In one embodiment, the kit comprises additional containers comprising additional cancer therapeutics as described herein.

Any patent, patent application publication, or scientific publication, cited herein, is incorporated by reference herein in its entirety.

EXAMPLES

Materials and Methods

A431 (human skin SCC), HT-297.T (human AK), and HaCaT transformed normal keratinocyte cell lines were from ATCC (Manassas, Va.) and were maintained in DMEM supplemented with 10% FCS, 4 mM L-Gln, 1 mM sodium pyruvate, 100 U/mL penicillin, 1 µg/mL streptomycin. Human HK1 and HK2 plasmids were purchased from Addgene (Cambridge, Mass.) and were purified from *E. Coli*. VDAC1 was purified from sheep liver mitochondria as described (Arbel et al. 2012, incorporated herein by reference). Human skin tissue microarray (SK208 and SK 805) were purchased from US Biomax Inc. (Rockville, Md.).

MST Assay

Studies were conducted on Nanotemper Monolith NT. 115 (Munich, Germany). HK1 and HK2 were labeled using Monolith™ NT. 115 Protein Labeling Kit BLUE-NHS. As a preliminary study to form the VDAC1-HK complexes, various concentrations of VDAC1 were added to 67 nM HK1 or 71 nM HK2. The preferred VDAC1 concentration was determined to be 1.5 µM. For dissociation studies, HKs were pre-incubated with VDAC1 for 10 minutes and various concentrations of Formula C were added for an additional 10 minutes. MST default parameters were used and analysis was with Nanotemper analysis software. All studies were done at room temperature in assay buffer of 20 mM Tris, 10 mM glucose, 10 mM $MgCl_2$, and 1% DMSO pH 7.5.

Western Blot (WB)

A431 cells were treated for 2 hours at 37° C. with various concentrations of Formula C in medium without FCS and 2 mM L-Gln. Mitochondria were isolated using Mitochondria Isolation Kit (Thermo Fisher Scientific, Rockford, Ill.) followed by a WB. Semi-quantification of the WB was done with Imagequant TL software v8.1 (GE healthcare Life Sciences, Little Chalfont, United Kingdom). TIM22 was used as a loading control for mitochondria. Cyclophilin A (PPIA) was used as a cytosolic marker.

Antibodies used: anti-rabbit HK1 (C-2024S) and HK2 (C-2876S) from CST (Danvers, Mass.), anti-rabbit PPIA (ab41684, Abcam), anti-rabbit TIM22 (14927-1-AP, Proteintech Group Inc., Rosemont, Ill.), anti-rabbit Cytochrome C (PA1118, Boster Biological Technology, Pleasanton, Calif.). Detection was performed using secondary antibodies: peroxidase-conjugated Affinipure goat anti-rabbit IgG (H+L) or goat anti-mouse IgG (H+L) (111-035-003 and 115-035-003, Jackson ImmunoResearch, West Grove, Pa.), and development was using the ECL kit WesternBright™ ECL (K-12045-D10, Advansta, Menlo Park, Calif., USA).

ATP Determination

Cellular ATP levels were determined using CellTiter-Glo® Luminescent Cell Viability Assay kit (Promega, Madison, Wis.) following 2 hours of treatment at 37° C.

Apoptosis

Apoptosis induction was determined by semi-quantification of cytochrome C levels in the mitochondrial fraction analyzed by WB, following 2 hours of treatment with Formula C in A431 cells. Cleaved caspase-3 levels were analyzed following 6 hours of Formula C treatment in A431 cells, using PathScan® Cleaved Caspase-3 Sandwich ELISA kit (CST, Danvers, Mass.).

Cell Viability Assays

For XTT assays, cells were plated in 96-well plates (5,000 cells per well) for 24 hours. Cells were then incubated with different concentrations of Formula C in triplicates for 72 hr in DMEM supplemented with 0.5% FCS and 5 mM Glucose. Cell viability was evaluated using 2,3-bis-(2-methoxy-4-nitro-5-sulfophenyl)-2H-tetrazolium-5-carboxanilide (XTT)-based colorimetric assay kit (Biological Industries Ltd., Kibbutz Beit-Haemek, Israel). The optical density was measured by an Infinite 200 ELISA reader at 450 nm and reference was measured at 630 nm (Tecan, Mannedorf, Switzerland).

CFA was performed by Charles River Laboratories (Freiburg, Germany) in 96-well plate format according to a modified two-layer soft agar assay. The origin of the tumor xenografts has been described (Fiebig et al. 1989, incorporated herein by reference). The list of tumors used in this study is detailed in Table 1.

Topical Formulation

The formulation ingredients for vehicle, 2.5%, and 5% Formula C ointment consisted of: 32% Gelucire44/14® (Gattefossé, Saint-Priest, France), and 68% combined Labrasol® (Gattefossé, Saint-Priest, France) with corresponding amount of Formula C (w/w). New ointments were prepared every 2 weeks. The 40% topical solution was prepared just prior to use by mixing (w/w) 60% propylene glycol (Sigma, St. Louis, Mo., USA) with 40% Formula C.

IHC, Histology and Semi-Quantitative Analysis of IHC Slides

Histopathological analysis and IHC was performed according to standard protocols. Primary antibodies used: rabbit anti-HK1 and rabbit anti-HK2 (C35C4 and C64G5, CST, Danvers, Mass.), rabbit anti cleaved caspase 3 (PP229, Biocare Medical, Concord, Calif.), Secondary antibody was goat anti-Rabbit IgG(H+L) (474-1506, KPL, Gaithersburg, Md.). Rabbit anti-CD3 (SP7), rabbit anti-F4/80 (SB-M3072, SB-M4152, Nordic Biosite, Taby, Sweden), mouse anti-Langerin/CD207 (DDX0361, Dendritics, Lyon, France). For these three primary antibodies, a polymer system was used as a secondary antibody (KDB-10046 and KDB-10007, Nordic Biosite, Taby, Sweden). Semi-quantitative analysis was done in a blinded manner by a single experienced pathologist scoring ×40 high power fields, 7 different fields per slide.

HK Catalytic Activity Assay

Hexokinase catalytic activity was determined by the coupled enzymatic assay in which hexokinase catalyzes the conversion of glucose to G6P, which is then oxidized by glucose-6-phosphate dehydrogenase (G6PDH) in the presence of NADP to form 6-Phospho-D-Gluconate and NADPH. NADPH production results in a colorimetric signal at 340 nm, which is proportional to the hexokinase catalytic activity. The readings were recorded in an ELISA plate reader Infinite 200 ELISA reader (Tecan, Mannedorf, Switzerland).

Statistical Analysis

Statistical analysis was carried out using Graphpad Prism version 5.03 (Graphpad Software, San Diego, Calif.).

Example 1

Formula C Selectively Modulates VDAC1/HK2 Interactions In Vitro, Leading to Apoptosis The activity of Formula C in a cell-free assay was evaluated using Microscale Thermophoresis (MST) analysis, which is based on altered movement of a protein in a temperature gradient when bound to other molecules. The HKs were first allowed to bind with VDAC1 to form the VDAC1/HK complexes prior to the addition of Formula C. An addition of Formula C selectively dissociated the VDAC1/HK2 complex in a dose-dependent manner with an IC50 of 0.092 µM. Formula C had no effect on the VDAC1/HK1 complex (FIG. 1).

Figure 2A:
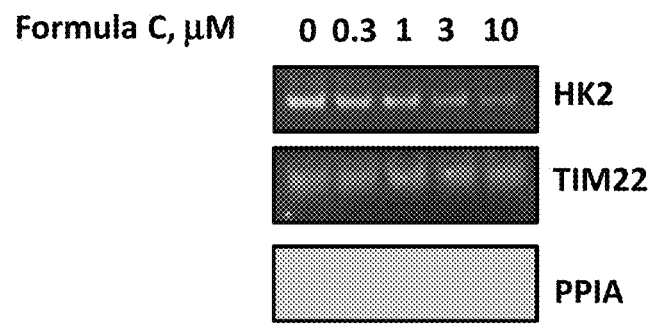
FIG. 2A. In vitro activity of Formula C. Cellular detachment of HK2 in A431 cells following 2 hr treatment, Western Blot of the mitochondrial fraction. PPIA, marker for cytosol. TIM22, mitochondria loading control.
Figure 2B:
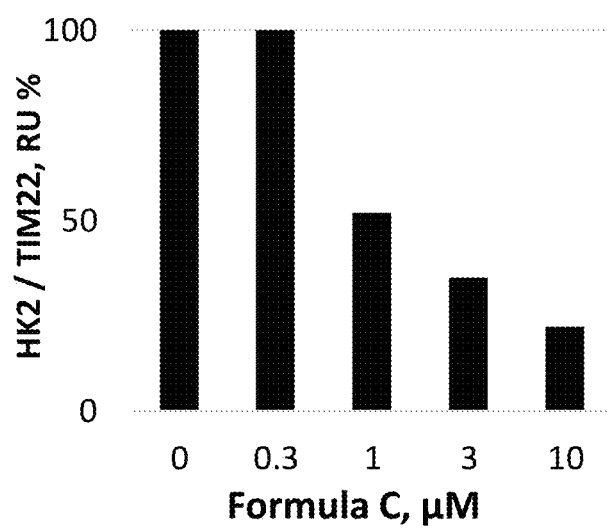
FIG. 2B. In vitro activity of Formula C. Semi-quantification of Western Blot in FIG. 2A.
Figure 2C:
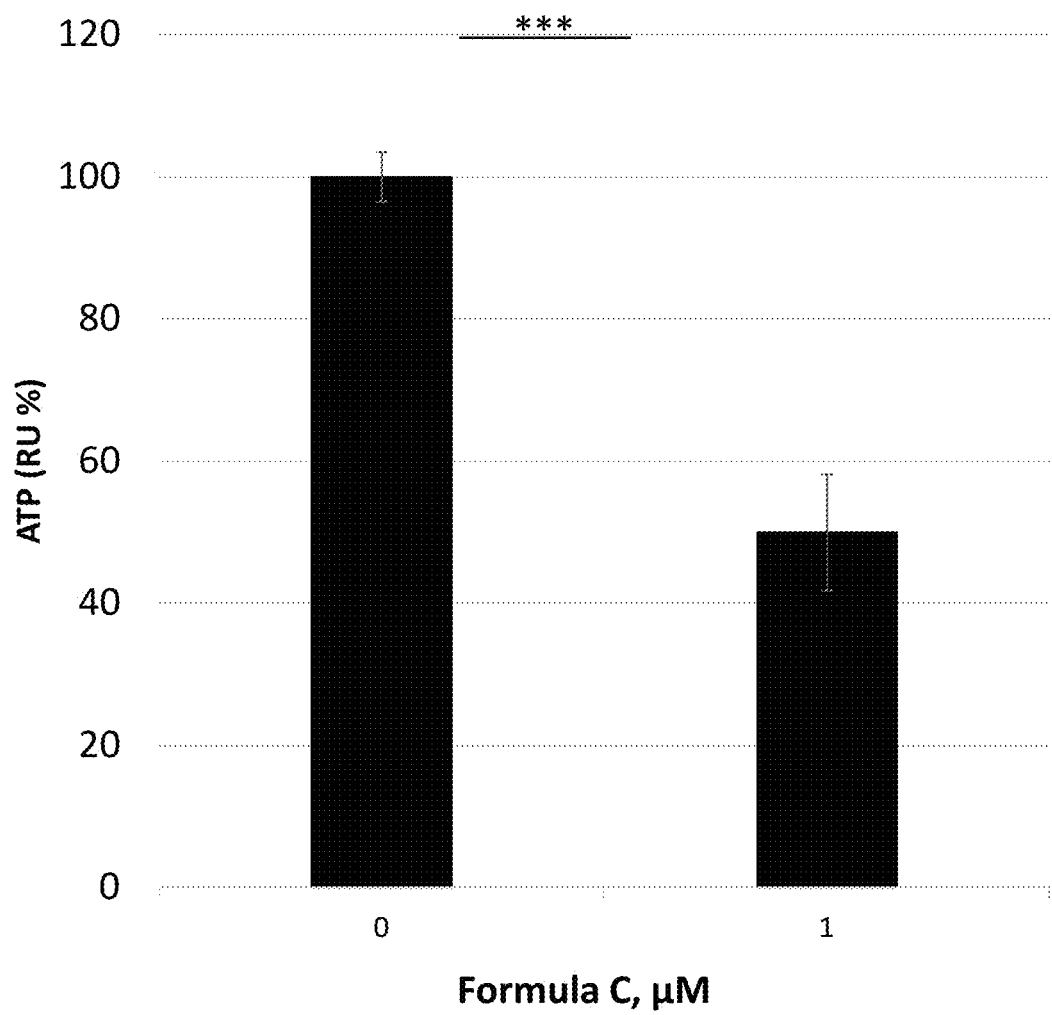
FIG. 2C. In vitro activity of Formula C. ATP levels following 2 hr treatment with Formula C in A431 cells.

The cellular effect of Formula C was demonstrated in human skin SCC A431 cells (which express both HK1 and HK2). Cells were incubated with increasing concentrations of Formula C, followed by mitochondrial isolation and Western Blot (WB) analysis (FIG. 2A). Semi-quantification of the WB revealed that within 2 hours, there was a dose-dependent reduction of mitochondrial-bound HK2 levels, with an IC50 of approximately 0.8 µM (FIG. 2B); in contrast, HK1 association with the mitochondria was not affected by Formula C in a similar experimental setup (data not shown). Formula C reduced cellular ATP levels by as much as 50% following 2-hour incubation in A431 cells, demonstrating the energetic outcome of HK2 dissociation from the mitochondria (FIG. 2C).

Figure 3B:
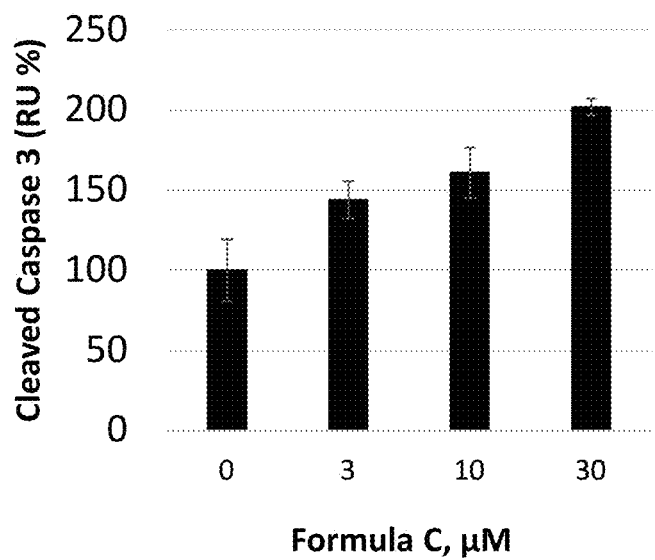
FIG. 3B. Apoptosis induction by Formula C in vitro. Cleaved caspase-3 following 6 hr treatment (ELISA).

Apoptosis induction by treatment with Formula C was demonstrated in two ways: a) reduction of cytochrome C levels in the mitochondrial fraction within 2 hours of treatment, as evaluated by WB and semi-quantification (FIG. 3A) and increase in cellular levels of cleaved caspase-3 within 6 hours of treatment (FIG. 3B). These two early events are in line with a caspase-dependent apoptotic mechanism (Kvansakul and Hinds 2015).

Figure 3C:
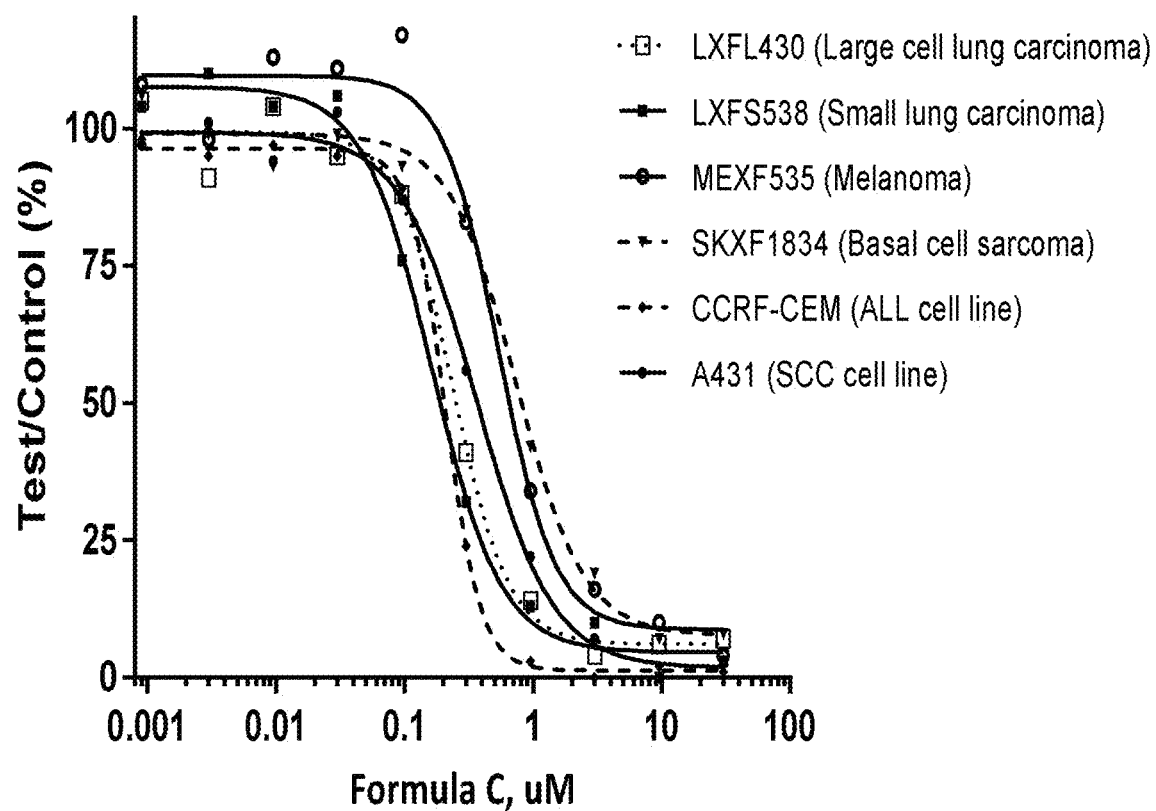
FIG. 3C. In vitro activity of Formula C. Colony Forming Assay (CFA) of Formula C on patient-derived tumors and cell lines.
Figure 4A:
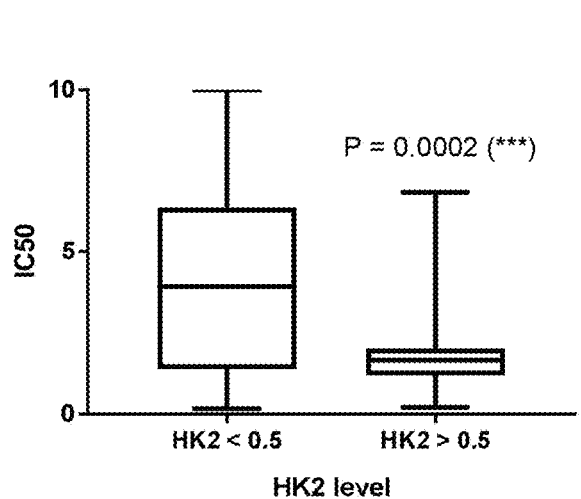
FIG. 4A. HK2 levels in 57 cell lines and patient-derived models analyzed by Western Blot and correlated to their IC50 values. Statistical two-tailed t-test p-values were calculated using the Prism version 7.02 for Windows (GraphPad Software Inc., La Jolla, Calif. 92037 USA).

The effect of Formula C on cellular viability was demonstrated in XTT assay in A431 cSCC cells (FIG. 3C) and the human AK line, HT-297.T, resulting in IC50 values of 0.014 and 0.228 µM, respectively. Furthermore, Formula C had a low affinity in this assay for the normal transformed human skin keratinocyte line, HaCaT (IC50=3.37 µM), supporting the notion that it is selective. Formula C was evaluated in colony forming assay (CFA) in a panel of 57 patient-derived tumors and cancer cell lines, where it exhibited a strong anti-proliferation effect (IC50<2 uM) in 70% of tested cancer types. Dose-response curves for a subset of these tumor models are shown in FIG. 3C. HK2 protein levels in each of these 57 tumor models were determined by WB, semi-quantified, and normalized to a [0-1] range. FIG. 4A shows a statistically significant correlation (p=0.0002) between cellular HK2 levels and Formula C IC50 values. The complete list of tumor models tested in CFA and XTT is shown in Table 1.

TABLE 1

IC50 values for Formula C in various cell lines and tumor models

| | Tumor type | Tumor Designation | Model Number | Type/Assay | IC50 (uM) |
|---|---|---|---|---|---|
| 1 | Normal immortal keratonocytes | HaCaT | | Cell line/XTT* | 3.37 |
| 2 | Skin SCC | A431 | | Cell line/XTT | 0.014 |
| 3 | Actinic keratosis | HT-297.T | | Cell line/XTT | 0.228 |
| 4 | Colon | CXF | 243 | PDX**/CFA*** | 1.759 |
| 5 | Colon | CXF | 280 | PDX/CFA | 5.442 |
| 6 | Colon | CXF | HCT 116 | PDX/CFA | 4.334 |
| 7 | Stomach | GXF | 214 | PDX/CFA | 1.943 |
| 8 | Stomach | GXF | 97 | PDX/CFA | 6.454 |
| 9 | Head & Neck | HNXF | 536 | PDX/CFA | 1.435 |
| 10 | Head & Neck | HNXF | 908 | PDX/CFA | 3.878 |
| 11 | Head & Neck | HNXF | 2205 | PDX/CFA | 3.959 |
| 12 | Leukemia (ALL) | LEXFAL | CCRF-CEM | Cell line/CFA | 0.206 |
| 13 | Leukemia (AML) | LEXFAM | OCI-AML2 | Cell line/CFA | 0.985 |
| 14 | Leukemia (AML) | LEXFAM | KG-1 | Cell line/CFA | 1.16 |
| 15 | Leukemia (AML) | LEXFAM | MV4-11 | Cell line/CFA | 1.203 |
| 16 | Leukemia (AML) | LEXFAM | NOMO-1 | Cell line/CFA | 1.424 |
| 17 | Leukemia (AML) | LEXFAM | HL-60 | Cell line/CFA | 1.545 |
| 18 | Leukemia (AML) | LEXFAM | PL-21 | Cell line/CFA | 1.737 |
| 19 | Leukemia (AML) | LEXFAM | KG-1a | Cell line/CFA | 1.918 |
| 20 | Leukemia (AML) | LEXFAM | THP-1 | Cell line/CFA | 2.182 |
| 21 | Leukemia (ALL) | LEXFAL | MOLT-4 | Cell line/CFA | 2.277 |
| 22 | Leukemia (B-CLL) | LEXFCL | MEC-1 | Cell line/CFA | 1.162 |
| 23 | Leukemia (B-CLL) | LEXFCM | JURL-MK1 | Cell line/CFA | 1.666 |
| 24 | Leukemia (B-CLL) | LEXFCM | K-562 | Cell line/CFA | 2.338 |
| 25 | Leukemia (B-CLL) | LEXFCM | MEG-01 | Cell line/CFA | 2.758 |
| 26 | Leukemia (B-CLL) | LEXFCM | EM-2 | Cell line/CFA | 2.782 |
| 27 | Liver (HCC) | LIXFH | Hep G2 | Cell line/CFA | 5.197 |
| 28 | Lung (NSCLC, large) | LXFL | 430 | PDX/CFA | 0.237 |
| 29 | Lung (NSCLC, adeno) | LXFA | 1012 | PDX/CFA | 1.362 |
| 30 | Lung (NSCLC, adeno) | LXFA | 629 | PDX/CFA | 1.383 |
| 31 | Lung (NSCLC, adeno) | LXFA | 1041 | PDX/CFA | 1.5 |
| 32 | Lung (NSCLC, large) | LXFL | 1072 | PDX/CFA | 1.572 |
| 33 | Lung (NSCLC, adeno) | LXFA | 749 | PDX/CFA | 1.702 |
| 34 | Lung (NSCLC, epidermoid) | LXFE | 772 | PDX/CFA | 3.78 |
| 35 | Lung (NSCLC, epidermoid) | LXFE | 937 | PDX/CFA | 5.571 |
| 36 | Lung (NSCLC, epidermoid) | LXFE | 690 | PDX/CFA | 6.819 |
| 37 | Lung (SCLC) | LXFS | 538 | PDX/CFA | 0.163 |
| 38 | Lung (SCLC) | LXFS | NCI-H727 | Cell line/CFA | 0.835 |
| 39 | Lung (SCLC) | LXFS | NCI-H82 | Cell line/CFA | 1.766 |
| 40 | Lung (SCLC) | LXFS | 573 | PDX/CFA | 1.939 |
| 41 | Lung (SCLC) | LXFS | 2156 | PDX/CFA | 3.56 |
| 42 | Lymphoma (Non-Hodgkin) | LYXFNH | HUT-78 | Cell line/CFA | 0.965 |
| 43 | Lymphoma (Non-Hodgkin) | LYXF | MY-LA | Cell line/CFA | 1 |
| 44 | Lymphoma (Non-Hodgkin) | LYXFNH | HH | Cell line/CFA | 1.222 |
| 45 | Lymphoma (Non-Hodgkin) | LYXFNH | U-937 | Cell line/CFA | 1.275 |
| 46 | Lymphoma (Non-Hodgkin) | LYXFNH | RAJI | Cell line/CFA | 1.379 |
| 47 | Breast | MAXF | 1322 | PDX/CFA | 1.552 |
| 48 | Breast | MAXF | 857 | PDX/CFA | 1.556 |
| 49 | Breast | MAXF | MDA-MB-231 | Cell line/CFA | 1.7 |
| 50 | Breast | MAXF | 401 | PDX/CFA | 4.22 |
| 51 | Breast | MAXF | 574 | PDX/CFA | 5.41 |
| 52 | Melanoma | MEXF | 535 | PDX/CFA | 0.538 |
| 53 | Prostate | PRXF | MRI-H-1579 | Cell line/CFA | 1.661 |
| 54 | Prostate | | PC-3 | Cell line/XTT | 1.2 |
| 55 | Kidney | RXF | 423 | PDX/CFA | 1.698 |
| 56 | Pancreas | PAXF | 736 | PDX/CFA | 1.741 |
| 57 | Pancreas | PAXF | Mia-Pa-Ca-2 | Cell line/CFA | 1.966 |
| 58 | Kidney | RXF | 1220 | PDX/CFA | 6.326 |
| 59 | Skin SCC | VXF | A-431 | Cell line/CFA | 0.364 |
| 60 | Skin SCC | SKXF | 1834 | PDX/CFA | 0.742 |

TABLE 1-continued

IC50 values for Formula C in various cell lines and tumor models

| | Tumor type | Tumor Designation | Model Number | Type/Assay | IC50 (uM) |
|---|---|---|---|---|---|
| 61 | Skin SCC | SXFS | 627 | PDX/CFA | 1.556 |
| 62 | Cutanous T cell lymphoma | | MyLa | Cell line/CFA | <<1 |
| 63 | Cutanous T cell lymphoma | | HH | Cell line/XTT | 0.604 |
| 64 | Cutanous T cell lymphoma | | Hut-78 | Cell line/XTT | 1.06 |
| 65 | Cutanous T cell lymphoma | | MJ | Cell line/XTT | 1.47 |

Figure 4B:
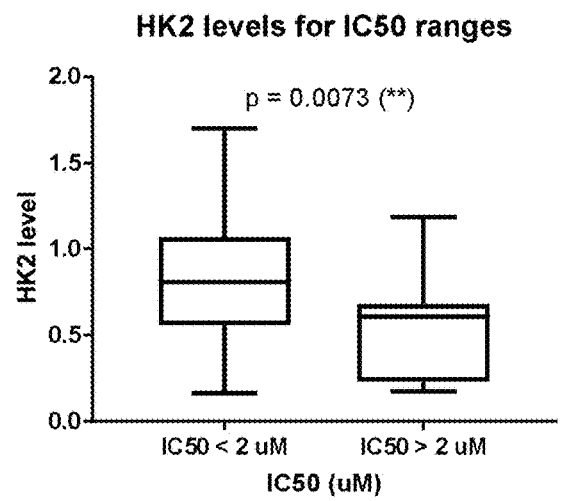
FIG. 4B graphically illustrates the correlation between Western Blot-determined HK2 levels in 57 cell lines and patient-derived tumors and the IC50 values of Formula C on CFA (p=0.0073) in the cells/tissue. Statistical two-tailed t-test p-values were calculated using the Prism version 7.02 for Windows (GraphPad Software Inc., La Jolla, Calif. 92037 USA).

*XTT assay: 6 vehicle controls (0.5% DMSO in culture media), 9 concentrations (half log intervals) of drug-treated groups in triplicates
**PDX, patient-derived tumors
***CFA: 6 vehicle controls (0.3% DMSO in culture media), 10 concentrations (half log intervals) of drug-treated groups in duplicates The data demonstrated that tissues and cell lines in which Formula C was a potent inhibitor of colony formation (i.e. low IC50 values in CFA) were more likely to have high HK2 levels than tissues and cell lines in which Formula C was not a potent inhibitory of colony formation (FIG. 4B; p=0.0073). Similarly, Formula C was a more potent inhibitor of colony formation in tissues and cell lines having high HK2 levels (greater than 0.5; FIG. 4A; p=0.0002).

Figure 4C:
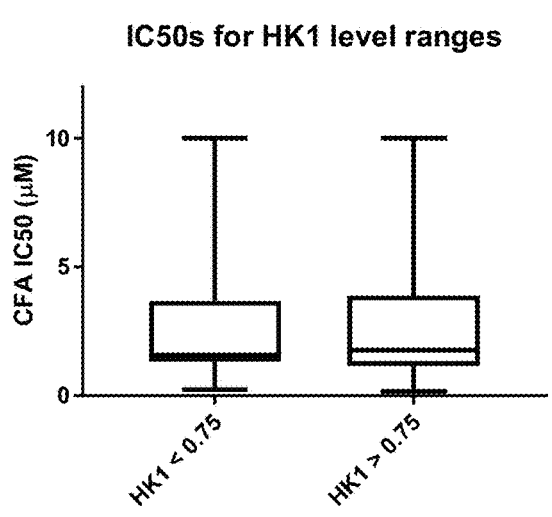
FIG. 4C graphically illustrates the correlation between CFA IC50 values of Formula C and Western Blot-determined hexokinase-1 (HK1) levels in 57 cell lines and patient-derived tumors (p=0.6120). Statistical two-tailed t-test p-values were calculated using the Prism version 7.02 for Windows (GraphPad Software Inc., La Jolla, Calif. 92037 USA).
Figure 4D:
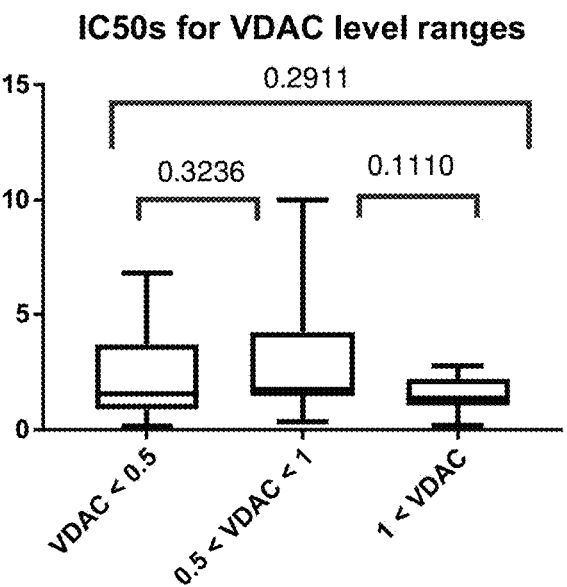
FIG. 4D graphically illustrates the correlation between CFA IC50 values of Formula C and Western Blot-determined mitochondrial voltage dependent anion channels (VDAC) levels in 57 cell lines and patient-derived tumors. Statistical two-tailed t-test p-values were calculated using the Prism version 7.02 for Windows (GraphPad Software Inc., La Jolla, Calif. 92037 USA).

In contrast, no correlation was observed between Formula C's in vitro cancer inhibitory activity in a tissue or cell line and the protein levels of HK1 (FIG. 4C) or VDAC (FIG. 4D) in the tissue or cell line.

Figure 5A:
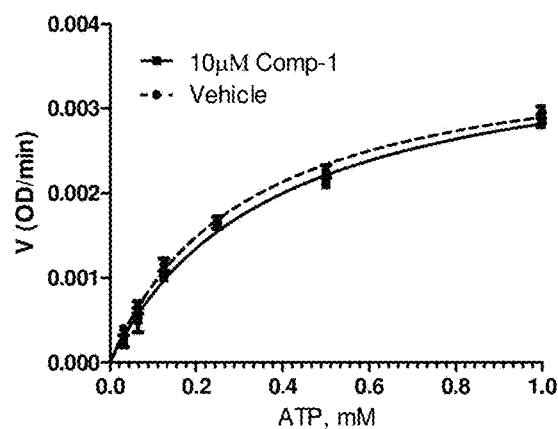
FIGS. 5A-5D. Formula C does not affect the catalytic activities of the HK enzymes. HK1 (FIG. 5A, FIG. 5B) or HK2 (FIG. 5C, FIG. 5D) enzymatic activities were measured as a function of either substrate, ATP (FIG. 5A, FIG. 5C) or glucose (FIG. 5B, FIG. 5D), in the absence or presence of 10 µM Formula C.
Figure 5B:
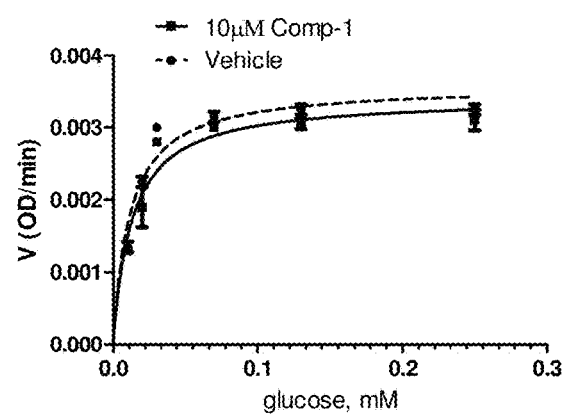
Figure 5C:
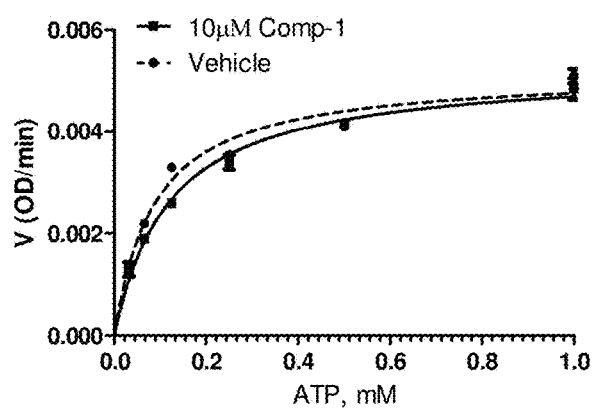
Figure 5D:
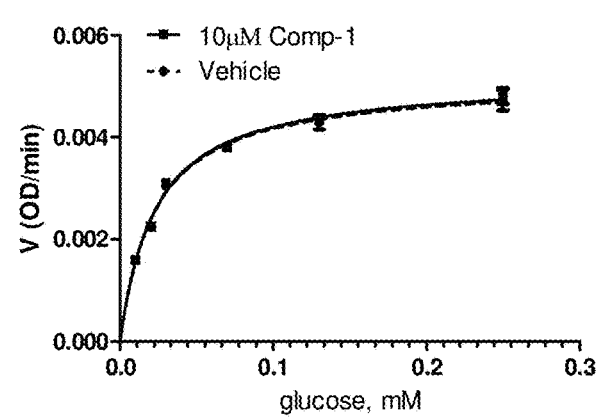

To note, Formula C did not affect the catalytic activity of either HK1 (FIGS. 5A-5B) nor HK2 (FIGS. 5C-5D), nor did it affect the kinetic parameters, $K_M$ or $V_{max}$, for either substrates, ATP (FIGS. 5A, 5C) or glucose (FIGS. 5B, 5D), suggesting that Formula C is an allosteric modulator of the VDAC1/HK2 complex.

Example 2

Formula C Effects on CTCL Tumor Cells

The cell lines tested were from a large collection of patient-derived (PDX) and cell line-derived (CDX) human tumor xenografts growing subcutaneously in immunodeficient nude mice (Oncotest GmbH, a Charles River Division). The majority of the xenografts have been directly transplanted from patients and passaged in nude mice. The xenografts retain most of the characteristics of the parental patient tumors including histology and sensitivity to anti-cancer drugs, and efficacy tests in tumor-bearing nude mice largely replicate the response of the donor patient to standard anti-cancer drugs. The cell lines were from publicly available cell lines, including cell lines derived from solid tumors and hematological malignancies. In the clonogenic assay, the capacity of tumor cells for anchorage-independent growth was investigated as colony formation in soft agar in the presence and absence of test compounds. For the assay, tumor cells were harvested from in vitro culture, or tumor cell suspensions were prepared directly from human tumor xenografts growing in nude mice. The cell suspensions also contained tumor stem cells, which are believed to mediate the metastatic and infiltrative potential of a tumor. The results of the clonogenic assay for certain molecular targets were highly predictive for in vivo efficacy of test compounds.

Formula C was investigated for antitumor potency and tumor type selectivity ex vivo in 11 human tumor models (5 tumor cell lines, 6 xenograft-derived cell suspensions) of various histotypes. Tests were carried out using a 3D clonogenic assay in 96-well format using an image based read-out.

TABLE 2

List of Abbreviations

| | |
|---|---|
| CDX | cell line-derived xenograft |
| D | day(s) |
| DMSO | dimethyl sulfoxide |
| PCS | fetal calf serum |
| ICx | inhibitory concentration, where a T/C-value of (100 − x)% is reached |
| IMDM | Iscove's Modified Dulbecco's Medium |
| MoA | mode of action |
| MW | molecular weight |
| n.a. | not applicable |
| n.d. | not determined |
| NMRI | Naval Medical Research Institute, USA |
| PBS | phosphate buffered saline |
| PDX | patient-derived xenografts |
| RPMI | Roosevelt Park Memorial Institute |
| T/C-value | test versus control value |
| U | Unit |
| v/v | volume per volume |
| w/o | without |
| w/v | weight per volume |

Materials and Methods

Compound

Formula C was supplied by ViDAC Pharma Ltd. and stored at −20° C. in the dark. Details about the compound are given in Table 3.

TABLE 3

Designation of Test Articles

| Name | Batch no. | Oncotest designation | MW [g/mol] | Amount delivered | Test concentration |
|---|---|---|---|---|---|
| Formula C | TXK-15-90-4 | Formula C | 337.17 | 13.8 mg | 0.003-30 ˆM (half-log steps) |

Compound Handling

A master stock solution of Formula C was prepared in DMSO at a concentration of 50 mM by adding 818 µl DMSO to 13.8 mg of compound, and aliquots were stored at −20° C. On the day of the experiment, a frozen aliquot was thawed and a working stock solution was prepared in DMSO at a concentration of 9.9 mM (330-fold the highest test concentration), which was stored at room temperature prior to and during treatment. All liquid handling steps were performed using a Tecan Freedom EVO 200 robotic platform. First, serial half-log dilutions of the 330-fold concentrated working stock solution were done in DMSO. The DMSO dilutions were then diluted 1:22 into cell culture medium (IMDM, supplemented with 20% (v/v) fetal calf serum, and 0.01% (w/v) gentamicin) in an intermediate dilution plate. Finally, 10 µl taken from the intermediate dilution plate were transferred to 140 µl/well of the final assay plate. Thus, the DMSO working stock was diluted 1:330, and the DMSO concentration in the assay was 0.3% v/v.

Chemicals and Enzymes

Other chemicals and enzymes needed to perform the clonogenic assay are detailed in Table 4 below.

TABLE 4

Chemicals and Enzymes

| Product | Supplier |
|---|---|
| Bacto Agar | BD Biosciences, 214010 |
| Collagenase type IV | Sigma, C5138 |
| Dispase II | Roche, 4942078001 |
| DNase I | Roche, 11284932001 |
| Hyaluronidase type V | Sigma, H6254 |
| 2-(4-iodophenyl)-3-(4-nitrophenyl)-5-phenyltetrazolium chloride | Sigma, I8377 |

Buffers and Solvents

Buffers and solvents needed to perform the clonogenic assay are detailed in Table 5 below.

TABLE 5

Buffers, Media and Solvents

| Product | Supplier |
|---|---|
| Fetal calf serum (FCS) | Sigma, F7524 |
| Gentamicin | Life Technologies, 15710 |
| Iscove's Modified Dulbecco's Medium (IMDM) | Life Technologies, 21980 |
| PBS Dulbecco's w/o calcium, magnesium, w/o sodium bicarbonate | Life Technologies, 14190 |
| RPMI 1640-Medium with 25 mM HEPES buffer, with L-glutamine | Life Technologies, 52400 |
| RPMI 1640-Medium with 25 mM HEPES buffer, with L-glutamine | Biochrom, FG1385 |

Tumor Models

Formula C was tested in human CTCL tumor cell lines. Additional details of the tumor models are given in Table 6. Publicly available cells were obtained from the sponsor and ECACC (through Sigma-Aldrich, Taufkirchen, Germany).

TABLE 6

Tumor Models Tested in the Clonogenic Assay

| Tumor Designation | Tumor Number | Stage at Implantation | Histology | Differentiation | Patient Age at Surgery | Gender | Source |
|---|---|---|---|---|---|---|---|
| LYXFNH | HH | not available | T cell cutaneous | not known | 61 | male | cell line, sponsor |
| LYXFNH | HUT-78 | not available | T cell cutaneous | good | 53 | male | cell line, ECACC |
| LYXFNH | MJ (G11) | not available | T cell cutaneous | not known | 50 | male | cell line, sponsor |

Cultivation of Cell Lines

Cells were grown at 37° C. in a humidified atmosphere with 5% $CO_2$ in RPMI 1640 medium supplemented with 10% (v/v) fetal calf serum and 0.01% (w/v) gentamicin. Cells were routinely passaged once or twice weekly. The percentage of viable cells was determined in a Neubauer-hemocytometer using trypan blue exclusion.

Preparation of Single Cell Suspensions from Human Tumor Xenografts

Cell line-derived xenografts were passaged as subcutaneous xenografts in NMRI nu/nu mice. At a tumor volume of 400-1000 $mm^3$, tumor-bearing mice were sacrificed and tumors were collected under sterile conditions without delay according to standard operating procedure (SOP) and the animal welfare guidelines published by the FELASA and the GV-SOLAS. Tumors were mechanically disaggregated and subsequently incubated with an enzyme cocktail consisting of collagenase type IV (41 U/mL), DNase I (125 U/mL), hyaluronidase type III (100 U/mL), and dispase II (1.0 U/mL) in RPMI 1640 medium (Life Technologies) at 37° C. for 60-120 minutes. Cells were passed through sieves of 100 µm and 40 µm mesh size (Cell Strainer, BD Falcon™), and washed with RPMI 1640 medium. The percentage of viable cells was determined in a Neubauer-hemocytometer using trypan blue exclusion. Aliquots of the cells were frozen down and stored in liquid nitrogen. On each day of an experiment, a frozen aliquot of tumor cells was thawed and used for preparation of assay plates.

Clonogenic Assay Procedure

The clonogenic assay was carried out in a 96 well plate format using ultra low attachment plates. For each test, cells were prepared as described above, and assay plates were prepared as follows: each test well contained a layer of semi-solid medium with tumor cells (50 µL), and a second layer of medium supernatant with or without test compound (100 µL). The cell layer consisted of $5 \cdot 10^3$-$2.5 \cdot 10^4$ tumor cells per well, which were seeded in 50 µL/well cell culture medium (IMDM, supplemented with 20% (v/v) fetal calf serum, 0.01% (w/v) gentamicin, and 0.4% (w/v) agar). The soft-agar layer was immediately covered with 90 µL of the same culture medium without agar. After 24 hours, Formula C was added after serial dilution in DMSO and transfer in cell culture medium and left on the cells for the duration of the experiment (continuous exposure, 100 µl drug overlay). Every plate included six untreated control wells and drug-treated groups in duplicate at 9 concentrations. Cultures were incubated at 37° C. and 7.5% $CO_2$ in a humidified atmosphere for 8 to 14 days and monitored closely for colony growth using an inverted microscope. Within this period, ex vivo tumor growth led to the formation of colonies with a diameter of >50 µm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 µl/well).

Data Evaluation

An assay was considered fully evaluable if the following quality control criteria were fulfilled:
- mean number of colonies in the control wells >50 colonies with a colony diameter of >50 µm;
- Z'-factor calculated within the assay plate ≥0.5;
- coefficient of variation in the growth control wells ≤30%; and
- the positive reference compound sunitinib at a concentration of 100 µM caused a reduction of signal to <30% of the growth control.

Results were expressed in percentage of colony formation, obtained by comparison of the mean signal in the treated wells with the mean signal of the untreated controls (expressed by the test-versus-control value, T/C-value [%]):

$$\frac{T}{C} [\%] = \frac{\text{mean } signal_{treated\ group}}{\text{mean } signal_{control\ group}} \cdot 100$$

Sigmoidal concentration-response curves were fitted to the data points using 4 parameter non-linear curve fit (Oncotest Warehouse Software). $IC_{50}$ values are reported as absolute $IC_{50}$ values. The absolute $IC_{50}$ value is the concentration at the intersection of the concentration effect curve with T/C=50%. The overall potency of the compound was expressed by the geometric mean $IC_{50}$ value of all individual $IC_{50}$ values.

Figure 9:
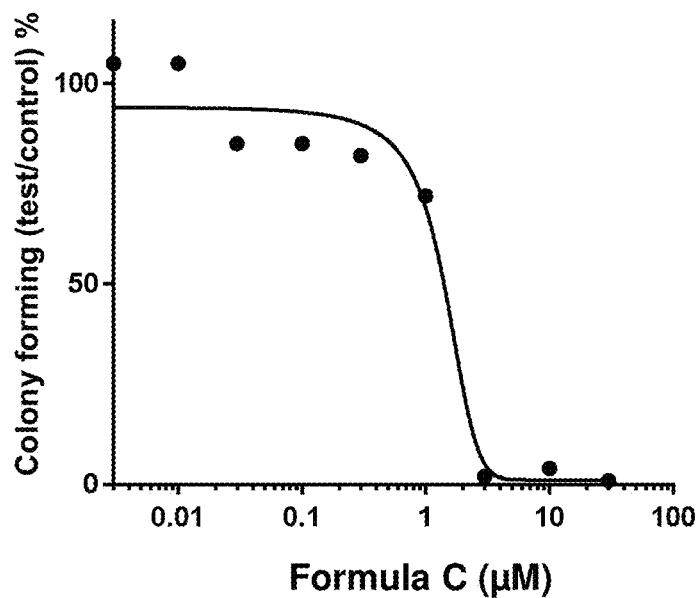
FIG. 9. Efficacy of Formula C in Inhibiting HH Tumor Cell Line Colony Formation. The response of HH cell lines to various concentrations of Formula C were plotted to determine $IC_{50}$ value.

Formula C Inhibits Anchorage Independent Growth and Ex Vivo Colony Formation of CTCL Tumor Cells The ability of Formula C to inhibit ex vivo colony formation of cells with the ability to grow anchorage independently in semi-solid medium was examined. Formula C inhibited HH cell line colony formation in a concentration-dependent manner with a steep concentration-response relationship. Pronounced effects in cell lines were observed starting at a test concentration of 3 µM. In particular, Formula C had a relative $IC_{50}$ of 1.222 and an absolute $IC_{50}$ of 1.195 in cells from the CTCL cell line HH, showing excellent inhibition of colony formation of CTCL (FIG. 9).

Formula C Decreases Cell Viability of CTCL Cell Lines in a Dose-Dependent Manner Cutaneous T-cell lymphoma (CTCL) cell lines MJ and Hut78 were purchased from ATCC (CRL-8294, and TIB-161, respectively). Cells were grown in Iscove's Modified Dulbecco's Media supplemented with 2 mM L-glutamine, 10% fetal bovine serum, 100 U/mL of penicillin and 0.1 mg/mL of streptomycin.

Cells (1-2×10⁴) were seeded in 96-well plates and treated with Formula C. Cell viability was determined 72 hours later using PrestoBlue reagent according to manufacturer's instruction (Life Technologies). The percentage of viability was expressed according to the fluorescence emitted by Formula C-treated cells compared to DMSO-treated control cells. The florescence emission values at 590 nm were measured with the plate-reader Spark 10M—multimode microplate reader (TECAN).

Figure 10:
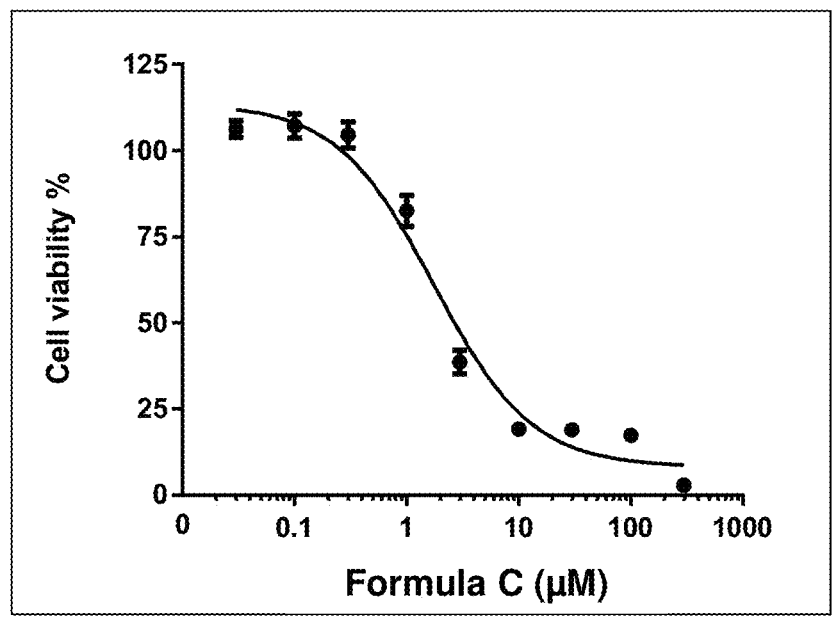
FIG. 10. Efficacy of Formula C in Decreasing MJ CTCL Cell Line Viability. The response of MJ CTCL cell line to various concentrations of Formula C were plotted to determine $IC_{50}$ value.
Figure 11:
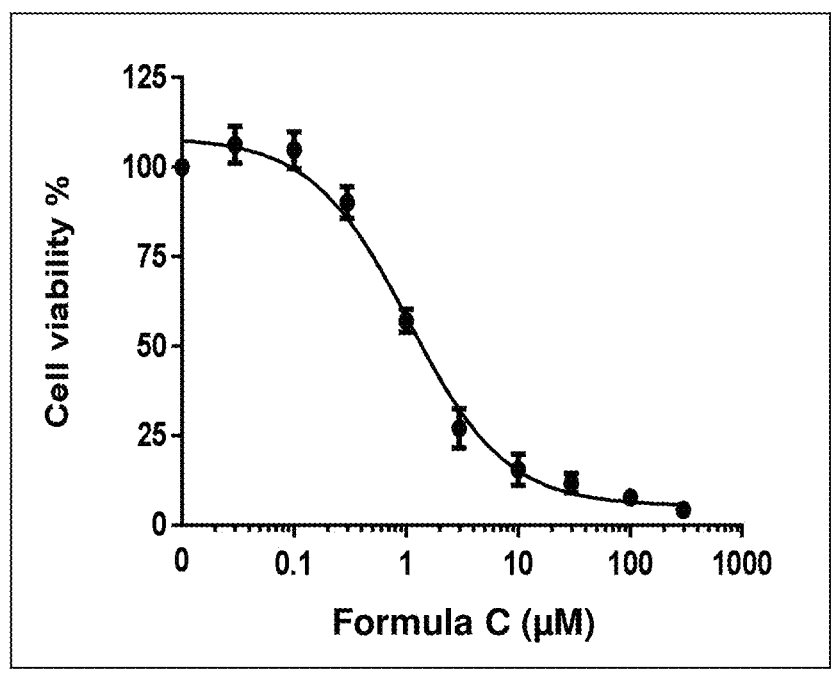
FIG. 11. Efficacy of Formula C in Decreasing Hut-78 CTCL Cell Line Viability. The response of the Hut-78 CTCL cell line to various concentrations of Formula C were plotted to determine $IC_{50}$ value.

Formula C had an absolute $IC_{50}$ of 1.77 in cells from the CTCL cell line MJ (FIG. 10), and an $IC_{50}$ of 1.06 in cells from the CTCL cell line Hut-78 (FIG. 11), showing a strong inhibition of colony formation of CTCL in both cell lines.

Example 3

Formula C Reduces Mitotic Index and Increases Apoptosis In Vivo in Actinic Keratosis (AK) Mouse Model (Chronic UVB-Exposed Hairless Mice)

The effect of Formula C on cell proliferation and apoptosis was tested in an AK/cSCC mouse model of chronic UVB exposure. Forty-eight SKH-1 hairless female mice were chronically exposed to UVB radiation for 16 weeks. By that time, more than 60% of the animals had developed at least one SCC lesion. Three days after the final irradiation dose, the mice were randomly assigned to 1 of 4 treatment groups (N=12 mice/group) and a 50-day treatment phase started. Treatment groups included: vehicle, 2.5% or 5% Formula C ointment applied once-daily for 50 days, or 40% Formula C topical solution applied once-daily for the first 5 days of every three-week cycle (total of three treatment cycles).

There were no adverse local skin reactions of any kind in any of the Formula C treatment groups from Day 1 through Day 50. Specifically, there was no erythema or edema, no abnormalities in body weight, and no clinical signs in any of the groups, suggesting a high safety profile for Formula C. Notably, Formula C did not cause any irritation on skin of naïve SKH-1 mice as well. In fact, toxicology studies in mouse, rat, and minipig, using various modes of administration, all showed low toxicity (FIG. 8).

Histopathological analysis revealed the expected epidermal thickening of AK following chronic UVB exposure, and that the observed SCC lesions were of epidermal origin and in situ, in agreement with previous descriptions of this model (Chaquour et al. 1995; Kligman and Kligman 1981). Formula C treatment resulted in a thinner epidermis, which was histologically similar to the skin of naïve, non UVB-exposed, control mice (data not shown).

Figure 6A:
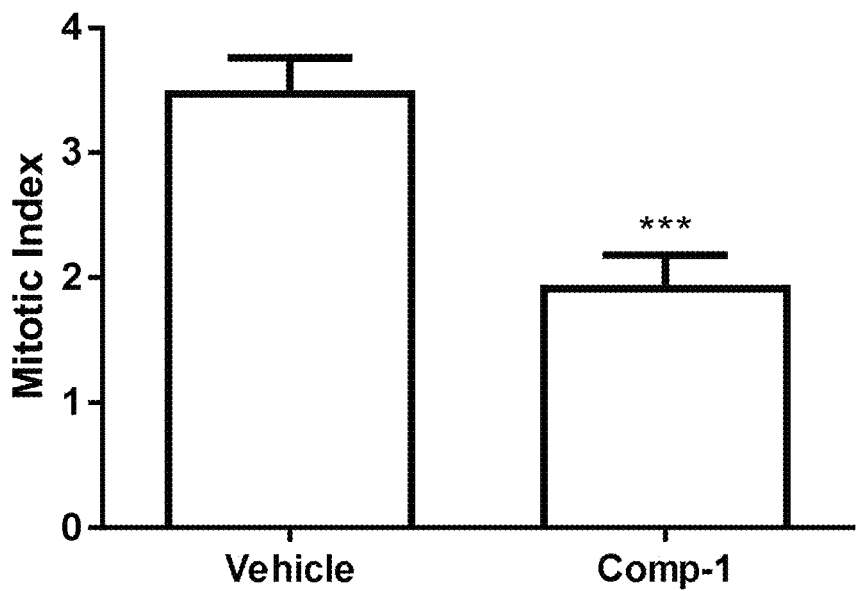
FIG. 6A. Formula C reduces cell proliferation in vivo (Day 50). Mitotic index quantification of the epidermis, vehicle group (n=12) vs. all Formula C treatment groups (n=36). Quantification included the number of mitotic cells per ×40 high power field (HPF), 7 different fields per slide, as evaluated from H&E-stained slides.
Figure 6B:
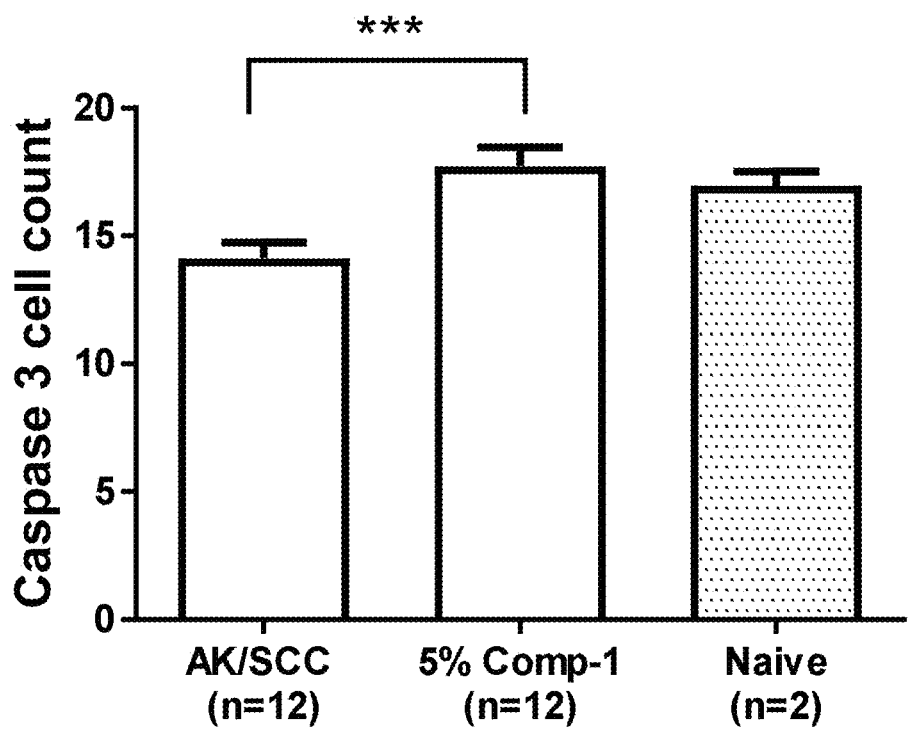
FIG. 6B. Formula C induces apoptosis in vivo (Day 50). Semi-quantification of cleaved caspase-3 positive cells, performed similarly as in (a). n=number of mice. ***p<0.001.

The extent to which cells undergo active proliferation was evaluated using a semi-quantitative histopathological analysis of the epidermis layers on Day 50. The analysis demonstrated that Formula C treatment significantly reduced the mitotic index in AK regions of the skin (FIG. 6A). Furthermore, immunohistochemistry (IHC) analysis of cleaved caspase-3, a marker for early apoptosis, shows a statistically significant induction of apoptosis in Formula C-treated mice (FIG. 6B) to levels similar to those seen in the epidermis of naïve hairless mice.

Example 4 cSCC and Formula C Treatment Alterations in Pharmacodynamic Markers, HK1 and HK2

Figure 7A:
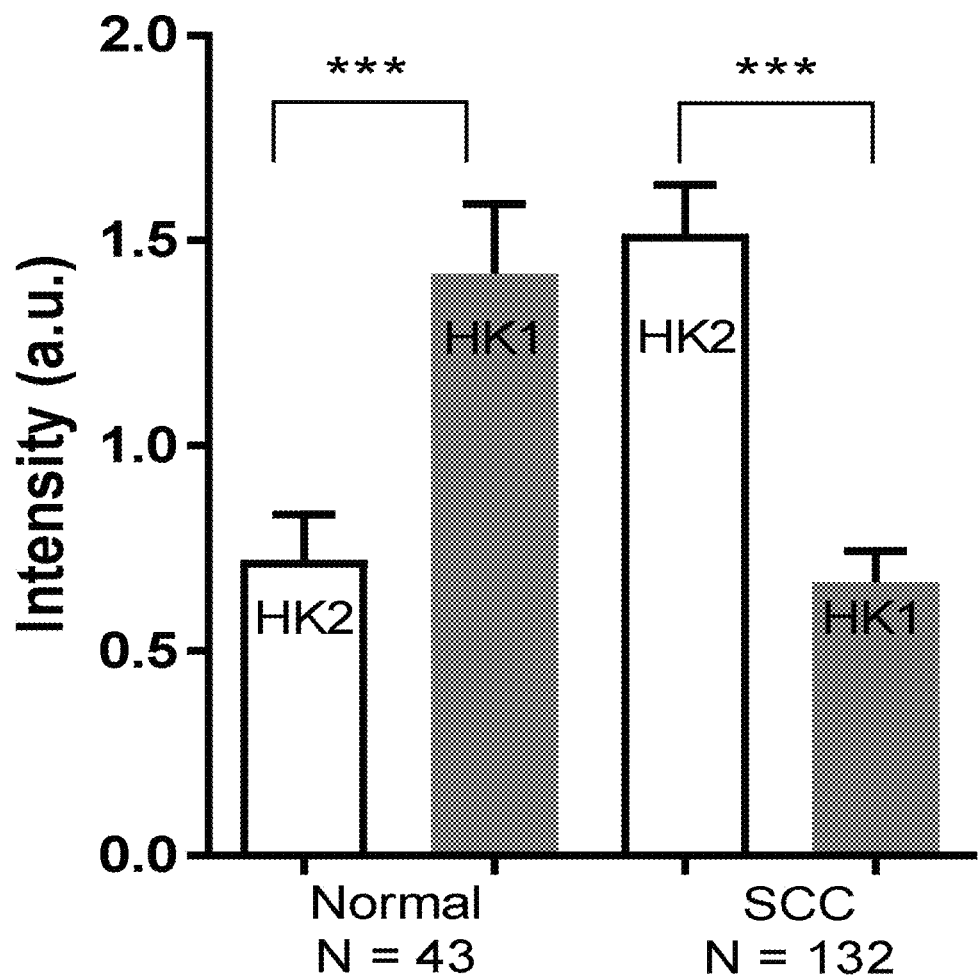
FIG. 7A. Immunohistochemistry of HK1 and HK2 as pharmacodynamic markers for the action of Formula C in Actinic Keratosis (AK)/cutaneous Squamous Cell Carcinoma (cSCC) in human skin epidermis. Quantification of HK1 and HK2 staining intensity (arbitrary scale 0-4) in healthy vs. cSCC from human skin tumor microarray samples. n=number of samples. ***p≤0.001.

IHC analysis of tissue-microarrays from human SCC biopsies revealed that HK1 and HK2 levels in the epidermis differed between normal skin and cSCC. While high HK1 levels and low HK2 levels characterized normal epidermis, the reverse is seen for cSCC (FIG. 7A).

Figure 7B:
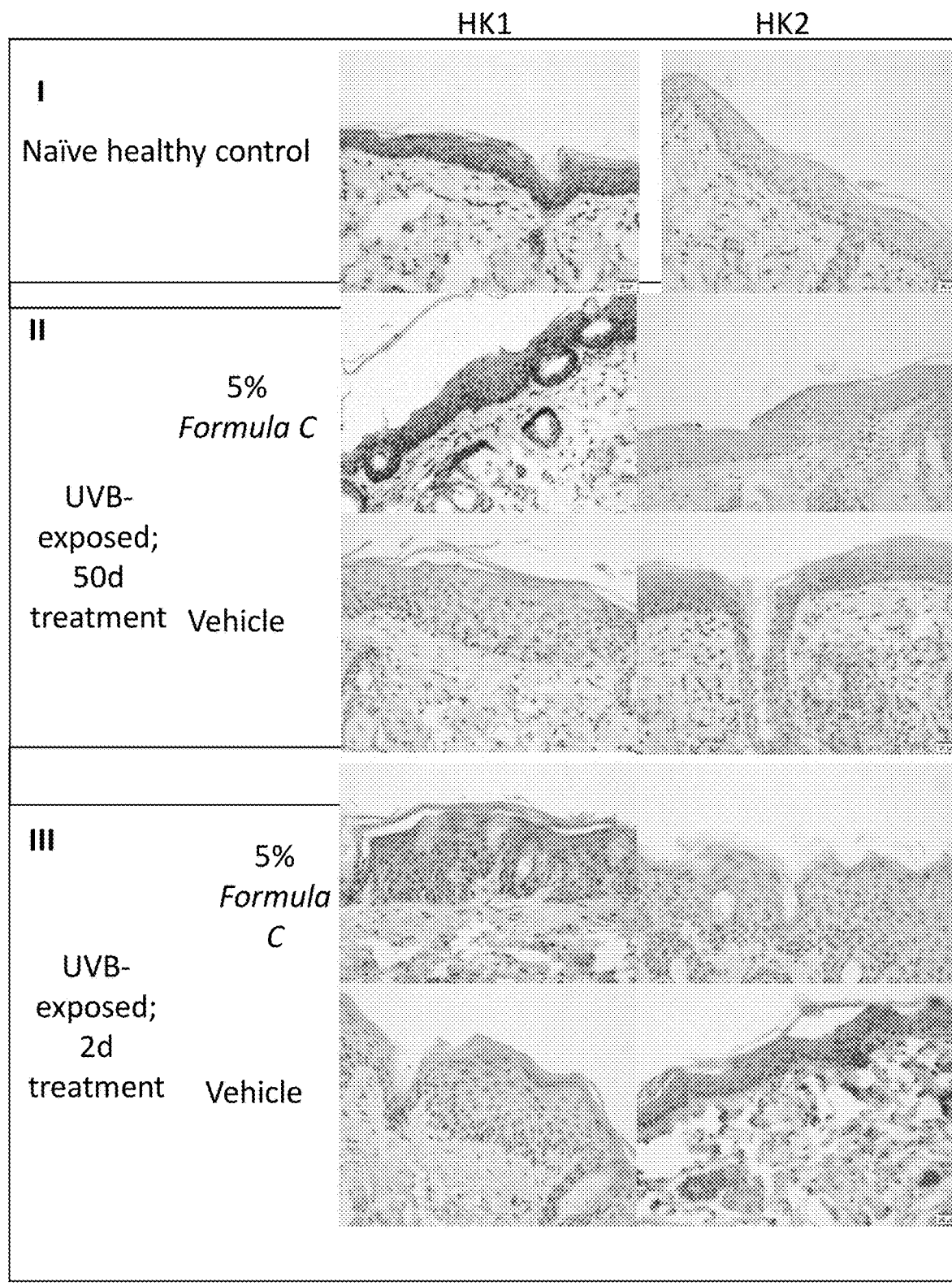
FIG. 7B. Immunohistochemistry of HK1 and HK2 as pharmacodynamic markers for the action of Formula C in AK/cSCC in mouse skin epidermis. HK1 or HK2 staining in slides from the UVB-exposed mouse model of AK/cSCC treated with Formula C. (I) Skin from naïve mice showing strong HK1 intensity and weak HK2 in the epidermis. (II) UVB-exposed skin samples following 50 days of treatment with 5% Formula C or vehicle, showing intense HK2 staining in the disease state (vehicle), which decreases after 50 days of Formula C treatment. HK1 staining exhibits the reverse pattern. (III) Skin following two days of treatment showing a pattern similar to that seen in (II). Scale bar, 20 µm.

IHC analysis was performed on skin tissues from the in vivo UVB-treated mice, assessing HK protein levels as potential mechanism-based pharmacodynamic markers. In line with the above human data, the epidermis of naïve control mice stained strongly positive for HK1 and negative for HK2 (FIG. 7B, I), while UVB-induced AK areas showed a reversal of this pattern (FIG. 7B, II, vehicle group), i.e., strong HK2 and weak HK1 staining, similar to human SCC. Fifty-day treatment with 5% Formula C re-established a profile that resembles normal skin, in which HK2 staining levels are low (FIG. 7B, II, Formula C group).

To assess whether this HK1/HK2 pharmacodynamic marker switch occurs early, a small, not statistically powered, satellite study was conducted with the same 16-week UVB-exposed mice treated for only one or two days with 5% Formula C or vehicle. FIG. 7B, III shows that the AK areas exhibited high HK2 and low HK1 levels by the end of the 16-week UVB irradiation period (vehicle group). Treatment with Formula C for as little as 2 days led to a dramatic decrease in HK2 protein levels, similar to the levels seen on Day 50. Treatment for one day did not show this effect (data not shown).

The data presented here support a novel targeted approach to treat cancer with an allosteric modulator that selectively dissociates the VDAC1/HK2 complex, resulting in reduction of ATP production and induction of apoptosis in the malignant cells. Formula C's anti-proliferative effect in vitro is correlated to HK2 protein levels in the cells.

HK isoform level analysis in vivo further reflects Formula C's selective mode of action, demonstrating low HK2 levels in normal skin and high HK2 levels in the disease state, in both humans and mice. Remarkably, treatment with Formula C reverted the HK1:HK2 ratio back to that seen in normal epidermis. This was evident not only by the completion of the 50-day treatment course, but also after as little as 2 days of treatment.

Example 5

Randomized, Double-Blinded, Placebo-Controlled, Dose-Escalation Study of a Single Topical Application of Formula C Ointment The Phase 1a clinical trial was a randomized, double-blinded, placebo-controlled, dose-escalation study in healthy older-adult volunteers to evaluate the safety, tolerability, and pharmacokinetics of a single topical dermal application of Formula C ointment. The study was conducted under FDA IND in a Phase 1 unit in the United States.

Fifteen healthy volunteers, aged 35-70, were sequentially assigned to 1 of 3 consecutive treatment cohorts (5%, 10% or 20% Formula C ointment, respectively). Five subjects were randomized in a double-blind fashion in each dose cohort: 4 subjects received active Formula C ointment and 1 received matched placebo (0% Formula C; vehicle control). The study ointment (250 mg) was applied once to a 25 centimeter squared area of skin on the forehead of each volunteer.

The Phase 1a study demonstrated: a) No serious adverse events; b) No clinically significant changes at the study drug application sites or in vital signs, physical examinations, clinical laboratory results, ECGs, and Holter monitors for any individual subject at any time point regardless of treatment assignment; c) All adverse events were mild, short-lived and reversible; and d) No systemic exposure of either VDA-1102 or its major metabolite following a single topical application.

Example 6

Phase 1b Multiple Dose in Subjects with AK 7 days×QD 200 mg of drug applied to a 25 cm$^2$ area of face or scalp, double-blind Nested within the Phase 2a study; First 15 subjects followed for 7 days N=15; 3 cohorts (0%, 5%, 10% ointment)

CONCLUSIONS: no AEs or safety signals; local skin reactions were mild to absent.

Example 7

PHASE 2a in Subjects with AK

The Phase 2 clinical trial was a multiple-center randomized, double-blind, placebo-controlled, parallel-cohorts study to evaluate the efficacy, safety, tolerability, and pharmacokinetics of once-daily application of topical Formula C ointment (QD 200 mg) for 28 days in subjects with actinic keratosis. Subjects were followed for one or two months after they completed treatment (through day 56 or day 84). The primary and exploratory efficacy endpoints for the study were reduction in the number of lesions on days 56 and 84, respectively. Subjects were randomly assigned in a double-blind fashion to one of three parallel treatment cohorts (5%, or 10% Formula C, or placebo) at a ratio of 1:1:1. To qualify for the study, subjects aged 18 (inclusive) or older must have had 4-8 discrete Grade 1 or 2 AK lesions within a 25-centimeter squared area of the skin of their scalp or face. The study enrolled 93 subjects in the US and Israel.

Results

The Phase 2a study demonstrated:
1) For the full Intent-to-Treat (ITT) population (subjects treated on face or scalp) the mean reduction in total lesion count from baseline on Day 56, adjusted by site, age, gender and treatment field location, was greater in the 10% VDA-1102 group (32.1%±34.1%) than in Placebo group (27.8%±30.6). A statistically significantly (P=0.023) mean reduction in total lesion count from baseline on Day 56, adjusted to age and gender, was found in the ITT-face subgroup (75.3% of all subjects), where the 10% VDA-1102 group led to 38.8%±36.4% reduction compared to 29.0%±32.5% in the Placebo group. Median reduction in total lesion count from baseline on Day 56 for the full Per Protocol (PP) population was greater for the 10% VDA-1102 group (25.0%) than in the Placebo group (14.6%). Median reduction in total lesion count for the PP-face subgroup was greater for the 10% VDA-1102 group (50.0%) than in the Placebo group (10.0%).
2) No safety signals. There were only 3 treatment-emergent AEs deemed by the investigators to be related to the study drug: 1 mild dyspepsia in the 5% group; 1 mild hypopigmentation in the 5% group (that was evident on dermatoscope pictures already on Day 1 Pre-dose); and a moderate headache in the Placebo group. Two serious adverse events (1 acute pneumonia in the 10% group and 1 elective surgery scheduled prior to Screening in the 5% group) were deemed unrelated. No clinically significant changes at the study drug application sites (Local Skin Reactions) or in vital signs, physical examinations, clinical laboratory results, or ECGs, were reported for any individual subject at any time point regardless of treatment assignment. Two withdrawals and one dose reduction occurred in the placebo group. No deaths.
3) No systemic exposure of either VDA-1102 or its major metabolite following a single topical application.

28 days×QD 200 mg of drug applied to a 25 cm² area of face or scalp of subjects with AK, double-blind, parallel-cohort N=100; 5 cohorts Doses: 200 mg doses daily of 0% (placebo), 5% (qd), 10% (qd, bid), 20% (bid) ointment to 25 cm² on face and scalp Sites: 9 dermatology sites with AK experience (6 in US, 3 in Israel)

End point on Day 84: Reduction in AK lesion count

Example 8

Piperazine Derivative of Formula (1) Induces Apoptosis and Inhibits Glycolysis

Figure 12:
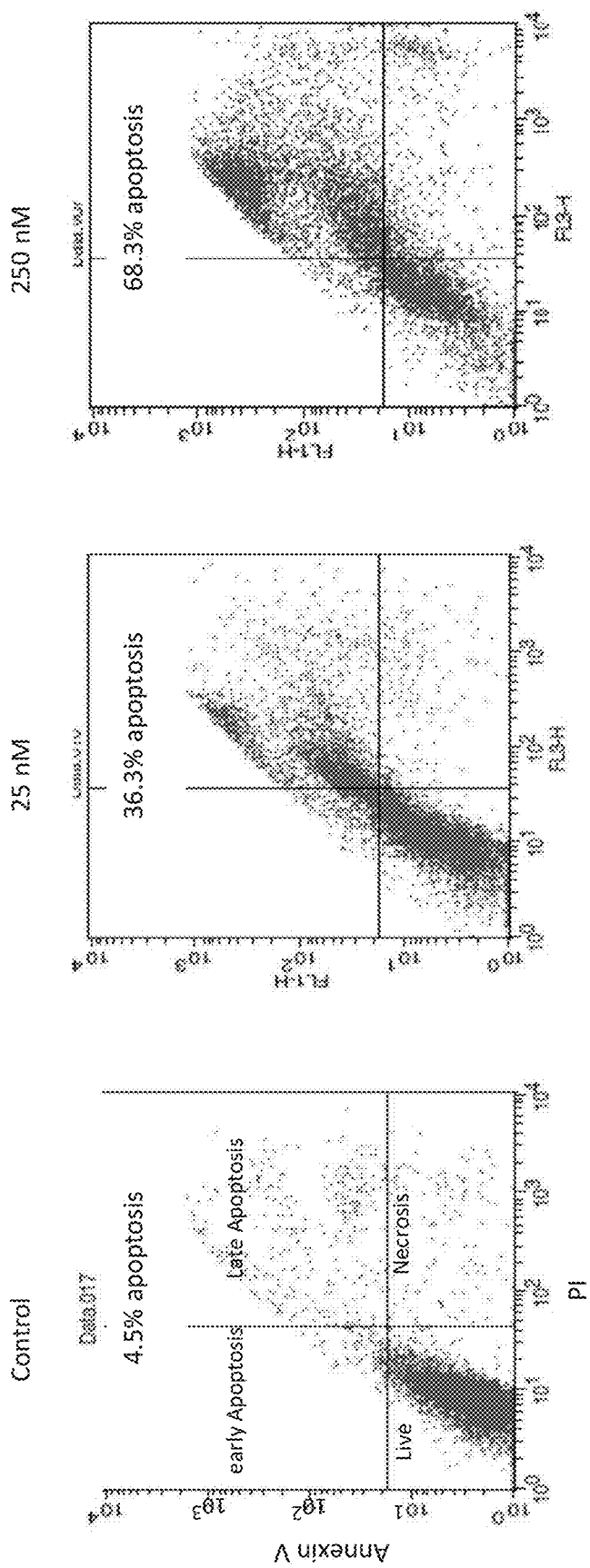
FIG. 12. Apoptosis induction in HeLa cells following 48 hr incubation with VDA-1214. IC50=70 nM. Apoptosis was evaluated by FACS, labeling the cells with propidium iodide and annexin V.
Figure 13:
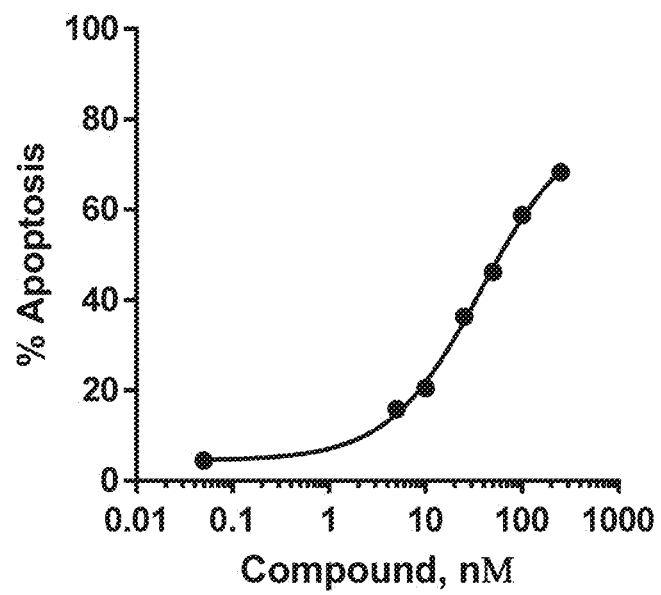
FIG. 13. Apoptosis induction in HeLa cells following 48 hr incubation with Formula (1). IC50=70 nM. Apoptosis was evaluated by FACS, labeling the cells with propidium iodide and annexin V.
Figure 14:
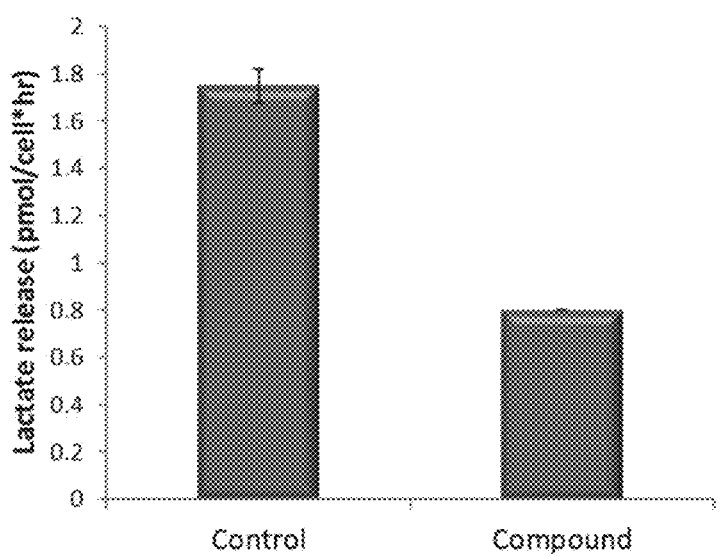
FIG. 14. Lactate levels in the culture media of HeLa cells incubated with 20 µM Formula (1). Lactate levels were assayed with a BioVision kit (Catalog #K607-100).

Administration of the compound of Formula (1) dose-dependently caused cancer cell death by apoptosis (FIGS. 12-13), with an IC50 of 70 nM. Incubation of HeLa cells with the compound of Formula (1) lowered lactate levels (FIG. 14), indicating inhibition of glycolysis.

The present disclosure is not limited to the drawings or to the corresponding descriptions. Meanings of technical and scientific terms used herein are to be commonly understood as by one of ordinary skill in the art to which the disclosure belongs, unless otherwise defined.

While certain features have been illustrated and described with respect to a limited number of embodiments, these should not be construed as limitations on the scope of the disclosure, but rather as exemplifications of some of the embodiments. Other possible variations, modifications, substitutions, changes, and equivalents are also within the scope of the disclosure. Accordingly, the scope of the disclosure should not be limited by what has thus far been described, but by the appended claims, which are intended to cover all such modifications and changes as fall within the true spirit of the invention and their legal equivalents.

What is claimed is:

1. A method for treating, inhibiting or suppressing a hyperproliferative disorder in a subject or for inhibiting the proliferation of hyperproliferative cells in a subject having a hyperproliferative disorder, wherein said hyperproliferative disorder is characterized by detectable HK2 levels or HK2 activity comprising contacting said subject with a therapeutically effective amount of a compound that promotes the detachment of HK2 from the mitochondrial voltage-dependent anion channel (VDAC) wherein said compound is represented by the structure of Formula (VII):

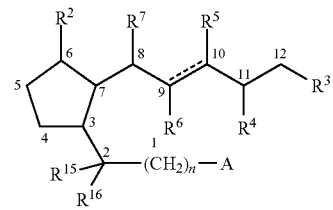

wherein A comprises $COR^1$;

$R^1$ comprises an unsubstituted or substituted heteroaryloxy;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen;

and n is selected from 0, 1 and 2; including salts, hydrates, solvates, polymorphs, optical isomers, geometrical isomers, enantiomers, diastereomers, and mixtures thereof, wherein said detectable HK2 levels or HK2 activity is in a tissue that does not normally have HK2 levels or HK2 activity that is detectable above background levels.

2. The method of claim 1, wherein A comprises $COR^1$; $R^1$ is quinolinyloxy; $R^2$ is oxo; $R^3$, $R^4$, $R^5$, $R^6$ and $R^7$ are each hydrogen, wherein the bond between $C_9$ and $C_{10}$ can be a single or double bond; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof.

3. The method of claim 2, wherein the compound is represented by the structure of Formula C:

4. The method of claim 3, wherein said compound is formulated for subcutaneous administration.

5. The method of claim 1, wherein said hyperproliferative disorder characterized by detectable HK2 levels or HK2 activity comprises a pre-cancerous condition or a benign hyperproliferative disorder.

6. The method of claim 5, wherein said pre-cancerous condition is actinic keratosis.

7. The method of claim 5, wherein said benign hyperproliferative disorder is psoriasis.

8. The method of claim 1, wherein said hyperproliferative disorder characterized by detectable HK2 levels or HK2 activity comprises a cancer or a tumor.

9. The method of claim 8, wherein said tumor comprises a solid tumor.

10. The method of claim 9, wherein said solid tumor comprises breast cancer, prostate cancer, skin cancer, stomach cancer, colon cancer, kidney cancer, or a combination thereof.

11. The method of claim 10, wherein said prostate cancer comprises castration resistant prostate cancer (CRPC) or metastatic CRPC.

12. The method of claim 9, wherein said solid tumor comprises pancreatic cancer.

13. The method of claim 9, wherein said solid tumor comprises lung cancer.

14. The method of claim 13, wherein said lung cancer comprises small cell lung carcinoma, non-small cell lung carcinoma, or large cell lung carcinoma.

15. The method of claim 13, wherein said lung cancer comprises non-small-cell lung carcinoma (NSCLC) (large), NSCLC (adeno), or NSCLC (epidermoid).

16. The method of claim 10, wherein said skin cancer comprises a melanoma.

17. The method of claim 9, wherein said solid tumor comprises a sarcoma, a carcinoma, or a lymphoma.

18. The method of claim 17, wherein said carcinoma comprises squamous cell carcinoma, basal cell carcinoma, or a combination thereof.

19. The method of claim 17, wherein said lymphoma comprises a cutaneous T-cell lymphoma (CTCL).

20. The method of claim 19, wherein said CTCL is mycosis fungoides or Sezary syndrome.

21. The method of claim 8, wherein said cancer comprises a hematological malignancy.

22. The method of claim 21, wherein said hematological malignancy comprises leukemia.

23. The method of claim 22, wherein said leukemia comprises lymphoblastic leukemia.

24. The method of claim 21, wherein said hematological malignancy comprises multiple myeloma.

25. The method of claim 9, wherein said solid tumor comprises head & neck cancer, pancreatic cancer, liver cancer, or a combination thereof.

26. The method of claim 8, wherein said cancer or tumor comprises Non-Hodgkin Lymphoma, Acute myeloid leukemia (AML), Acute lymphocytic leukemia (ALL), B-cell Chronic lymphocytic leukemia (B-CLL), Hepatocellular carcinoma (HCC), or a combination thereof.

27. The method of claim 1, further comprising the step of contacting one or more cells of said subject with an anti-cancer treatment.

28. The method of claim 27, wherein said anti-cancer treatment comprises radiotherapy or administration of a chemotherapeutic.

29. The method of claim 28, wherein said chemotherapeutic comprises 5-fluorouracil, Bleomycin, capecitabine, cisplatin, Cyclophosphamide, dacarbazine, Doxorubicin, Epirubicin, etoposide, folinic acid, Methotrexate, Mustine, oxaliplatin, prednisolone, procarbazine, vinblastine, vincristine, or a combination thereof.

30. The method of claim 27, wherein said anti-cancer treatment comprises administration of an immunotherapeutic compound.

31. The method of claim 30, wherein said immunotherapeutic compound comprises imatinib or trastuzumab.

32. The method of claim 30, wherein said immunotherapeutic compound comprises a checkpoint inhibitor.

33. The method of claim 32, wherein said checkpoint inhibitor comprises a Programmed cell Death protein 1 (PD1) inhibitor or a Programmed cell Death Ligand 1 (PD-L1) inhibitor.

34. The method of claim 33, wherein said PD-1 or PD-L1 inhibitor is an antibody.

35. The method of claim 34, wherein said antibody comprises Nivolumab, Pembrolizumab, Pidilizumab, Avelumab, BMS 936559, or MPDL328OA.

36. The method of claim 30, wherein said immunotherapeutic compound comprises chimeric antigen receptor T cells (CAR T-cells).

37. The method of claim 1, wherein said subject is immunocompromised.

38. The method of claim 1, wherein said compound is present in a composition.

39. The method of claim 38, wherein said composition is formulated for topical administration.

40. The method of claim 39, wherein said composition is formulated as an ointment, a cream, a lotion, a foam or a gel.

41. The method of claim 38, wherein said composition is formulated for parenteral administration.

42. The method of claim 38, wherein said composition is formulated for intravenous, subcutaneous, or intramuscular administration.

43. The method of claim 1, wherein HK2 levels comprise gene expression levels of HK2 or protein expression levels of HK2.

44. The method of claim 43, wherein said gene expression levels are detected via microarrays or RNA-seq.

45. The method of claim 43, wherein protein expression levels are detected via Western blot.

46. The method of claim 43, wherein protein expression levels are detected via immunohistochemistry or enzyme-linked immunosorbent assay (ELISA).

47. The method of claim 1, wherein said HK2 activity is detected via fluorodeoxyglucose (FDG)-positron emission tomography (PET) scan.

48. The method of claim 1, wherein said HK2 levels or HK2 activity is detectable in a sample from said HK2-expressing hyperproliferative disorder.

49. The method of claim 48, wherein said sample comprises a biopsy.

50. The method of claim 49, wherein said sample comprises a tissue aspirate.

51. The method of claim 1, wherein said tissue that does not normally have HK2 levels or HK2 activity that is detectable above background levels comprises lung tissue, breast tissue, colon tissue, or a combination thereof.

52. The method of claim 1, wherein said tissue that does not normally have HK2 levels or HK2 activity that is detectable above background levels does not comprise adipose tissue, skeletal muscle, or heart.

* * * * *